(12) United States Patent
Birch et al.

(10) Patent No.: US 7,655,836 B2
(45) Date of Patent: Feb. 2, 2010

(54) METHOD FOR INCREASING PRODUCT YIELD

(75) Inventors: Robert George Birch, Jindalee (AU); Luguang Wu, Kenmore (AU)

(73) Assignee: The University of Queensland, St. Lucia, Queensland (AU)

( * ) Notice: Subject to any disclaimer, the term of this patent is extended or adjusted under 35 U.S.C. 154(b) by 633 days.

(21) Appl. No.: 10/845,059

(22) Filed: May 12, 2004

(65) Prior Publication Data

US 2005/0005323 A1   Jan. 6, 2005

(30) Foreign Application Priority Data

May 12, 2003   (AU)   .............. 2003902253

(51) Int. Cl.
| | |
|---|---|
| C12N 15/82 | (2006.01) |
| C12N 15/31 | (2006.01) |
| C12N 15/62 | (2006.01) |
| C12N 5/04 | (2006.01) |
| A01H 5/00 | (2006.01) |
| C12P 7/06 | (2006.01) |
| C12P 19/02 | (2006.01) |
| C12P 19/12 | (2006.01) |

(52) U.S. Cl. .................. 800/284; 800/287; 800/288; 800/320; 435/69.8; 435/100; 435/105; 435/161

(58) Field of Classification Search .............. 435/6, 435/69.1, 468, 419, 252.3, 320.1; 530/370; 536/23.7; 800/278, 295, 320
See application file for complete search history.

(56) References Cited

U.S. PATENT DOCUMENTS

| | | | |
|---|---|---|---|
| 4,399,216 A | 8/1983 | Axel et al. | ................ 435/6 |
| 5,004,863 A | 4/1991 | Umbeck | .............. 800/205 |
| 5,290,924 A | 3/1994 | Last et al. | ............. 536/24.1 |
| 5,773,691 A | 6/1998 | Falco et al. | ............ 800/205 |
| 5,985,668 A * | 11/1999 | Mattes et al. | ........... 435/471 |
| 5,986,173 A * | 11/1999 | Smeekens et al. | ..... 800/284 |
| 6,391,639 B1 * | 5/2002 | Schenk et al. | .......... 435/419 |
| 7,250,282 B2 * | 7/2007 | Birch et al. | ............. 435/233 |

FOREIGN PATENT DOCUMENTS

| | | |
|---|---|---|
| DE | 100 45 113 A1 | 8/2001 |
| WO | WO 95/20047 | 7/1995 |
| WO | WO 01/18211 A1 | 3/2001 |
| WO | WO 01/59135 A1 | 8/2001 |
| WO | WO 01/59136 A1 | 8/2001 |
| WO | WO 01/60993 * | 8/2001 |
| WO | WO 02/18603 A1 | 3/2002 |
| WO | WO 02/27003 A1 | 4/2002 |

OTHER PUBLICATIONS

Sweetlove et al (1996) Starch Metabolism In Tubers Of Transgenic Potato (Solanum Tuberosum) With Increased ADP-Glucose Pyrophosphorylase. Biochem J. 30:493-98.*
Melchers, et al., (1993) Plant Molec. Biol. 21:583-593).*
Bornke, et al., (2002) Planta 214:356-364).*
Turk, et al., New Phytol (1997) 136:29-38.*
Smeekens et al, (1987) Plant Molec. Biology 9:377-388.*
Sutton, et al., (1992) Transgenic research, vol. 1, No. 5, pp. 228-236).*
Caddick, Caddick, (1998) Nature Biotechnology, 16: 177-180; Cf. Fischer et al, (1997) Plant J. 11:489-498; Cf. Bower, et al., (1996).*
Fischer et al, (1997) Plant J. 11:489-498.*
Bower, et al., (1996) Molecular Breeding, 2:239-249.*
van der Meer et al. The Plant Cell 9: 561-570 (Apr. 1994).*
Ebskamp et al. Bio/Technology 12(3): 272-275 (Mar. 1994).*
Patrick, John. Faculty of 1000 Biology website, f1000biology.com/article/id/1063782/evaluation (Feb. 5, 2007).*
Frommer, Wolf. Faculty of 1000 Biology website, f1000biology.com/article/id/1063782/evaluation (Feb. 16, 2007).*
Gressel, Jonathan. Plant Science 174: 246-263 (2008).*
van Beilen, Jan. Biofuels, Bioproducts & Biorefining 2: 215-228 (2008).*
Smith, Alison. The Plant Journal 54: 546-558 (2008).*
Nicholson, Tarryn. M.S. Thesis, University of Stellenbosch (Dec. 2007).*
Wu et al. Plant Biotechnology Journal 5(1): 109-117 (Jan. 2007).*
Morandini, Piero. Plant Science 176(4): 441-451 (Apr. 2009).*
Braun et al. Plant Physiology 149(1): 71-81 (Jan. 2009).*
Adams, M, et al., "Simultaneous Determination by Capillary Gas Chromatography of Organic Acids, Sugars, and Sugar Alcohols in Plant Tissue Extracts as their Trimethylsilyl Derivatives," *Anal. Biochem.* 266(1):77-84, Jan. 1, 1999.
Bevan, M.,et al., "A Chimaeric Antibiotic Resistance Gene as a Selectable Marker for Plant Cell Transformation," *Nature* 304:184-187, Jul. 14, 1983.
Börnke, F.,et al., "Potato Tubers as Bioreactors for Palatinose Production," *J. Biotechnol.* 96(1):119-24, Jun. 13, 2002.
Börnke, F.,et al., "High-level Production of the Non-cariogenic Sucrose Isomer Palatinose in Transgenic Tobacco Plants Strongly Impairs Development," *Planta* 214(3)356-64, Jan. 2002.

(Continued)

*Primary Examiner*—David T Fox
(74) *Attorney, Agent, or Firm*—SEED IP Law Group PLLC

(57) ABSTRACT

The present invention relates to methods for increasing the yield of a compound produced by an organism. More particularly, the present invention relates to methods for increasing the total or soluble carbohydrate content or sweetness or increasing the content of an endogenous carbohydrate of a plant tissue by producing a sugar-metabolizing enzyme that catalyzes the conversion of an endogenous sugar (one that is normally produced in the plant) to an alien sugar (one that is not normally produced in the plant at the same developmental stage). The invention also relates to plants and plant parts that produce a sugar-metabolizing enzyme to yield an alien sugar, with the consequence of higher total fermentable carbohydrate content, and to fermentable carbohydrates and other products derived therefrom.

77 Claims, 21 Drawing Sheets

OTHER PUBLICATIONS

Botha, F., et al., "Sucrose Metabolism in the Culm of Transgenic Sugarcane with Reduced Soluble Acid Invertase Activity," in *Proceedings of the International Society of Sugarcane Technologists XXIV Congress*, Brisbane, Sep. 2001, vol. II (Hogarth DM, ed) Mackay: ASSCT, pp. 588-591, 2001.

Callis, J., et al., "Introns Increase Gene Expression in Cultured Maize Cells," *Genes Dev.* 1(10):1183-200, Dec. 1987.

Deikman et al., Interaction of a DNA Binding Factor with the 5'-flanking Region of an Ethylene-responsive Fruit Ripening Gene from Tomato, *EMBO J.* 7(11):3315-20, Nov. 1988.

Demuth, K., et al., "Oligosaccharide Synthesis by Dextransucrase: New Unconventional Acceptors," *Carbohydr Res.* 337(20):1811-20, Nov. 5, 2002.

Fernie, A., et al., "The Sucrose Analog Palatinose Leads to a Stimulation of Sucrose Degradation and Starch Synthesis when Supplied to Discs of Growing Potato Tubers," *Plant Physiol.* 125:1967-1977, Apr. 2001.

Gallie, D., et al., "Visualizing mRNA Expression in Plant Protoplasts: Factors Influencing Efficient mRNA Uptake and Translation," *Plant Cell* 1(3):301-11, Mar. 1989.

Giovannoni, J., et al., "Expression of a Chimeric Polygalacturonase Gene in Transgenic *rin* (ripening inhibitor) Tomato Fruit Results in Polyuronide Degradation but not Fruit Softening," *Plant Cell* 1(1):53-63, Jan. 1989.

Hansom, S., et al., "Regulation of Transgene Expression in SugarCane," in *Proceedings of the International Society of Sugarcane Technologists XXIII Congress*, New Delhi, Feb. 1999, pp. 278-290.

von Heinje, G., et al., "Domain Structure of Mitochondrial and Chloroplast Targeting Peptides," *Eur. J. Biochem.* 180(3):535-45, Apr. 1, 1989.

Lessard, P., et al., "Manipulating Gene Expression for the Metabolic Engineering of Plants," *Metab. Eng.* 4(1):67-79, Jan. 2002.

Loreti, E., et al., "Glucose and Disaccharide-sensing Mechanisms Modulate the Expression of Alpha-amylase in Barley Embryos," *Plant Physiol.* 123:939-948, Jul. 2000.

Martin, M., et al., "Synthesis of Maltooligosyl Fructofuranosides Catalyzed by Immobilized Cyclodextrin Glucosyltransferase Using Starch as Donor," *Tetrahedron* 60:529-534, 2004.

Moore, P., "Temporal and Spatial Regulation of Sucrose Accumulation in the Sugarcane Stem," *Australian Journal of Plant Physiology* 22:661-679, 1995.

Nguyen-Quoc B., et al., "A Role for 'Futile Cycles' Involving Invertase and Sucrose Synthase in Sucrose Metabolism of Tomato Fruit," *Journal of Experimental Botany* 52(358): 881-889, May 2001.

Peach, C., et al., "Transgene Expression Variability (position effect) of CAT and GUS Reporter Genes Driven by Linked Divergent T-DNA Promoters," *Plant Mol. Biol.* 17(1):49-60, Jul. 1991.

Sinha, A., "Metabolizable and Non-metabolizable Sugars Activate Different Signal Transduction Pathways in Tomato," *Plant Physiol.* 128, 1480-1489, Apr. 2002.

Small, I., "Two Birds with One Stone: Genes that Encode Products Targeted to Two or More Compartments," *Plant Molecular Biology* 38, 265-277, 1998.

van der Veen, B., et al., "Combinatorial Engineering to Enhance Amylosucrase Performance: Construction, Selection, and Screening of Variant Libraries for Increased Activity," *FEBS Letters* 560:91-97, 2004.

Vitale, A., et al., "What do Proteins Need to Reach Different Vacuoles?," *Trends in Plant Science* 4(4):149-155, Apr. 1999.

Wu, L., et al., "Characterization of *Pantoea dispersa UQ68J*: Producer of a Highly Efficient Sucrose Isomerase for Isomaltulose Biosynthesis," *J. Applied Microbiology* 97:93-103, 2004.

Zhifang, G., et al., "Expression of a Celery Mannose 6-phosphate Reductase in *Arabidopsis thaliana* Enhances Salt Tolerance and Induces Biosynthesis of both Mannitol and a Glucosyl-mannitol Dimmer," *Plant Cell and Environment* 26:275-283, 2003.

\* cited by examiner

SEQUENCE LISTING

```
<160> NUMBER OF SEQ ID NOS: 26

<210> SEQ ID NO 1
<211> LENGTH: 35
<212> TYPE: DNA
<213> ORGANISM: Artificial
<220> FEATURE:
<223> OTHER INFORMATION: UQErw forward primer for cytosol-targeting

<400> SEQUENCE: 1
ggatccaaca atggcaaccg ttcagcaatc aaatg                                35

<210> SEQ ID NO 2
<211> LENGTH: 35
<212> TYPE: DNA
<213> ORGANISM: Artificial
<220> FEATURE:
<223> OTHER INFORMATION: UQ14S forward primer for cytosol-targeting

<400> SEQUENCE: 2
ggatccaaca atggcaaccg ttcacaagga aagtg                                35

<210> SEQ ID NO 3
<211> LENGTH: 34
<212> TYPE: DNA
<213> ORGANISM: Artificial
<220> FEATURE:
<223> OTHER INFORMATION: UQ68J forward primer for cytosol-targeting

<400> SEQUENCE: 3
ggatccaaca atggcaacga atatacaaaa gtcc                                 34

<210> SEQ ID NO 4
<211> LENGTH: 28
<212> TYPE: DNA
<213> ORGANISM: Artificial
<220> FEATURE:
<223> OTHER INFORMATION: UQErw reverse primer for cytosol-targeting

<400> SEQUENCE: 4
ataggtacct tacttaaacg cgtggatg                                        28

<210> SEQ ID NO 5
<211> LENGTH: 30
<212> TYPE: DNA
<213> ORGANISM: Artificial
```

-continued

```
<220> FEATURE:
<223> OTHER INFORMATION: UQ14S reverse primer for cytosol-targeting

<400> SEQUENCE: 5
ataggtacct taccgcagct tatacacacc                                    30

<210> SEQ ID NO 6
<211> LENGTH: 30
<212> TYPE: DNA
<213> ORGANISM: Artificial
<220> FEATURE:
<223> OTHER INFORMATION: UQ68J reverse primer for cytosol-targeting

<400> SEQUENCE: 6
ataggtacct cagttcagct tatagatccc                                    30

<210> SEQ ID NO 7
<211> LENGTH: 111
<212> TYPE: DNA
<213> ORGANISM: Artificial
<220> FEATURE:
<223> OTHER INFORMATION: DNA encoding modified ER signal and N-terminal
      propeptide (NTPP) from sweet potato sporamin

<400> SEQUENCE: 7
atgaaggcct tcaccctcgc cctcttcctc gccctctccc tctacctcct cccgaacccg   60
gcccactccc gcttcaaccc gatccgcctc ccgaccaccc acgagccggc c            111

<210> SEQ ID NO 8
<211> LENGTH: 69
<212> TYPE: DNA
<213> ORGANISM: Artificial
<220> FEATURE:
<223> OTHER INFORMATION: DNA encoding modified ER signal from tobacco
      chitinase

<400> SEQUENCE: 8
atgaggcttt gtaaattcac agctctctct tctctactat tttctctcct actgctttct   60
gcctcggcg                                                           69

<210> SEQ ID NO 9
<211> LENGTH: 36
<212> TYPE: DNA
<213> ORGANISM: Artificial
<220> FEATURE:
<223> OTHER INFORMATION: DNA encoding C-terminal propeptide (CTPP) from
      tobacco chitinase

<400> SEQUENCE: 9
catagtatcg actaagagac cgttcagctt atagat                             36

<210> SEQ ID NO 10
<211> LENGTH: 987
<212> TYPE: DNA
<213> ORGANISM: Saccharum sp.
<220> FEATURE:
<221> NAME/KEY: promoter
<222> LOCATION: (1)..(987)
<223> OTHER INFORMATION: DNA sequence of promoter P67B

<400> SEQUENCE: 10
gagctctcga tgggaggtgc tcgaagacat attagccaag tgtatggcaa gatgtttagc   60
tagtagctga ctgatagtgt aaacgatctc caatggggca agacatatta cctaaggcca  120
ggctggtttt tgcaagtttg agtaggatat agagattctc gtgcgagttg taaacgatct  180
```

```
ccaatggggc aagacatcct aacctatata tagtgaaggg gcagtagctg attgagaatc    240
aaccaatcaa gcacaatata atttattaat ttttattca aacccaattt tttccttttc    300 caacccaat tatagttctc cttttgcctc taggacaaat tgacgtgttc ctggtatccc    360
tgggtaggca ttcataggga tacgggtatt tcctgcaaaa aagcgattaa gctggcttct    420
aaaactggct aggccggatt ctgtggcctt cactaccagg tgattttcat gtgatccgtg    480
cattctagca ctttgctgtg taacccaaac tgatgtcgac aactataaat atgctacttg    540
caggatgtta tcatgacaca actccctaat ctacgaagcc taagtttagt tttgctcgga    600
gacaagcaat tgtggccagt cactttagct acgtcagagg gtagtgggag cagttgcgtc    660
gttggattga aaacaggtgg atcatattag atattattca catgaacagt aaatgtggta    720
cagtaacttc gcaaacaata aaatctgtca caatttatta gtgcactcct ctgacgtaaa    780
tgcttctacg tcagaggatt tgagtccgag gggtgctgca cccatcacta atgacggtct    840
ttacccatca tcatggacca ttgttcacat ccatgctatc actgtcgtcc tgtccatgca    900
ctgcagccct ctataaatac tggcacccct ccccgttca cagatcacac cacacaagca    960
agaaataaac ggtagctgca taactag                                      987

<210> SEQ ID NO 11
<211> LENGTH: 31
<212> TYPE: DNA
<213> ORGANISM: Artificial Sequence
<220> FEATURE:
<223> OTHER INFORMATION: UQ68J forward primer for vacuole targeting
      (NTPP, or NTPP + CTPP constructs)

<400> SEQUENCE: 11
gtagatctcg caacgaatat acaaaagtcc g                                  31

<210> SEQ ID NO 12
<211> LENGTH: 27
<212> TYPE: DNA
<213> ORGANISM: Artificial
<220> FEATURE:
<223> OTHER INFORMATION: UQ68J reverse primer for vacuole targeting
      (NTPP constructs)

<400> SEQUENCE: 12
aagagctcag ttcagcttat agatccc                                       27

<210> SEQ ID NO 13
<211> LENGTH: 45
<212> TYPE: DNA
<213> ORGANISM: Artificial
<220> FEATURE:
<223> OTHER INFORMATION: UQ68J reverse primer for vacuole targeting with
      6 x His tag (NTPP constructs)

<400> SEQUENCE: 13
aagagctcag tggtggtggt ggtggtggtt cagcttatag atccc                   45

<210> SEQ ID NO 14
<211> LENGTH: 45
<212> TYPE: DNA
<213> ORGANISM: Artificial
<220> FEATURE:
<223> OTHER INFORMATION: UQ68J reverse primer for CTPP constructs

<400> SEQUENCE: 14
gagctcacat agtatcgact aagagaccgt tcagcttata gatcc                   45
```

<210> SEQ ID NO 15
<211> LENGTH: 63
<212> TYPE: DNA
<213> ORGANISM: Artificial
<220> FEATURE:
<223> OTHER INFORMATION: UQ68J reverse primer for CTPP constructs with 6 x His tag

<400> SEQUENCE: 15
gagctcagtg gtggtggtgg tggtgcatag tatcgactaa gagaccgttc agcttataga    60
tcc    63

<210> SEQ ID NO 16
<211> LENGTH: 24
<212> TYPE: DNA
<213> ORGANISM: Artificial
<220> FEATURE:
<223> OTHER INFORMATION: Chitinase ER leader peptide forward primer

<400> SEQUENCE: 16
aaggatccaa tgaggctttg aaaa    24

<210> SEQ ID NO 17
<211> LENGTH: 26
<212> TYPE: DNA
<213> ORGANISM: Artificial
<220> FEATURE:
<223> OTHER INFORMATION: Chitinase ER leader peptide reverse primer

<400> SEQUENCE: 17
aaagatctcg ccgaggcaga aagcag    26

<210> SEQ ID NO 18
<211> LENGTH: 23
<212> TYPE: DNA
<213> ORGANISM: Artificial
<220> FEATURE:
<223> OTHER INFORMATION: Promoter 67 forward primer

<400> SEQUENCE: 18
tggagctcga tgggaggtgc tcg    23

<210> SEQ ID NO 19
<211> LENGTH: 29
<212> TYPE: DNA
<213> ORGANISM: Artificial
<220> FEATURE:
<223> OTHER INFORMATION: Promoter 67 reverse primer

<400> SEQUENCE: 19
atggatcctg tactagttat ggcagctac    29

<210> SEQ ID NO 20
<211> LENGTH: 49
<212> TYPE: DNA
<213> ORGANISM: Artificial
<220> FEATURE:
<223> OTHER INFORMATION: Probe to distinguish promoter P67B from promoter P67A

<400> SEQUENCE: 20
ctgctgaatc aagaacaacc ctaggtgcac ctgtccccat agagtccca    49

<210> SEQ ID NO 21

```
<211> LENGTH: 19
<212> TYPE: DNA
<213> ORGANISM: Artificial Sequence
<220> FEATURE:
<223> OTHER INFORMATION: Forward single chain oligonucleotide designed
      to form a linker with NCoI and BglII overhang

<400> SEQUENCE: 21
gatggtcgaa actccagta                                                    19

<210> SEQ ID NO 22
<211> LENGTH: 19
<212> TYPE: DNA
<213> ORGANISM: Artificial Sequence
<220> FEATURE:
<223> OTHER INFORMATION: Reverse single chain oligonucleotide designed
      to form a linker with NCoI and BglII overhang

<400> SEQUENCE: 22
cagctttgag gtcatcatg                                                    19

<210> SEQ ID NO 23
<211> LENGTH: 7
<212> TYPE: PRT
<213> ORGANISM: Artificial Sequence
<220> FEATURE:
<223> OTHER INFORMATION: vacuole targeting signal

<400> SEQUENCE: 23

Gly Leu Leu Val Asp Thr Met
1               5

<210> SEQ ID NO 24
<211> LENGTH: 1899
<212> TYPE: DNA
<213> ORGANISM: Erwinia rhapontici
<220> FEATURE:
<221> NAME/KEY: misc_feature
<222> LOCATION: 707, 1347
<223> OTHER INFORMATION: n = A,T,C,G or other unknown

<400> SEQUENCE: 24
atgtcctctc aagaattgaa agcggctgtc gctattttc ttgcaaccac ttttctgcc          60 acatcctatc aggcctgcag tgccgggcca gataccgccc cctcactcac cgttcagcaa       120
tcaaatgccc tgcccacatg gtggaagcag gctgtttttt atcaggtata tccacgctca       180
tttaaagata cgaatgggga tgcattgggg gatttaaacg gtattattga gaatttagac       240
tatctgaaga aactgggtat tgatgcgatt tggatcaatc acattacga ttcgccgaat        300 acggataatg gttatgacat ccgggattac cgtaagataa tgaaagaata cggtacgatg      360
gaagactttg accgtcttat ttcagaaatg aagaaacgca atatgcgttt gatgattgat       420
attgttatca accacaccag cgatcagcat gcgtggtttg ttcagagcaa atcgggtaag       480
aacaacccct acagggacta ttacttctgg cgtgacggta aggatggcca tgcccccaat       540
aactatccct ccttcttcgg tggctcagcc tgggaaaaag acgataaatc aggccagtat       600
tacctccatt actttgccaa acagcaaccc gacctcaact gggacaatcc caaagtccgt       660
caagacctgt atgacatgct ccgcttctgg ttagataaag cgtttntgg tttacgcttt       720 gataccgttg ccacctattc aaaaatcccg aacttccctg accttagcca acagcagtta       780
aaaaatttcg ccgaggaata tactaaaggt cctaaaattc acgactacgt gaatgaaatg       840
aacagagaag tattatccca ctatgatatc gccactgcgg gggaaatatt tgggggttcct       900
```

```
ctggataaat cgattaagtt tttcgatcgc cgtagaaatg aattaaatat agcgtttacg    960
tttgatctga tcagactcga tcgtgatgct gatgaaagat ggcggcgaaa agactggacc   1020
ctttcgcagt tccgaaaaat tgtcgataag gttgaccaaa cggcaggaga gtatgggtgg   1080
aatgcctttt tcttagacaa tcacgacaat ccccgcgcgg tttctcactt tggtgatgat   1140
cgaccacaat ggcgcgagca tgcggcgaaa gcactggcaa cattgacgct gacccagcgt   1200
gcaacgccgt ttatctatca gggttcagaa ctcggtatga ccaattatcc ctttaaaaaa   1260
atcgatgatt tcgatgatgt agaggtgaaa ggttttggc aagactacgt tgaaacaggc    1320
aaagtgaaag ctgaggaatt ccttcanaac gtacgccaaa ccagccgtga taacagcaga   1380 accccttcc agtgggatgc aagcaaaaat gcgggcttta ccagcggaac cccttggtta    1440
aaaatcaatc ccaattataa agaaatcaac agcgcagatc agattaacaa tccaaattcc   1500
gtatttaact attatagaaa gctcattaac attcgccacg catccctgc cttaacctac     1560 ggcagttata ttgatttagc tcctgacaac aattcagtct atgcttacac tcgaacgttt   1620
ggcgctgaaa aatatcttgt ggtcattaat tttaaagaag aagtgatgca ctacaccctg   1680
cctggggatt tatccatcaa taaggtgatt actgaaaaca acagtcacac tattgtgaat   1740
aaaaatgacg tagaagatcc tcgtgggggct acaagcgttt gtagccccctt ccaggctcaa   1800 aaaaggcctg cgacccggg ttactctgct gcccattcga ttcggttctt gccccggttt    1860
ttcgcttcat acaggggcga catccacgcg tttaagtaa                          1899

<210> SEQ ID NO 25
<211> LENGTH: 1797
<212> TYPE: DNA
<213> ORGANISM: Unknown
<220> FEATURE:
<223> OTHER INFORMATION: Bacterial isolate 68J
<220> FEATURE:
<221> NAME/KEY: misc_feature
<222> LOCATION: 1478
<223> OTHER INFORMATION: n = A,T,C,G or other unknown

<400> SEQUENCE: 25
atgtttctta atggatttaa gacagttatt gctctgacta tggcaagctc gtttatctt     60 gccgccagcc cgttaactaa gccatcgacc cctattgccg caacgaatat acaaaagtcc   120
gctgattttc ccatttggtg gaaacaggca gtattttacc agatttatcc ccgctcattt   180
aaagatagca atggtgatgg tatcggcgat attcccggta tcattgagaa actggactat   240
ttaaaaatgc tgggagttga tgctatctgg ataaacccgc actatgagtc tcctaacacc   300
gacaatggtt acgatattag tgattatcgt aaaatcatga aggagtacgg cagcatggct   360
gactttgacc gtctggttgc cgaaatgaat aaacgtggta tgcgcctgat gattgatatt   420
gttatcaatc ataccagcga tcgtcaccgc tggtttgtgc agagccgttc aggtaaagat   480
aatccttacc gcgactatta ttttctggcgt gatggtaaac agggacaggc tcccaataac   540
tatccctctt tctttggcgg ttcagcctgg caactggata acagactga ccagtattat    600 ctgcactatt ttgcaccaca gcagccggat ctgaactggg ataacccaaa agttcgggct   660
gaactctacg atattctgcg tttctggctg gataaaggcg tatccggact acgttttgat   720
accgtggcta ctttctccaa aattcctggc ttccccgacc tgtcaaaagc gcagctgaag   780
aattttgccg aagcttatac tgaggggccg aatattcata atatatcca tgaaatgaac   840 cgccaggtac tgtctaaata taatgttgcc accgctggtg aaatcttcgg tgtgccagtg   900
agtgctatgc cggattattt tgaccggcgg cgtgaagaac tcaatattgc tttcaccttt   960
```

-continued

```
gatttgatca ggctcgatcg ttatcccgat cagcgctggc gtcgtaaacc atggacatta      1020
agccagtttc gtcaagttat ctctcagact gaccgtgccg ccggtgaatt tggctggaac      1080 gccttttttcc ttgataacca tgataacccg cgccaggtct cacactttgg tgacgacagc     1140
ccacaatggc gcgaacgctc ggcaaaagca ctggcaacgc tgctgctgac gcagcgtgcc     1200
acgccgttta tctttcaggg ggcggagttg gaatgactac attacccctt taaaaatata      1260
gaggaatttg atgatattga ggttaaaggc ttctggaacg actatgtagc cagcggaaaa      1320
gtaaacgctg ctgaatttt acaggaggtt cgcatgacca ccgcgataa cagccgaaca      1380 ccaatgcagt ggaacgactc tgttaatgcc ggattcaccc agggcaaacc ctggtttcac      1440
ctcaatccca actataagca aatcaatgcc gccagggngg tgaataaacc cgactcggta     1500
ttcagttact accgtcaact gatcaacctg cgtcaccaga tcccggcact gaccagtggt      1560
gaataccgtg atctcgatcc gcagaataac caggtctatg cctatacccg tatactggat     1620
aatgaaaaat atctggtggt agttaatttt aaacctgagc agctgcatta cgctctgcca      1680
gataatctga ctattgccag cagtctgctg gaaaatgtcc accaaccatc actgcaagaa     1740
aatgcctcca cgctgactct tgctccgtgg caagccggga tctataagct gaactga       1797
```

<210> SEQ ID NO 26
<211> LENGTH: 1794
<212> TYPE: DNA
<213> ORGANISM: Klebsiella sp.

<400> SEQUENCE: 26

```
atgtcttttg ttacgctacg taccggggtg gctgtcgcgc tgtcatcttt gataataagt       60
ctggcctgcc cggctgtcag tgctgcacca tccttgaatc aggatattca cgttcaaaag      120
gaaagtgaat atcctgcatg gtggaaagaa gctgtttttt atcagatcta tcctcgctca     180
tttaaagaca ccaatgatga tggcattggc gatattcgcg gtattattga aaagctggac     240
tatctgaaat cgctcggtat tgacgctatc tggatcaatc cccattacga ctctccgaac     300
accgataacg gctatgacat cagtaattat cgtcagataa tgaaagagta tggcacaatg     360
gaggattttg atagccttgt tgccgaaatg aaaaaacgaa atatgcgctt aatgatcgac     420
gtggtcatta accataccag tgatcaacac ccgtggttta ttcagagtaa aagcgataaa     480 aacaacccctt atcgtgacta ttatttctgg cgtgacggaa agataatca gccacctaat     540 aattacccct catttttcgg cggctcggca tggcaaaaag atgcaaagtc aggacagtac     600
tatttacact attttgccag acagcaacct gatctcaact gggataaccc gaaagtacgt     660
gaggatcttt acgcaatgct ccgcttctgg ctggataaag gcgtttcagg catgcgattt     720
gatacggtgg caacttattc caaaatcccg ggatttccca atctgacacc tgaacaacag     780
aaaaattttg ctgaacaata caccatgggd cctaatattc atcgatacat tcaggaaatg     840
aaccggaaag ttctgtcccg gtatgatgtg ccaccgcgg gtgaaatttt tggcgtcccg     900
ctggatcgtt cgtcgcagtt ttttgatcgc cgccgacatg agctgaatat ggcgtttatg     960
tttgacctca ttcgtctcga tcgcgacagc aatgaacgct ggcgtcacaa gtcgtggtcg    1020
ctctctcagt tccgccagat catcagcaaa atggatgtca cggtcggaaa gtatggctgg    1080
aacacgttct tcttagacaa ccatgacaac ccccgtgcgg tatctcactt cggggatgac    1140
aggccgcaat ggcgggaggc gtcggctaag gcactggcga cgattaccct cactcagcgg    1200
gcgacgccgt ttatttatca gggttcagag ctgggaatga ctaattatcc cttcaggcaa    1260
```

```
ctcaacgaat ttgacgacat cgaggtcaaa ggtttctggc aggattatgt ccagagtgga    1320
aaagtcacgg ccacagagtt tctcgataat gtgcgcctga cgagccgcga taacagcaga    1380
acacctttcc agtggaatga caccctgaat gctggtttta ctcgcggaaa gccgtggttt    1440
cacatcaacc caaactatgt ggagatcaac sccgaacgcg aagaaacccg cgaagattca    1500
gtgctgaatt actataaaaa aatgattcag ctacgccacc atatccctgc tctggtatat    1560
ggcgcctatc aggatcttaa tccacaggac aataccgttt atgcctatac ccgaacgctg    1620
ggtaacgagc gttatctggt cgtggtgaac tttaaggagt acccggtccg ctatactctc    1680
ccggctaatg atgccatcga ggaagtggtc attgatactc agcagcaagg tgcgccgcac    1740
agcacatccc tgtcattgag cccctggcag gcaggtgcgt ataagctgcg gtaa          1794
```

METHOD FOR INCREASING PRODUCT YIELD

STATEMENT REGARDING SEQUENCE LISTING

The Sequence Listing associated with this application is provided in text format in lieu of a paper copy, and is hereby incorporated by reference into the specification. The name of the text file containing the Sequence Listing is 900145_401_SEQUENCE_LISTING.txt. The text file is 14 KB, was created on Jun. 3, 2009, and is being submitted electronically via EFS-Web.

CROSS-REFERENCE TO RELATED APPLICATION

This application claims the benefit of Australian Patent Application No. 2003902253, filed May 12, 2003.

BACKGROUND OF THE INVENTION

1. Field of the Invention

This invention relates generally to methods for increasing the yield of a compound produced by an organism. More particularly, the present invention relates to methods for increasing the total or soluble carbohydrate content or sweetness or increasing the content of an endogenous carbohydrate of a plant tissue by producing a sugar-metabolizing enzyme that catalyzes the conversion of an endogenous sugar (one that is normally produced in the plant) to an alien sugar (one that is not normally produced in the plant at the same developmental stage). The invention also relates to plants and plant parts that produce a sugar-metabolizing enzyme to yield an alien sugar, with the consequence of higher total fermentable carbohydrate content, and to fermentable carbohydrates and other products derived therefrom.

Bibliographic details of the publications referred to in this specification are collected at the end of the description.

2. Description of the Related Art

Plants are the primary source of renewable bioenergy, biomaterials and feedstocks for industrial biotransformations. The yield and concentration of desired sugars in plants are key determinants of the technical and economic feasibility of downstream industrial processes. However, the metabolic networks of plants for biosynthesis of sugars show substantial internal buffering and redundancy, with the consequence that alteration to a key gene in metabolism of a sugar commonly results in no useful change to the harvestable yield of the sugar (Moore, 1995; Nguyen-Quoc and Foyer, 2001; Fernie et al., 2002). For example, Botha et al. (2001) have shown that 70% reduction in activity of a key enzyme in sucrose breakdown (acid invertase) results in no significant change in sucrose yield or purity in transgenic sugarcane.

Sucrose isomerases are enzymes produced by organisms including various microbes, with the capability to convert the disaccharide sucrose into isomers such as isomaltulose (palatinose) or trehalulose. Sucrose isomerases vary in their properties including the disaccharide reaction products, the proportion of monosaccharides such as glucose and fructose in the reaction products, the kinetic properties of the enzymes, the optimal reaction conditions, and the sensitivity of the enzyme to variations from the optimal conditions (Veronese and Perlot, 1999).

Sucrose is the major intermediary in carbon flux between source (photosynthetic) tissues and sink (growth and storage) tissues within plants, and it is the primary storage product in certain plants such as sugarcane and sugarbeet. Several reports indicate that expression of introduced sucrose isomerase genes in plants can result in the conversion of sucrose to an isomer such as isomaltulose, and it has been envisaged that this conversion could be beneficial for the industrial production of the isomer. The emphasis has been towards the high-level or complete conversion of sucrose to the isomer as a desired industrial product (Birch and Wu, 2002; Börnke et al., 2002b), or as a precursor for in planta conversion to derived industrial materials (Kunz et al., 2002).

It has also been envisaged that the conversion could be lethal to plant cells by conversion of an essential carbon and energy reserve to an unavailable form, with applications in cell ablation for purposes such as engineered male sterility (Bornke and Sonnewald, 2001). Indeed, several reports indicate that sucrose isomerase transgene expression is harmful to plant development and yield, causing severe growth abnormalities, reduced starch content, and reduced soluble carbohydrate content (Börnke et al., 2002a, b).

In tobacco, there were severe and damaging effects on plant development due to constitutive expression from the CaMV35S promoter of a sucrose isomerase gene fused to the potato proteinase inhibitor II signal peptide to direct the sucrose isomerase enzyme to the extracellular (apoplasmic) space. Low isomaltulose levels (0.3 to 0.6 mM m$^{-2}$ of leaf tissue) were detected, equivalent to about 20% to 44% of the normal carbohydrate levels in leaf starch or 10 to 45 times the normal low transitory sucrose levels in this source tissue. Effects on stored carbohydrates in sink tissues were not reported. Growth of leaves and other organs was severely disrupted, and the plants were unable to reproduce (Börnke et al., 2002a).

In potato, expression of the same apoplasm-targeted sucrose isomerase from the tuber-specific patatin B33 promoter resulted in plants without apparent adverse effects on growth and development. Isomaltulose yields were again low (10-15 μmol g$^{-1}$ fresh weight of tuber tissue, equivalent to about 4% to 5% of the normal stored carbohydrate levels in tuber starch), and slightly below the usual sucrose levels in this starch-storing sink tissue. Furthermore, because of accompanying decreases in contents of sucrose, hexoses and starch, yields of total soluble carbohydrate (excluding starch) and total fermentable carbohydrate (including starch) were decreased in the modified lines (Börnke et al., 2002b).

To overcome these problems, the present inventors conceived a novel approach based upon combining (i) a sucrose isomerase enzyme, especially a highly efficient sucrose isomerase such as UQ68J; (ii) use of a plant species such as sugarcane that accumulates sucrose as the stored carbohydrate; and (iii) targeting the introduced sucrose isomerase to the sucrose storage compartment, for example the large vacuole of sucrose storage parenchyma within the mature culm in the case of sugarcane. Because isomaltulose is not metabolized in plants, the present inventors hypothesized that, in contrast to sucrose, it might not be subject to 'futile cycles' of degradation and synthesis in the mature storage tissues, which have the potential to decrease storage efficiency and harvestable yield. Therefore, the inventors' approach was designed to achieve higher yields of soluble carbohydrates and fermentable carbohydrates in the modified plants, in contrast with the reduction of these yields reported from previous approaches. Consistent with this hypothesis, it was found that isomaltulose concentrations above 500 mM in juice can be achieved in sugarcane, by expressing a sucrose isomerase (e.g., the highly efficient sucrose isomerase UQ68J), targeted to the sucrose storage vacuoles in mature stem parenchyma. This exceeds the total stored carbohydrate content obtained from unmodified sugarcane, and it may be accomplished without commensurable reduction in the content of endogenous sugars, resulting in a much higher total soluble sugar content in the modified lines.

Plants have highly adapted sensors and transporters for sucrose, but it is generally considered that these sucrose sensors and transporters are not able to respond in the same way to isomers such as isomaltulose (Loreti et al., 2000; Sinha et al., 2002). In stark contrast with sucrose, plants are unable to metabolize some isomers such as isomaltulose as a source of carbon and energy (Sinha et al., 2002). Nevertheless, the isomers can elicit changes in the patterns of cellular gene expression and modify the activities of certain enzymes involved in sucrose metabolism or in signal-transduction cascades in plants (Fernie et al., 2001; Sinha et al., 2002).

Because exogenous supply of isomaltulose to tissue slices from potato tubers altered the metabolism of other exogenously supplied sugars, Fernie et al. (2001) suggested that supplying isomaltulose to potato tubers represents a novel way to increase starch synthesis. However, the exogenous supply of a substance like isomaltulose to plant organs such as potato tubers is unlikely to be practical for industrial use, and there is no report that this approach has been tested or applied to enhance starch yield. In studies by Börnke et al. (2002b), transgenic potato plants expressing an apoplasmic sucrose isomerase gene from a tuber-specific promoter accumulated isomaltulose to a level approaching the usual sucrose content in tubers, but showed decreased yield of starch and of total soluble sugars.

Based on consideration of the differential capacity of plants to sense sucrose versus related compounds such as isomaltulose, the present inventors conceived another approach to achieve increased yields of endogenous sugars in plants by appropriate expression of an introduced sucrose isomerase. This contrasts with the intent of previously explored strategies (to produce plants for the harvest of isomaltulose or derivatives of isomaltulose), and with their outcome (plants with reduced yields of endogenous carbohydrates). Because the signaling and control mechanisms that operate on plant metabolism are incompletely understood, the present inventors undertook substantial experimentation to determine a scope of conditions yielding their desired industrial outcome (plants with increased yields of endogenous carbohydrates). In this regard, it was found that total soluble sugar contents in the range of 700-900 mM sucrose equivalents in juice can be achieved in sugarcane lines engineered for low-level expression of a sucrose isomerase directed to the cytosolic compartment, or divided between compartments. This is approximately twice the total stored carbohydrate content typically obtained from unmodified sugarcane, and it may be accomplished with little change to the harvested sugar composition. The approach is not limited to the sucrose isomerase gene, the isomaltulose conversion product, or the sugarcane plant used by way of example. It encompasses more broadly the expression within an organism of an introduced gene resulting in the partial conversion of a substrate endogenous compound that is normally sensed by the organism into a product compound that is not perceived in an equivalent manner within the organism, with the effect that metabolic flows are altered, resulting in the accumulation of higher yields of desired endogenous compounds.

BRIEF SUMMARY OF THE INVENTION

The present invention is predicated in part on the discovery that an appropriate expression pattern of a gene within a plant, resulting in partial conversion of an endogenous sugar into a sugar that is not normally produced in the plant at the same developmental stage, alters the source-sink signaling and leads to an increase in the content of total soluble carbohydrates including sugars in the plant. This discovery has been reduced to practice in methods for modifying the total carbohydrate content or sweetness of plant sink tissues, in genetically modified plants whose sink tissues have a higher total or soluble carbohydrate content or sweetness than sink tissue of unmodified plants, and in products derived from such genetically modified plants.

Accordingly, in one aspect of the present invention, methods are provided for modifying the total soluble carbohydrate content or sweetness of a sink tissue of a plant. These methods generally comprise producing in cells of the plant, a sugar-metabolizing enzyme that catalyzes the conversion of an endogenous sugar of the plant to an alien sugar that is not normally produced in the plant at the same developmental stage, whereby the sugar-metabolizing enzyme is produced at a level or functional activity so that the total carbohydrate content or sweetness of the sink tissue is increased as compared to that of the corresponding sink tissue of a plant that does not produce the enzyme. In some embodiments, the sugar-metabolizing enzyme is produced in the plant cells by expression of a polynucleotide that encodes the enzyme. In these embodiments, the plant is a transgenic plant that is selected from a plurality of transgenic plants which comprise in their nucleome the enzyme-encoding polynucleotide operably connected to a transcriptional control element. The transgenic plant is selected on the basis that it produces the sugar-metabolizing enzyme at a level or functional activity so that the total or soluble carbohydrate content or sweetness of the sink tissue of the selected transgenic plant is increased as compared to that of the corresponding sink tissue of the control plant. Suitably, the polynucleotide is operably connected to a transcriptional control element that is operable in the plant cells. In some embodiments, the enzyme-encoding polynucleotide is constitutively expressed, and the transcriptional control element is, therefore, a constitutive promoter. In other embodiments, the enzyme-encoding polynucleotide is selectively expressed, including coordination of timing, tissue specific expression and subcellular localization. In these latter embodiments, the transcriptional control element is selected from a tissue-specific promoter, a developmentally regulated promoter or an inducible promoter.

In some embodiments, the total carbohydrate content or sweetness of the sink tissue is increased by producing the sugar-metabolizing enzyme in the plant cells at a level or functional activity that results in partial conversion, which is generally less than about 20% but typically less than about 15% and more usually less than about 10% conversion, of the endogenous sugar to the alien sugar. Suitably, this partial conversion occurs within tissues undergoing cell division and/or cell expansion contributing to plant growth. In these embodiments, the sugar-metabolizing enzyme is suitably active in the cytosol of the plant cells, or its activity may be distributed between the cytosol and sub-cellular compartments involved in sugar storage and/or transport. Suitably, in these embodiments, the alien sugar is accumulated without commensurable reduction in the content of endogenous sugars or carbohydrates.

In other embodiments, the total carbohydrate content or sweetness of the sink tissue is increased by targeting the sugar-metabolizing enzyme to a sub-cellular compartment of the plant cells, which is used for sugar storage. In these embodiments, the sugar-metabolizing enzyme is suitably present in the sub-cellular compartment at a level or functional activity that results in substantial conversion, which is generally at least about 20% but typically at least about 40% and more usually at least about 60% conversion, of the endogenous sugar to the alien sugar. Suitably this substantial conversion occurs within tissues that have substantially ceased cell division and cell expansion and that are functional for carbohydrate storage. Desirably, the substantial conversion does not occur within tissues undergoing cell division and/or cell expansion contributing to plant growth. The sub-cellular compartment is suitably a compartment that stores sugar, typically the vacuole or the vacuole and the apoplasmic space. Suitably, in these embodiments, the alien sugar is accumulated without commensurable reduction in the content of endogenous sugars or carbohydrates.

Typically, the plant cells that function as carbon sinks include cells in non-photosynthetic tissues or organs and storage tissues or organs, such as roots, tubers, culms, fruits or seeds as well as non photosynthetic cells of source organs such leaves. Accordingly, the plant is typically a plant whose sink tissues have economic value affected by sugar content. Such plants include species which produce vegetables and fruit of commercial importance, as well as species which are harvested for the extraction of sucrose and other sugars, including sugarcane and sugar beet.

The endogenous sugar and alien sugars are suitably selected from monosaccharides, oligosaccharides, and sugar derivatives including sugar alcohols, sugar acids, amino sugars and other variants such as deoxy sugars, methyl sugars and the like. In one embodiment, the endogenous sugar is sucrose and the alien sugar is selected from isomaltulose and trehalulose. In this embodiment, the sugar-metabolizing enzyme is typically a sucrose isomerase.

In a related aspect, the invention provides methods of producing a plant having sink tissue which has an increased content of an endogenous carbohydrate as compared to a corresponding sink tissue of a control plant. These methods generally comprise selecting a transgenic plant with the desired endogenous carbohydrate content from a plurality of transgenic plants which comprise in their nucleome a polynucleotide that is operably connected to a transcriptional control element and that encodes a sugar-metabolizing enzyme that catalyzes the conversion of an endogenous sugar of the plant to an alien sugar. The transgenic plant is selected on the basis that it produces the sugar-metabolizing enzyme at a level or functional activity so that the content of the endogenous carbohydrate of the sink tissue of the transgenic plant is increased as compared to that of the corresponding sink tissue of the control plant.

In another aspect, the invention provides a transgenic plant cell which has an increased total carbohydrate content or an increased content of an endogenous carbohydrate as compared to a control plant cell, as defined herein. The nucleome of the transgenic plant cell comprises a transcriptional control element operably connected to a polynucleotide that encodes a sugar-metabolizing enzyme. The sugar-metabolizing enzyme catalyzes the conversion of an endogenous sugar of the plant cell to an alien sugar. Advantageously, the sugar-metabolizing enzyme is produced at a level or functional activity so that the total carbohydrate content or the content of the endogenous carbohydrate of the transgenic plant cell is increased as compared to that of the control plant cell.

In yet another aspect, the invention provides a transgenic plant having a sink tissue which has an increased total carbohydrate content or sweetness or an increased content of an endogenous carbohydrate as compared to a corresponding sink tissue of a control plant as defined herein. The transgenic plant comprises cells which comprise in their nucleome a polynucleotide that encodes a sugar-metabolizing enzyme catalyzing the conversion of an endogenous sugar of the plant to an alien sugar. For expression, the polynucleotide is operably connected to a transcriptional control element that is functional in the plant cells. In one embodiment, the sugar-metabolizing enzyme is produced at a level or functional activity so that the total carbohydrate content or sweetness or the content of the endogenous carbohydrate of the sink tissue of the transgenic plant is increased as compared to that of the corresponding sink tissue of the control plant.

In still another aspect, the invention provides a transgenic plant sink tissue which has an increased total carbohydrate content or sweetness or an increased content of an endogenous carbohydrate as compared to control plant sink tissue as defined herein. The transgenic plant sink tissue comprises cells which comprise in their nucleome a polynucleotide that encodes a sugar-metabolizing enzyme catalyzing the conversion of an endogenous sugar of the plant to an alien sugar. For expression, the polynucleotide is operably connected to a transcriptional control element that is functional in at least some of the plant cells. In one embodiment, the sugar-metabolizing enzyme is produced in source and/or sink tissues of the plant at a level or functional activity so that the total carbohydrate content or sweetness or the content of the endogenous carbohydrate of the transgenic sink tissue is increased as compared to that of the control plant sink tissue. Suitably, the sink tissue is selected from fruit, seeds, culms, tubers and roots.

Still another aspect of the invention provides total carbohydrates or endogenous carbohydrates harvested from a plant or sink tissue as broadly described above. In one embodiment, the carbohydrates are selected from simple sugars including sucrose, glucose and fructose.

In a further aspect of the invention, there is provided a process of producing a product by fermentation, which generally comprises fermenting carbohydrates, which are substrates for fermentation and which are harvested from a plant or sink tissue as broadly described above. The fermentation product produced by this process suitably comprises one or more of ethanol, acetic acid, lactic acid, carbon dioxide, or other products produced by fermentation upon substrates comprising carbohydrates harvested from a plant or sink tissue as broadly described above.

In another aspect, the present invention provides methods for producing in a plant an alien sugar that is not endogenously produced in the plant at the same developmental stage as an endogenous sugar. These methods generally comprise comprising delivering to a sub-cellular compartment used for sugar storage in cells of the plant a sugar-metabolizing enzyme that catalyzes the conversion of the endogenous sugar to the alien sugar. In some embodiments, the sub-cellular compartment is selected from the vacuole or apoplasmic space. Advantageously, the sugar-metabolizing enzyme is delivered to the sub-cellular compartments at a level or functional activity that results in a substantial increase in total sugar content, which is generally at least about 10% but preferably at least about 50% and more preferably at least about 100% above the endogenous sugar content of a corresponding unmodified plant. Suitably, the alien sugar is accumulated without commensurable reduction in the content of endogenous sugars or carbohydrates.

In yet another aspect, the invention provides a transgenic plant cell that comprises an alien sugar as defined herein. The nucleome of the transgenic plant cell comprises a transcriptional control element operably connected to a polynucleotide that encodes a sugar-metabolizing enzyme, which catalyzes the conversion of an endogenous sugar of the plant cell to the alien sugar. The sugar-metabolizing enzyme comprises a targeting signal that targets the enzyme to a sub-cellular compartment used for sugar storage in the plant cell, resulting in accumulation of the alien sugar with less than commensurable reduction in endogenous plant carbohydrates.

In still another aspect, the invention provides a transgenic plant having a sink tissue that comprises an alien sugar as defined herein. The transgenic plant comprises cells which comprise in their nucleome a polynucleotide that encodes a sugar-metabolizing enzyme catalyzing the conversion of an endogenous sugar of the plant to the alien sugar and that is operably connected to a transcriptional control element that is functional in the plant cells. The sugar-metabolizing enzyme comprises a targeting signal that targets the enzyme to a sub-cellular compartment used for sugar storage in cells of the plant, resulting in accumulation of the alien sugar with less than commensurable reduction in endogenous plant carbohydrates.

In still another aspect, the invention provides a transgenic plant sink tissue that comprises an alien sugar as defined herein. The transgenic plant sink tissue comprises cells which comprise in their nucleome a polynucleotide that encodes a sugar-metabolizing enzyme catalyzing the conversion of an endogenous sugar of the plant to an alien sugar and that is operably connected to a transcriptional control element that is functional in at least some of the plant cells. The sugar-metabolizing enzyme comprises a targeting signal that targets the enzyme to a sub-cellular compartment used for sugar storage in cells of the sink tissue, resulting in accumulation of the alien sugar with less than commensurable reduction in endogenous plant carbohydrates. Suitably, the sink tissue is selected from fruit, seeds, culms, tubers and roots.

In still another aspect, the present invention provides methods for the producing isomaltulose. These methods generally comprise expressing in a plant that normally accumulates sucrose as a storage reserve, an introduced polynucleotide that encodes the sucrose isomerase UQ68J, which is optionally modified to confer sucrose isomerase activity selectively in the sucrose storage compartment. The plant is suitably selected from sugarcane, sorghum or sugarbeet. Suitably, the sucrose storage compartment is selected from the sucrose storage vacuole, or the vacuole and the extracellular space. In some embodiments, the expression of the polynucleotide occurs preferentially in the mature sucrose storage tissues, comprising the culm of the plant. In some embodiments, the methods further comprise harvesting the isomaltulose from the plant.

The demonstration that expression within an organism of an introduced gene resulting in the partial conversion of a substrate endogenous compound that is normally sensed by the organism into a product compound that is not perceived in an equivalent manner within the organism can alter metabolic flows, resulting in the accumulation of higher yields of desired endogenous compounds is highly novel and unexpected and has wide industrial utility beyond the sucrose isomerase gene, the isomaltulose conversion product, carbohydrate endogenous compounds or the sugarcane plant provided here by way of detailed examples. Accordingly, the present invention broadly encompasses the expression within an organism of an introduced gene resulting in the partial conversion of a substrate endogenous compound that is normally sensed by the organism into a product compound that is not perceived in an equivalent manner within the organism, with the effect that metabolic flows are altered, resulting in the accumulation of higher yields of desired endogenous compounds. The product compound is suitably not metabolized by the organism. Typically, the product compound is an isomer of the substrate compound that is normally sensed by the organism. In some embodiments, the introduced gene product is distributed between the metabolically active cytosolic compartment and the metabolite storage compartments. In these embodiments, the metabolite storage compartment is advantageously selected from the vacuole or the vacuole and the extracellular spaces. In some embodiments, the conversion activity is conferred selectively in storage tissues of the organism but not in the tissues undergoing active growth and expansion as a precursor to formation of the storage tissues. In some embodiments, the desired metabolites comprise the endogenous substrate compound.

The present inventors have also discovered a novel promoter whose sequence is set forth in SEQ ID NO:10, which can direct stem-specific gene expression in plants (e.g., monocotyledonous, especially graminaceous monocotyledonous plants such as sugarcane). This promoter confers a useful pattern of expression not obtained using previously tested promoters, and it differs structurally from those promoters in several elements, including absence of a region whose sequence is set forth in SEQ ID NO:20. Accordingly, the present invention provides in another aspect an isolated DNA molecule comprising a nucleotide sequence that corresponds or is complementary to the sequence set forth in SEQ ID NO:10 or to a biologically active portion thereof, or to a variant of these that displays at least about 93, 94, 95, 96, 97, 98, 99% sequence identity to the sequence set forth in SEQ ID NO:10. Desirably, the variant lacks SEQ ID NO:20 and hybridizes to the sequence set forth in SEQ ID NO:10 under at least medium stringency conditions.

Typically, the promoter of the present invention is fused to a coding sequence to create a chimeric construct for expressing the coding sequence in a plant of interest. The construct can then be introduced into a host plant cell or plant or plant part, by any method of choice. Thus, another aspect of the invention provides a chimeric DNA construct comprising the DNA molecule as broadly described above operably linked to a foreign or endogenous nucleic acid sequence to be transcribed. In some embodiments, the chimeric DNA construct further comprises a 3' non-translated sequence that is operably linked to the foreign or endogenous DNA sequence and that functions in plant cells to terminate transcription and/or to cause addition of a polyadenylated nucleotide sequence to the 3' end of a transcribed RNA sequence.

The foreign or endogenous DNA sequence is foreign or endogenous with respect to the plant cell in which it is or will be introduced. In some embodiments, the foreign or endogenous DNA sequence encodes a structural or regulatory protein, or alternatively, a transcript capable of modulating expression of a corresponding target gene. In some embodiments, the transcript comprises an antisense RNA or a ribozyme or other transcribed region aimed at downregulation of expression of the corresponding target gene. For example, the other transcribed region may comprise a sense transcript aimed at sense suppression (co-suppression) of the corresponding target gene.

In still another aspect, the invention contemplates a method for producing transformed plant cells, comprising introducing into regenerable plant cells a chimeric DNA construct as broadly described above so as to yield transformed plant cells and identifying or selecting transformed plant cells. In a related aspect, the present invention provides a transformed plant cell containing a chimeric DNA construct as broadly described above.

In yet another aspect, the invention provides a method for selecting stable genetic transformants from transformed plant cells, comprising introducing into regenerable plant cells a chimeric DNA construct as broadly described above so as to yield transformed plant cells and identifying or selecting a transformed plant cell line from the transformed plant cells. The regenerable cells may be regenerable dicotyledonous plant cells but are usually monocotyledonous plant cells such as regenerable graminaceous monocotyledonous plant cells. In some embodiments, the expression of the chimeric DNA construct in the transformed cells imparts a phenotypic characteristic to the transformed cells.

In still another aspect, the invention contemplates a method for producing a differentiated transgenic plant, comprising introducing a chimeric DNA construct as broadly described above into regenerable plant cells so as to yield regenerable transformed cells, identifying or selecting a population of transformed cells, and regenerating a differentiated transgenic plant from the population. In some embodiments, the expression of the chimeric DNA construct renders the differentiated transgenic plant identifiable over the corresponding non-transgenic plant. In a related aspect, the present invention provides a differentiated transgenic plant comprising plant cells containing a chimeric DNA construct as broadly described above. The chimeric DNA construct is transmitted through a complete cycle of the differentiated transgenic plant to its progeny so that it is expressed by the progeny plants. Thus, the invention also provides seed, other plant parts, tissue, and progeny plants derived from the differentiated transgenic plant.

FIGS. 16a-16d are a graphical representation showing isomaltulose concentrations in 'extracellular' and 'intracellular' fluid fractions from stem tissues of transgenic lines pU3ZERsN68J3.2His (a), pU3ZERsN68J1.17 (b), pU3ZERc68JC3.1 His (c), and pU3ZERsN68JC3.7His (d). The plants of a, b, d were 8 months old and c was 12 months old. Internode numbers for plants a, b, c and d were 35, 20, 43 and 30 respectively. Transgenic plant b was the second vegetative generation from stem cuttings; transgenic plants of a, c and d were the second vegetative generation as ratoon canes within the original pots. All of these lines were morphologically indistinguishable from the Q117 control.

FIGS. 17a-17d are a graphical representation showing concentrations of isomaltulose, other sugars (sum of glucose, fructose and sucrose as sucrose equivalents, i.e. G/2+F/2+S) and total sugars (sucrose equivalent) in stem tissues of the Q117 control (a) and transgenic lines pU3ZERsN68J3.2 #1 (b), pU3ZERsN68J3.2 #2 (c), and pU3ZERsN68J3.2His (d). All the plants were 8 months old, with 21, 27, 22 and 35 internodes respectively. The Q117 control was generated from stem cuttings. Transgenic plants b and c were the second vegetative generation from stem cuttings. Transgenic plant d was a second vegetative generation ratoon cane within the original pot. All of the transgenic lines were morphologically indistinguishable from the Q117 control.

FIGS. 18a-18d are a graphical representation showing concentrations of sucrose, other sugars (sum of glucose, fructose and isomaltulose as sucrose equivalents) and total sugar (sucrose equivalent) in stem tissues of the Q117 control (a) and transgenic lines pU3ZERsN68J1.17 #1 (b), pU3ZERsN68J1.17 #2 (c), and pU3ZERsN68J1.2 (d). All the plants were 8 months old with 21, 20, 30 and 31 internodes respectively. The Q117 control was generated from stem cuttings. Transgenic plant b was the second vegetative generation from stem cuttings. Transgenic plants c and d were the second vegetative generation as ratoon canes within the original pots. All of the transgenic lines were morphologically indistinguishable from the Q117 control.

FIGS. 19a-19d are a graphical representation showing concentrations of sucrose, other sugars (sum of glucose, fructose and isomaltulose as sucrose equivalents) and total sugar (sucrose equivalent) in stem tissues of the Q117 control (a) and transgenic lines pU3ZERc68JC1.3His (b), pU3ZERc68JC3.7His (c), and pU3ZERc68JC3.8His (d). All the plants were 8 months old with 28, 32, 38 and 30 internodes respectively. The Q117 control and transgenic plants b, c and d were the second vegetative generations from ratoon canes within the original pots. All of the transgenic lines were morphologically indistinguishable from the Q117 control.

Figure 20:
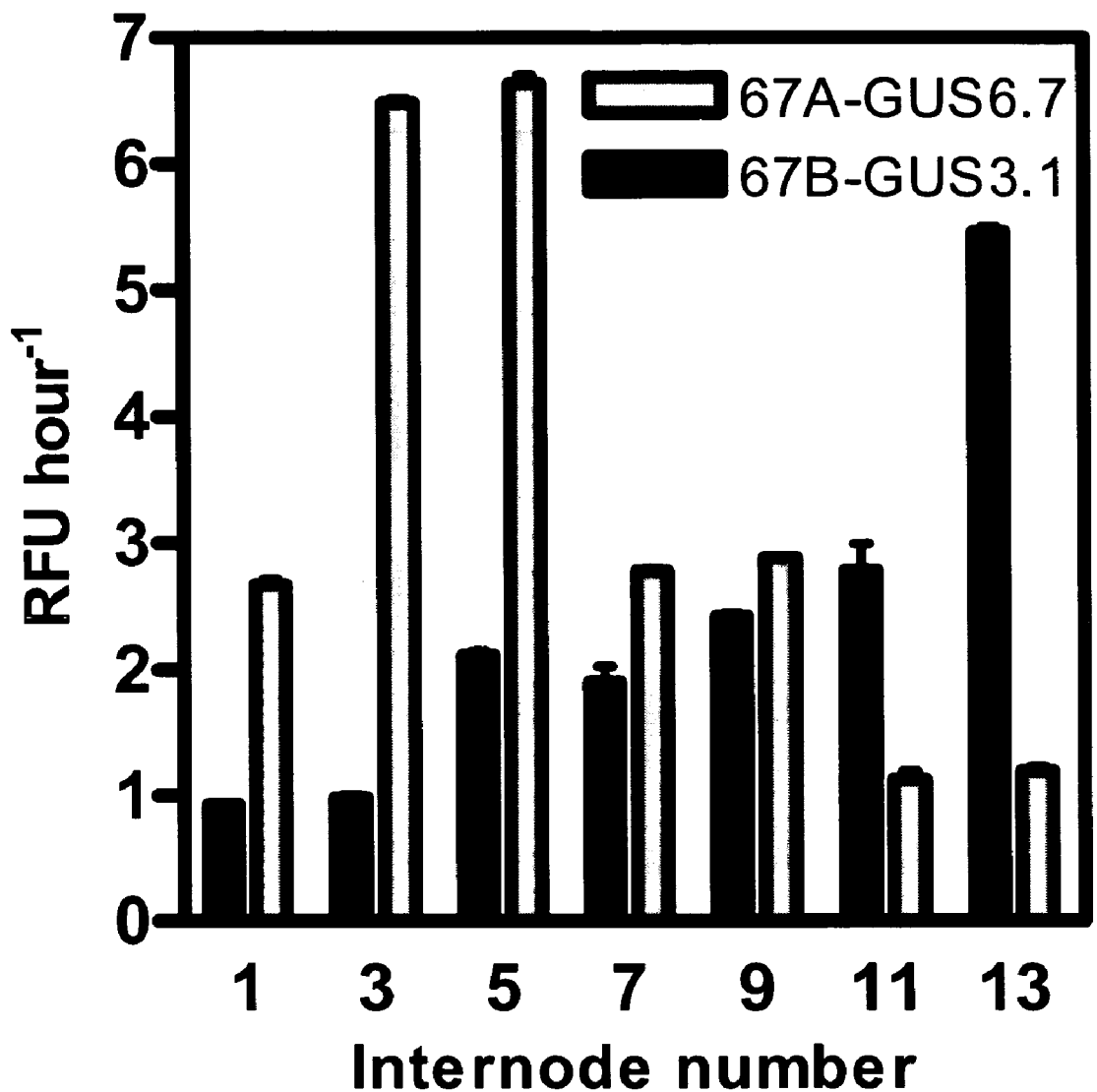

FIG. 20 is a graphical representation showing GUS activity levels in stem tissues of a transgenic line with promoter 67A (p67A-GUS6.7) and a transgenic line with promoter 67B (p67B-GUS3.1). Both lines were 6 months old with 14 internodes and generated from stem cuttings.

Figure 21:
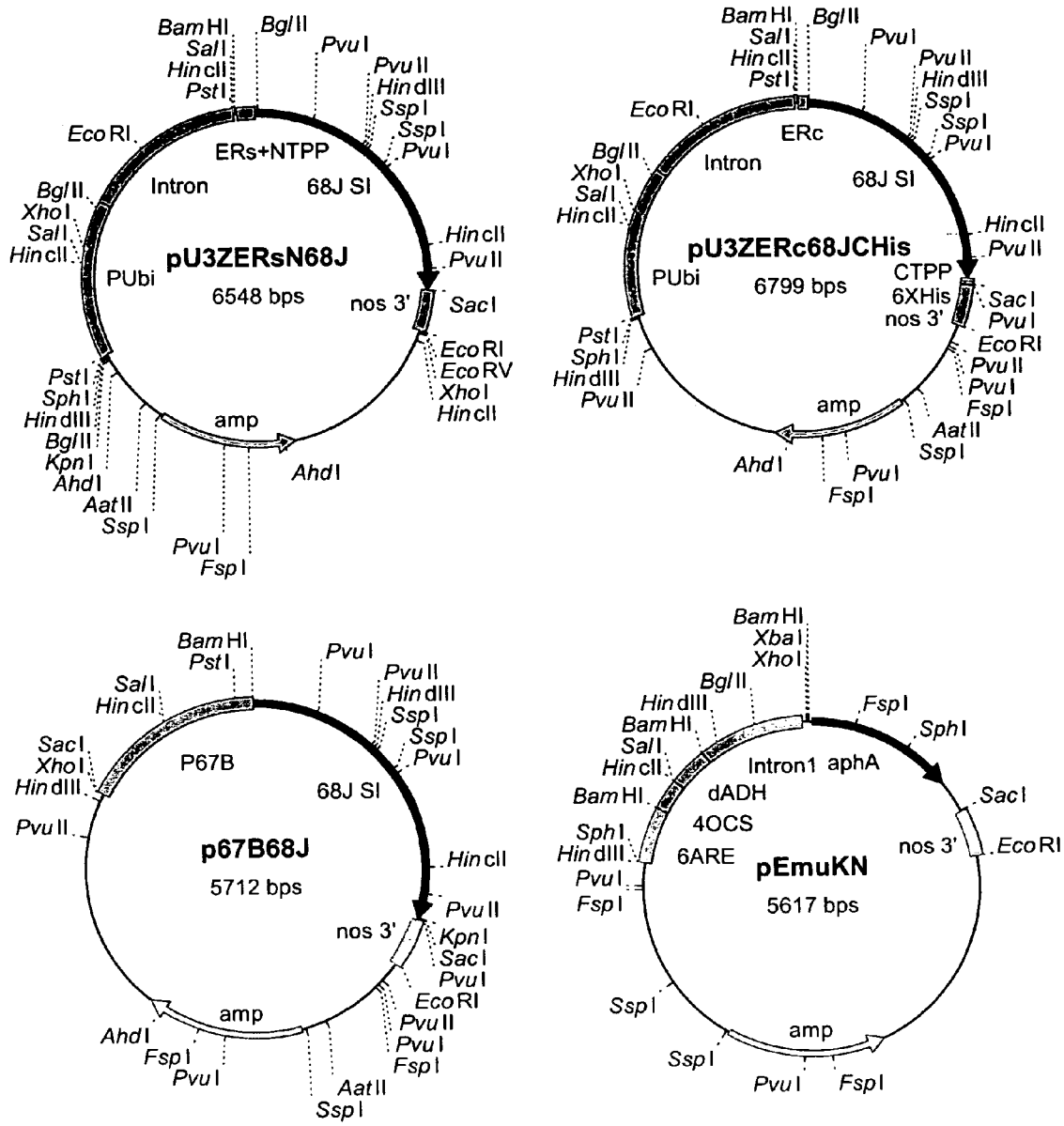

FIG. 21 is a graphical representation of the structure of illustrative 'direct gene transfer vectors' used to engineer a high total sugars phenotype in sugarcane.

TABLE A

Brief Description of the Sequences

| Sequence ID Number | Sequence | Length |
|---|---|---|
| SEQ ID NO: 1 | UQErw forward primer for cytosol-targeting | 35 bases |
| SEQ ID NO: 2 | UQ14S forward primer for cytosol-targeting | 35 bases |
| SEQ ID NO: 3 | UQ68J forward primer for cytosol-targeting | 34 bases |
| SEQ ID NO: 4 | UQErw reverse primer for cytosol-targeting | 28 bases |
| SEQ ID NO: 5 | UQ14S reverse primer for cytosol-targeting | 30 bases |
| SEQ ID NO: 6 | UQ68J reverse primer for cytosol-targeting | 30 bases |
| SEQ ID NO: 7 | DNA encoding modified ER signal and N-terminal propeptide (NTPP) from sweet potato sporamin | 111 bases |
| SEQ ID NO: 8 | DNA encoding modified ER signal from tobacco chitinase | 69 bases |
| SEQ ID NO: 9 | DNA encoding C-terminal propeptide (CTPP) from tobacco chitinase | 36 bases |
| SEQ ID NO: 10 | Promoter sequence P67B | 987 bases |
| SEQ ID NO: 11 | UQ68J forward primer for vacuole targeting (NTPP, or NTPP + CTPP constructs) | 31 bases |
| SEQ ID NO: 12 | UQ68J reverse primer for vacuole targeting (NTPP constructs) | 27 bases |
| SEQ ID NO: 13 | UQ68J reverse primer for vacuole targeting with 6 × His tag (NTPP constructs) | 45 bases |
| SEQ ID NO: 14 | UQ68J reverse primer for CTPP constructs | 45 bases |
| SEQ ID NO: 15 | UQ68J reverse primer for CTPP constructs with 6 × His tag | 63 bases |
| SEQ ID NO: 16 | Chitinase ER leader peptide forward primer | 24 bases |
| SEQ ID NO: 17 | Chitinase ER leader peptide reverse primer | 26 bases |
| SEQ ID NO: 18 | Promoter 67 forward primer | 23 bases |
| SEQ ID NO: 19 | Promoter 67 reverse primer | 29 bases |
| SEQ ID NO: 20 | Sequence of P67A not contained in P67B | 49 bases |

DETAILED DESCRIPTION OF THE INVENTION

Definitions

Unless defined otherwise, all technical and scientific terms used herein have the same meaning as commonly understood by those of ordinary skill in the art to which the invention pertains. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The term "about" is used herein to refer to a quantity, level, value, dimension, length, position, size, or amount that varies by as much as 30%, preferably by as much as 20% and more preferably by as much as 10% to the length of a reference quantity, level, value, dimension, length, position, size, or amount.

The term "alien" is used herein to refer to a substance produced in a modified plant that is not normally produced in a corresponding unmodified plant at the same developmental stage.

The term "biologically active portion", as applied to promoter sequences, refers to a portion that has at least about 0.1, 0.5, 1, 2, 5, 10, 12, 14, 16, 18, 20, 22, 24, 26, 28, 30% of the activity of a reference promoter sequence. It will also be understood that the phrase "biologically active portion" refers to a part of an indicated DNA sequence that initiates RNA transcription or that, when fused to a particular gene and introduced into a plant cell, causes expression of the gene at a level higher than is possible in the absence of such part of the indicated DNA sequence. Included within the scope of the present invention are biologically active portions of at least about 18, 19, 20, 21, 22, 23, 24, 25, 26, 27, 28, 29, 30, 40, 50, 60, 70, 80, 90, 100, 120, 140, 160, 180, 200, 250, 300, 400, 500, 600, 700, 800 or even 900 nucleotides in length.

As used herein, the term "cis-acting sequence", "cis-acting element" or "cis-regulatory region" or "regulatory region" or similar term shall be taken to mean any sequence of nucleotides, which when positioned appropriately relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In certain embodiments of the present invention, the cis-acting sequence is an activator sequence that enhances or stimulates the expression of an expressible genetic sequence.

Throughout this specification, unless the context requires otherwise, the words "comprise,", "comprises" and "comprising" will be understood to imply the inclusion of a stated step or element or group of steps or elements but not the exclusion of any other step or element or group of steps or elements.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

The term "endogenous" is used herein to refer to a substance that is normally produced in an unmodified plant at the same developmental stage as the plant under investigation.

The terms "foreign polynucleotide" or "exogenous polynucleotide" or "heterologous polynucleotide" and the like refer to any nucleic acid (e.g., a gene sequence) which is introduced into the genome of a plant by experimental manipulations and may include gene sequences found in that plant so long as the introduced gene contains some modification (e.g., a point mutation, the presence of a selectable marker gene, the presence of a loxP site, etc.) relative to the naturally-occurring gene.

The term "gene" as used herein refers to any and all discrete coding regions of the cell's genome, as well as associated non-coding and regulatory regions. The gene is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5 M sodium phosphate, 7% SDS at 65° C., followed by one or more washes at 0.2×SSC, 1% SDS at 65° C.

An "intron" is a region of DNA or RNA that is generally spliced out from the primary transcript RNA and is not present in the mature mRNA molecule.

Reference herein to "immuno-interactive" includes reference to any interaction, reaction, or other form of association between molecules and in particular where one of the molecules is, or mimics, a component of the immune system.

By "isolated" is meant material that is substantially or essentially free from components that normally accompany it in its native state. For example, an "isolated polynucleotide", as used herein, refers to a polynucleotide, which has been purified from the sequences which flank it in a naturally occurring state, e.g., a DNA fragment which has been removed from the sequences which are normally adjacent to the fragment.

By "marker gene" is meant a gene that imparts a distinct phenotype to cells expressing the marker gene and thus allows such transformed cells to be distinguished from cells that do not have the marker. A selectable marker gene confers a trait for which one can 'select' based on resistance to a selective agent (e.g., a herbicide, antibiotic, radiation, heat, or other treatment damaging to untransformed cells). A screenable marker gene (or reporter gene) confers a trait that one can identify through observation or testing, i.e., by 'screening' (e.g., β-glucuronidase, luciferase, or other enzyme activity not present in untransformed cells).

By "nucleome" is meant the total nucleic acid complement and includes the genome, extrachromosomal nucleic acid molecules and all RNA molecules such as mRNA, heterogenous nuclear RNA (hnRNA), small nuclear RNA (snRNA), small nucleolar RNA (snoRNA), small cytoplasmic RNA (scRNA), ribosomal RNA (rRNA), translational control RNA (tcRNA), transfer RNA (tRNA), eRNA, messenger-RNA-interfering complementary RNA (micRNA) or interference RNA (iRNA), chloroplast or plastid RNA (cpRNA) and mitochondrial RNA (mtRNA).

"Operably linked" or "operably connected" and the like refer to a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleic acid sequences being linked are typically contiguous and, where necessary to join two protein coding regions, contiguous and in reading frame. A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein. "Operably linking" a promoter to a transcribable polynucleotide means placing the transcribable polynucleotide (e.g., protein-encoding polynucleotide or other transcript) under the regulatory control of a promoter, which then controls the transcription and optionally translation of that polynucleotide. In the construction of heterologous promoter/structural gene combinations, it is generally preferred to position a promoter or variant thereof at a distance from the transcription start site of the transcribable polynucleotide, which is approximately the same as the distance between that promoter and the gene it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

As used herein, "plant" and "differentiated plant" refer to a whole plant or plant part containing differentiated plant cell types, tissues and/or organ systems. Plantlets and seeds are also included within the meaning of the foregoing terms. Plants included in the invention are any plants amenable to transformation techniques, including angiosperms, gymnosperms, monocotyledons and dicotyledons.

The term "plant cell" as used herein refers to protoplasts or other cells derived from plants, gamete-producing cells, and cells which regenerate into whole plants. Plant cells include cells in plants as well as protoplasts or other cells in culture.

By "plant tissue" is meant differentiated and undifferentiated tissue derived from roots, shoots, fruits, tubers, pollen, seeds, tumor tissue, such as crown galls, and various forms of aggregations of plant cells in culture, such as embryos and calluses.

The terms "polynucleotide variant" and "variant" and the like refer to polynucleotides displaying substantial sequence identity with a reference polynucleotide sequence or polynucleotides that hybridise with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that initiate RNA transcription or that, when fused to a particular gene and introduced into a plant cell, cause expression of the gene at a level higher than is possible in the absence of such polynucleotides. The terms "polynucleotide variant" and "variant" also include naturally occurring allelic variants.

The term "polynucleotide" or "nucleic acid" as used herein designates mRNA, RNA, cRNA, cDNA or DNA. The term typically refers to oligonucleotides greater than 30 nucleotides in length.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

"Promoter" is used herein in its broadest sense and includes a region of DNA, generally upstream (5') of the mRNA encoding region, which controls the initiation and level of transcription. Reference herein to a "promoter" is to be taken in its broadest context and includes the transcriptional regulatory sequences of a classical genomic gene, including a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. Promoters according to the invention may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribable sequence in many or all tissues of a plant.

By "sink tissue-specific promoter" is meant a promoter that preferentially directs expression of an operably linked transcribable sequence in the sink tissue of a plant (e.g., fruit tissues, root tissue, tuber tissue, seed tissue, culm tissue or sink leaf tissue) as compared to expression in other tissues of the plant, including source tissues (e.g., leaf).

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

The term "regeneration" as used herein in relation to plant materials means growing a whole, differentiated plant from a plant cell, a group of plant cells, a plant part (including seeds), or a plant piece (e.g., from a protoplast, callus, or tissue part).

By "reporter molecule" as used in the present specification is meant a molecule that, by its chemical nature, provides an analytically identifiable signal that allows the detection of a complex comprising an antigen-binding molecule and its target antigen. The term "reporter molecule" also extends to use of cell agglutination or inhibition of agglutination such as red blood cells on latex beads, and the like.

"Selective expression" as used herein refers to expression almost exclusively in specific organs of the plant, including, but not limited to fruit, tubers, root, or seed. The term may also refer to expression at specific developmental stages in an organ, such as in early or late embryogenesis or different stages of maturity in the culm; or to expression that is inducible by certain environmental conditions or treatments. Selective expression may therefore be contrasted with constitutive expression, which refers to expression in many or all tissues of a plant under most or all of the conditions experienced by the plant. Selective expression may also result in compartmentation of the products of gene expression in specific plant tissues, organs or developmental stages. Compartmentation in specific subcellular locations such as the cytosol, vacuole, or apoplastic space may be achieved by the inclusion in the structure of the gene product of appropriate signals for transport to the required cellular compartment, or in the case of the semi-autonomous organelles (plastids and mitochondria) by integration of the transgene with appropriate regulatory sequences directly into the organelle genome.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 50 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

"Sink cell" and "sink tissue" as used herein, refer to cells, tissues or organs which at the time of harvest comprise organic carbon that has entered the cells by net inflow in a form other than carbon dioxide. In plants, sink tissues include all non-photosynthetic tissues, as well as photosynthetic tissues with a net inflow of organic carbon fixed by other photosynthetic cells or otherwise obtained from the surrounding medium or environment by means other than direct fixation of carbon dioxide.

"Stringency" as used herein, refers to the temperature and ionic strength conditions, and presence or absence of certain organic solvents, during hybridization. The higher the stringency, the higher will be the degree of complementarity between immobilized nucleotide sequences and the labeled polynucleotide sequence.

"Stringent conditions" refers to temperature and ionic conditions under which only nucleotide sequences having a high frequency of complementary bases will hybridize. The stringency required is nucleotide sequence dependent and depends upon the various components present during hybridization. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridizes to a complementary probe.

The term "sugars," "sugar derivatives" is used herein in its broadest sense and includes: monosaccharides (aldoses and ketoses) comprising compounds with the empirical formula $(CH_2O)_n$ where n=3 or some larger number; including tetroses (e.g. erythrose, threose, erythrulose), pentoses (e.g. ribose, arabinose, xylose, lyxose, ribulose, xylulose), hexoses (e.g., allose, altrose, glucose, mannose, gulose, idose, galactose, talose, psicose, fructose, sorbose, tagatose), and longer molecules such as sedoheptulose or mannoheptulose; oligosaccharides formed by linking together of several monosaccharide units through glycosidic bonds; including disaccharides (e.g., maltose, lactose, gentibiose, melibiose, trehalose, sophorose, primoverose, rutinose, sucrose, isomaltulose, trehalulose, turanose, maltulose, leucrose) and longer oligomers such as raffinose, melezitose, bemisiose or stachyose; sugar alcohols (e.g., erythritol, ribitol, mannitol, sorbitol); sugar acids (e.g., gluconic acid, glucaric acid, glucuronic acid); amino sugars (e.g., glucosamine, galactosamine); and other variants such as deoxy sugars, methyl sugars, sugar phosphates and UDP-sugars, some of which may be converted into sugars or other sugar derivatives described above by the action of plant metabolic pathways.

The term "transformation" means alteration of the genotype of an organism, for example a bacterium or a plant, by the introduction of a foreign or endogenous nucleic acid. By "transformant" is meant an organism so altered.

As used herein the term "transgenic" refers to a genetically modified plant in which the endogenous genome is supplemented or modified by the random or site-directed integration, or stable maintenance in a replicable non-integrated form, of an introduced foreign or exogenous gene or sequence. By "transgene" is meant a gene or sequence that is introduced into a plant.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene that can be used for selection of suitable transformants. Examples of such resistance genes are well known to those of skill in the art.

Method of Modifying the Total Carbohydrate Content or Sweetness of Plant Tissue

The present invention is predicated in part on the discovery that expression of an exogenous or foreign sugar-metabolizing enzyme, such as a sucrose isomerase, in a plant (e.g., sugarcane), resulting in conversion of a proportion of cellular sucrose to isomaltulose (an alien sugar that is not normally produced in the plant), can result in substantially higher total carbohydrate concentrations in the sucrose storage tissues of the plant. Not wishing to be bound by any one particular theory or mode of operation, it is believed that specific alterations to metabolism, involving the conversion of a sugar normally sensed by the plant into a novel sugar that is not perceived in an equivalent manner, can shift metabolism and result in the accumulation of higher concentrations of carbohydrates. The inventors consider that such specific alterations at the cellular level can alter source-sink relationships at the whole plant level, resulting in higher accumulation of carbohydrates in sink tissues through a combination of effects on synthesis in source tissues, transport between source and sink tissues, and turnover or storage within the sink tissues.

Accordingly, the present invention provides novel methods for modifying the total carbohydrate content or sweetness of the sink tissue of a plant. The methods generally comprise producing in the plant a sugar-metabolizing enzyme that catalyzes the conversion of an endogenous sugar of the plant to an alien sugar that is not normally produced in the plant at the same developmental stage. Advantageously, the sugar-metabolizing enzyme is produced at a level or functional activity that increases the carbohydrate content or sweetness of the sink tissue as compared to that of the corresponding sink tissue of a control plant, which does not produce the enzyme. In some embodiments, the sugar-metabolizing enzyme is produced in the plant cells by expression of a polynucleotide that encodes the enzyme. In these embodiments, the plant is a transgenic plant that is selected from a plurality of transgenic plants which comprise in their nucleome the enzyme-encoding polynucleotide operably connected to a transcriptional control element. The transgenic plant is selected on the basis that it produces the sugar-metabolizing enzyme at a level or functional activity so that the total or soluble carbohydrate content or sweetness of the sink tissue of the transgenic plant is increased as compared to that of the corresponding sink tissue of the control plant.

In some embodiments, the total carbohydrate content or sweetness or the endogenous carbohydrate content of the sink tissue is increased by producing the sugar-metabolizing enzyme in cells of the plant at a level or functional activity that results in partial conversion of the endogenous sugar to the alien sugar. In these embodiments, the sugar-metabolizing enzyme is suitably active in the cytosol or distributed between the cytosol and other cellular compartments involved in sugar storage and/or transport. Typically, in these embodiments, less than about 30%, 20% or 15%, and suitably less than about 10%, 9%, 8%, 7%, 6%, 5%, 4%, 3%, 2% or 1% conversion of the endogenous sugar to the alien sugar achieves an increase in the soluble carbohydrate content or sweetness of the sink tissue. Preferably in these embodiments, the alien sugar is accumulated without commensurable reduction in the content of endogenous sugars or carbohydrates.

In other embodiments, the total carbohydrate content or sweetness or the endogenous carbohydrate content of the sink tissue is increased by targeting the sugar-metabolizing enzyme to a sub-cellular compartment used for sugar storage in the plant cells (e.g., vacuole or apoplasmic space). In these embodiments, the sugar-metabolizing enzyme is suitably present in the sub-cellular compartment at a level or functional activity that results in substantial conversion, which is generally at least about 20%, 25% or 30% but typically at least about 40%, 45%, 50% or 55% and more usually at least about 60%, 65%, 70%, 75%, 80%, 85% or 90% conversion, of the endogenous sugar to the alien sugar. Desirably, the substantial conversion does not occur within tissues undergoing cell division and/or cell expansion contributing to plant growth. Preferably in these embodiments, the alien sugar is accumulated without commensurable reduction in the content of endogenous sugars or carbohydrates.

Thus, modification of the total carbohydrate content or sweetness or the endogenous carbohydrate content of sink tissue is achieved by modulating the level of conversion of the endogenous sugar to the alien sugar. This conversion may be accomplished in tissues throughout the plant, for example using a constitutive promoter to drive expression of a sequence that codes for a sugar-metabolizing enzyme. Alternatively, it may be accomplished in source tissues, in transport tissues or in sink tissues using a tissue-specific or developmentally regulated promoter.

In some embodiments, the level of conversion of the endogenous sugar to the alien sugar is modulated by increasing or decreasing the level of expression of a sequence that codes for a sugar-metabolizing enzyme. By way of example, this can be achieved at the level of transcription by using promoters of different strengths or inducible promoters, which are capable of controlling the level of transcript expressed from the coding sequence. Alternatively, the level of expression of the enzyme coding sequence can be modulated by altering the copy number per cell of a construct comprising the coding sequence and a transcriptional control element that is operably connected thereto and that is functional in the cell. Alternatively, a plurality of transformants may be selected, and screened for those with a favorable level and/or specificity of transgene expression arising from influences of endogenous sequences in the vicinity of the transgene integration site. A favorable level and pattern of transgene expression is one which results in a substantial increase in soluble carbohydrate content or sweetness of the tissues intended for harvest. This may be detected by simple testing of transformants at about the developmental stage intended for harvest, for example using the method in Example 9. In certain embodiments, the expression level of the coding sequence is chosen such that it is at least about 10%, 20%, 30%, 40%, 50%, 60%, 70%, 80% or 90%, or even at least about 100%, 200%, 300%, 400%, 500%, 600%, 700%, 800%, 900% or 1000% higher, or at least about 10%, 20%, 30% 40%, 50%, 60%, 70%, 80%, 90%, 92%, 94%, 96%, 97%, 98% or 99%, or even at least about 99.5%, 99.9%, 99.95%, 99.99%, 99.995% or 99.999% lower than a reference expression level.

In another embodiment, the level of expression of the coding sequence can be modulated post-transcriptionally, by using sequences within the transcribed gene (cis RNA sequences) or by using separately transcribed sequences (trans RNA sequences) that affect the processing or stability of the mRNA encoding the sugar-metabolizing enzyme. For example, cis RNA sequences may alter the secondary structure of the untranslated leader or include out-of-frame start codons or sub-optimal start codon context or rare codon usage to control translation rate; or they may include sequences with some similarity to intron splice sites or polyadenylation signals that result in errors in RNA processing or reduced mRNA stability. Examples of trans RNA sequences include co-expressed antisense molecules or ribozymes that interfere with or inhibit the expression. Alternatively, RNA molecules of about 21 to about 23 nucleotides, which direct cleavage of specific mRNA to which they correspond, as for example described by Tuschl et al. in U.S. Patent Application No. 20020086356, can be utilized for mediating RNAi to thereby modulate the expression of the enzyme coding sequence.

In another embodiment, the level of conversion of the endogenous sugar to the alien sugar is modulated by using sugar-metabolizing enzymes of different functional activities. This may arise from differences in the specific activities or stabilities of the enzymes in the cellular compartment where the sugar conversion is accomplished. In certain embodiments, the activity of a sugar-metabolizing enzyme that is used for the conversion of the endogenous sugar to the alien sugar is at least about 10%, 20%, 30%, 40%, 50%, 60%, 70%, 80% or 90%, or even at least about 100%, 200%, 300%, 400%, 500%, 600%, 700%, 800%, 900% or 1000% higher, or at least about 10%, 20%, 30% 40%, 50%, 60%, 70%, 80%, 90%, 92%, 94%, 96%, 97%, 98% or 99%, or even at least about 99.5%, 99.9%, 99.95%, 99.99%, 99.995% or 99.999% lower than that of a reference enzyme. Sugar-metabolizing enzymes of different activities may be naturally occurring or may be obtained by synthetic or recombinant means, for example, by modification of the catalytic site or any other site (e.g., substrate-binding site, co-factor binding site) of a reference or parent enzyme. Typically, the modification is achieved by the substitution, addition or deletion of at least one amino acid in the sequence of parent enzyme using for example rational or established methods of mutagenesis or combinatorial chemistries, as are known in the art. Variant sugar-metabolizing enzymes may comprise conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, an amino acid residue in a parent enzyme is suitably replaced with another amino acid residue from the same side chain family. Alternatively, in another embodiment, mutations can be introduced randomly along all or part of a polynucleotide that codes for the reference enzyme, such as by saturation mutagenesis, and the resultant mutants can be screened for enzyme activity to identify mutants with a different activity than the parent enzyme. The enzymes of interest may be tested for relative activity for example using the method in Example 2, modified by incubation of the crude or purified enzyme preparations before and/or during the assay in conditions resembling the plant cellular compartment where the sugar conversion is to be accomplished, as an additional test of stability and specific activity under these conditions.

In other embodiments, the level of and location of conversion of the endogenous sugar to the alien sugar is modulated by using a sugar-metabolizing enzyme directed into different functional subcellular compartments. In illustrative examples, the activity is directed to the cytosol as a primary metabolic compartment. This may be achieved by expression of a nuclear gene, resulting in the synthesis within the cytosol of a form of the enzyme with no signal sequences for transport to other cellular compartments. In other illustrative examples, the activity is directed to a storage compartment such as the vacuole, or to a storage and transport compartment such as the extracellular (apoplasmic) space, by including within the sequence of the enzyme a signal for transport of the enzyme from the cytosol to the desired cellular compartment. Certain signal sequences can result in the distribution of enzyme activity between two or more cellular compartments (Small et al., 1998). For example the NTPP signal described in Example 4 (SEQ ID NO: 7) directs proteins efficiently to the sugarcane vacuole, whereas the CTPP signal described in Example 5 (SEQ ID NO: 8 plus SEQ ID NO: 9) can result in the distribution of proteins between the cytosol and the secretory pathway (comprising the vacuole, endomembrane system and apoplasm) in sugarcane (Gnanasambandam and Birch 2004).

Other factors may influence the modification of the soluble carbohydrate content or sweetness of the sink tissue, including the amount of substrate (i.e., endogenous sugar) available. The amount of substrate available to the sugar-metabolizing enzyme may depend on the plant species which is the subject of the modification (including mutants within a species), the tissue type where expression occurs, the subcellular location of expression and on the stage of development of a particular plant. The stability of the introduced protein may also depend on the amount of the substrate. However, it is considered that any optimization, which may be required in such an event, is achievable using routine methods including those described above.

The endogenous sugars produced by different plants may differ and as such an endogenous sugar of one plant may be an alien sugar of another. Thus, it is essential to determine which sugars are endogenously produced by a chosen plant to thereby deduce which sugars are alien to the plant and the type of sugar-metabolizing enzyme(s) that could be useful for producing an alien sugar in the plant. The types of sugars endogenously produced by plants can be determined using methods well known to persons of skill in the art. These methods include separation of sugars or sugar derivatives by electrophoresis or chromatography (including paper chromatography, thin layer chromatography, gas chromatography, gas-liquid chromatography and high-performance liquid chromatography) techniques. The separated components are typically identified by comparison of separation profiles with standards of known identity, or by analytical techniques such as mass spectrometry and nuclear magnetic resonance spectroscopy. For example, reference may be made to Example 9, Robinson 1980, *The Organic Constituents of Higher Plants*, Cordus Press, North Amherst, USA; Adams et al. 1999, *Anal. Biochem.* 266:77-84; Veronese and Perlot 1999, *Enz. Microbial Tech.* 24:263-269; Hendrix and Salvucci 2001, *J. Insect Physiol.* 47:423-432; Thompson et al. 2001, *Carbohydrate Res.* 331:149-161; and references cited therein.

Knowledge of the endogenous sugars produced by the plant permits the deduction of an appropriate sugar-metabolizing enzyme that converts one or more of the endogenous sugar to an alien sugar or sugar derivative. For example, the sugar-metabolizing enzyme may catalyze a reaction selected from an oxidation reaction, a reduction reaction, a dehydrogenation reaction, a hydrogenation reaction, an isomerization, a conjugation reaction including, but not limited to, acetylation, carboxylation, glucuronidation, glycine conjugation, methylation (O-, N-, or S-linked), phosphorylation and sulfate conjugation and a hydrolytic reaction. Examples of enzymes that may catalyze the desired conversions include isomerases, epimerases, mutases, kinases, aldolases, transferases, transketolases, phosphatases, synthases, carboxylases, dehydrogenases and hydrolases.

The endogenous and alien sugars are suitably selected from monosaccharides, oligosaccharides, sugar alcohols, sugar acids, amino sugars and other variants such as deoxy sugars, methyl sugars and the like. Examples of monosaccharides include compounds with of formula $(CH_2O)_n$ where $n=3$ or more but suitably less than 10; including compounds comprising tetroses (e.g., erythrose, threose, erythrulose), pentoses (e.g., ribose, arabinose, xylose, lyxose, ribulose, xylulose), hexoses (e.g., allose, altrose, glucose, mannose, gulose, idose, galactose, talose, psicose, fructose, sorbose, tagatose), and longer molecules such as sedoheptulose or mannoheptulose. Oligosaccharides, which are formed by linking together two or more monosaccharide units through glycosidic bonds, may be selected from disaccharides (e.g., maltose, lactose, gentibiose, melibiose, trehalose, sophorose, primoverose, rutinose, sucrose, isomaltulose, trehalulose, turanose, maltulose, leucrose) and longer oligomers such as raffinose, melezitose, bemisiose or stachyose. Examples of sugar alcohols include, but are not limited to, erythritol, ribitol, mannitol, sorbitol). Non-limiting examples of sugar acids include gluconic acid, glucaric acid, glucuronic acid. Non-limiting examples of amino sugars include glucosamine, galactosamine. Endogenous or alien sugars may also be selected from other variants such as deoxy sugars and methyl sugars, some of which may be converted into sugars or other sugar derivatives described above by the action of a plant metabolic pathway. In certain embodiments, the alien sugar is an isomer of the endogenous sugar. In one example of this embodiment, the endogenous sugar is sucrose and the sugar-metabolizing enzyme is a sucrose isomerase, which converts the sucrose by isomerization to an alien sugar selected from isomaltulose and trehalulose.

In accordance with the present invention, partial conversion of an endogenous sugar to an alien sugar by a sugar-metabolizing enzyme in a plant increases the total carbohydrate content or sweetness of the plant or a harvested portion of the plant as compared to that of the corresponding tissue of a control plant, which does not produce the enzyme. Exemplary carbohydrates include, but are not limited to, simple sugars such as glucose, fructose and sucrose as well as certain soluble polymers, and other soluble cell components. In one embodiment the method produces sink tissue having increased carbon as soluble carbohydrates, as an increased ratio of soluble carbohydrates per unit weight of sink tissue, as compared to that measured in control plant cells. Carbohydrates can be assayed using standard protocols known to persons skilled in the art.

Method of Increasing the Content of Desired Metabolites in Organisms

The principles and methods elaborated here in detail for increasing the content of carbohydrates in plants can also be applied to increase the content of carbohydrates in other organisms in which different storage carbohydrates predominate, such as trehalose in fungi and glycogen in animals. These principles and methods can also be applied to increase the content of other classes of desired metabolites, such as lipids, amino acids and peptides or secondary metabolites in an organism. Persons skilled in the art will recognize that variations on the methods disclosed in detail herein, for the example, of increased carbohydrates in plants, can accomplish increases in other classes of desired metabolites in an organism. Accordingly, the present invention broadly encompasses the expression within an organism of an introduced gene resulting in the partial conversion of a substrate endogenous compound that is normally sensed by the organism into a product compound that is not perceived in an equivalent manner within the organism, with the effect that metabolic flows are altered, resulting in the accumulation of higher yields of desired endogenous compounds.

Nucleic Acid Constructs

In certain embodiments, the sugar-metabolizing enzyme is produced in the plant cells by expression of a foreign or exogenous polynucleotide that encodes the enzyme. Generally, the foreign or exogenous polynucleotide is operably connected to a transcriptional control element in a nucleic acid construct. The transcriptional control element suitably includes a promoter, and optionally a cis-acting sequence, each of which are functional in the plant cells. Advantageously, the construct includes one or both of a 3' non-translated sequence and a marker gene.

Transcriptional Control Elements

Promoter sequences contemplated by the present invention may be native to the host plant to be transformed or may be derived from an alternative source, where the region is functional in the host plant. Other sources include the *Agrobacterium* T-DNA genes, such as the promoters for the biosynthesis of nopaline, octapine, mannopine, or other opine promoters; promoters from plants, such as the ubiquitin promoter; tissue specific promoters (see, e.g., U.S. Pat. No. 5,459,252 to Conkling et al.; WO 91/13992 to Advanced Technologies); promoters from viruses (including host specific viruses), or partially or wholly synthetic promoters. Numerous promoters that are functional in mono- and dicotyledonous plants are well known in the art (see, for example, Greve, 1983, *J. Mol. Appl. Genet.* 1: 499-511; Salomon et al., 1984, *EMBO J.* 3: 141-146; Garfinkel et al., 1983, *Cell* 27: 143-153; Barker et al., 1983, *Plant Mol. Biol.* 2: 235-350); including various promoters isolated from plants (such as the Ubi promoter from the maize ubi-1 gene, Christensen and Quail, 1996) (see, e.g., U.S. Pat. No. 4,962,028) and viruses (such as the cauliflower mosaic virus promoter, CaMV 35S).

The promoters sequences may include cis-acting sequences which regulate transcription, where the regulation involves, for example, chemical or physical repression or induction (e.g., regulation based on metabolites, light, or other physicochemical factors; see, e.g., WO 93/06710 disclosing a nematode responsive promoter) or regulation based on cell differentiation (such as associated with leaves, roots, seed, or the like in plants; see, e.g., U.S. Pat. No. 5,459,252 disclosing a root-specific promoter). Thus, the promoter region, or the regulatory portion of such region, is obtained from an appropriate gene that is so regulated. For example, the 1,5-ribulose biphosphate carboxylase gene is light-induced and may be used for transcriptional initiation. Other genes are known which are induced by stress, temperature, wounding, pathogen effects, etc.

Other cis-acting sequences which may be employed include transcriptional and/or translational enhancers. These enhancer regions are well known to persons skilled in the art, and can include the ATG initiation codon and adjacent sequences. The initiation codon must be in phase with the reading frame of the coding sequence relating to the foreign or exogenous polynucleotide to ensure translation of the entire sequence. The translation control signals and initiation codons can be of a variety of origins, both natural and synthetic. Translational initiation regions may be provided from the source of the transcriptional initiation region, or from the foreign or exogenous polynucleotide. The sequence can also be derived from the source of the promoter selected to drive transcription, and can be specifically modified so as to increase translation of the mRNA.

Examples of transcriptional enhancers include, but are not restricted to, elements from the CaMV 35S promoter and octopine synthase genes as for example described by Last et al. (U.S. Pat. No. 5,290,924, which is incorporated herein by reference). It is proposed that the use of an enhancer element such as the ocs element, and particularly multiple copies of the element, will act to increase the level of transcription from adjacent promoters when applied in the context of plant transformation. Alternatively, the omega sequence derived from the coat protein gene of the tobacco mosaic virus (Gallie et al., 1987) may be used to enhance translation of the mRNA transcribed from a polynucleotide according to the invention.

In some embodiments, the transcriptional control element is a constitutive promoter. Among sequences known to be useful in providing for constitutive gene expression are regulatory regions associated with *Agrobacterium* genes, such as for example nopaline synthase (Nos), mannopine synthase (Mas), or octopine synthase (Ocs), as well as regions coding for expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable.

In other embodiments, the transcriptional control element is a tissue-specific promoter. For example, in providing for expression of the sugar-metabolizing enzymes, for various reasons one may wish to limit the expression of these enzymes to plant cells which function as carbon sinks. Towards this end, one can identify useful transcriptional initiation regions that provide for expression preferentially in specific tissue types, such as roots, tubers, seeds or fruit. These sequences may be identified from cDNA libraries using differential screening techniques, for example, or may be derived from sequences known in the literature.

Many tissue specific promoter regions are known, such as the Rubisco small subunit promoter which preferentially is expressed in leaf tissue, the patatin promoter which is preferentially in potato tubers. Other transcriptional initiation regions which preferentially provide for transcription in certain tissues or under certain growth conditions, include those from napin, seed or leaf ACP, zein, and the like. Fruit specific promoters are also known, one such promoter is the E8 promoter, described by Deikman et al. (1988, *EMBO J.* 2: 3315-3320) and DellaPenna et al. (1989, *Plant Cell* 1: 53-63). In one embodiment of this type, an E8 (fruit-specific promoter)-sucrose isomerase construct will express sucrose isomerase in a fruit-specific manner, whereby the levels of sucrose produced in the fruit may be elevated. Alternatively, promoters that selectively express coding sequences in sucrose storage tissues (such as the mature stems of sugarcane and the tubers of sugar beet) may be used. For example, promoters specific for the mature stems of sugarcane are described in Section 6 herein and in International Publication WO 01/18211.

Alternatively, the promoter is an inducible promoter, which is capable of driving expression of the enzyme-encoding polynucleotide at an appropriate developmental stage of the plant. In this latter embodiment, the transcriptional control element is suitably a developmentally regulated promoter to control the timing of expression. Timing the expression of sugar-metabolizing enzymes advantageously takes into consideration the change in sugar concentration that occurs during plant development. The importance of a sugar within tissue may also change with time and, in this regard, sink tissue may undergo changes in sucrose concentrations during development. For example, sucrose concentration in certain fruits such as sweet melons changes as the fruit matures. Hexose sugars accumulate early in development, followed by high levels of sucrose at later stages (Schaffer et al., 1987, *Phytochemistry* 26: 1883-1887). In developing corn endosperm, sucrose concentration increases from 8 to 12 days after pollination and then drops more than ten fold 28 days after pollination (Tsai et al., 1970, *Plant Phys.* 46: 299-306). Additionally, sucrose concentration in soybean seed changes significantly during development as raffinose saccharides content increases dramatically, 53 days after anthesis (Amuti, 1977, *Phytochemistry* 16: 529-532). In pea seed, sucrose content falls dramatically with continued development (Holl and Vose, Can. 1980, *J. Plant Sci.* 60: 1109-1114). These examples illustrate the desirability of promoter selection for specific expression of an enzyme gene timed to take advantage of fluctuating sucrose pools.

3' Non-Translated Region

The nucleic acid construct of the present invention can comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon.

The 3' non-translated regulatory DNA sequence typically includes from about 50 to 1,000 nucleotide base pairs and may contain plant transcriptional and translational termination sequences in addition to a polyadenylation signal and any other regulatory signals capable of effecting mRNA processing or gene expression. Examples of suitable 3' non-translated sequences are the 3' transcribed non-translated regions containing a polyadenylation signal from the nopaline synthase (nos) gene of *Agrobacterium tumefaciens* (Bevan et al., 1983, *Nucl. Acid Res.*, 11:369) and the terminator for the T7 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the pea E9 small subunit of the ribulose-1,5-bisphosphate carboxylase (ss-RUBISCO) gene, although other 3' elements known to those of skill in the art can also be employed. Alternatively, 3' non-translated regulatory sequences can be obtained de novo as, for example, described by An (1987, *Methods in Enzymology*, 153:292), which is incorporated herein by reference.

Optional Sequences

As the DNA sequence inserted between the transcription initiation site and the start of the coding sequence, i.e., the untranslated leader sequence, can influence gene expression, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987, *Nucl. Acid Res.*, 15:6643). However, other leader sequences, e.g., the leader sequence of RTBV, have a high degree of secondary structure that is expected to decrease mRNA stability and/or decrease translation of the mRNA. Thus, leader sequences (i) that do not have a high degree of secondary structure, (ii) that have a high degree of secondary structure where the secondary structure does not inhibit mRNA stability and/or decrease translation, or (iii) that are derived from genes that are highly expressed in plants, will be most preferred.

Regulatory elements such as the sucrose synthase intron as, for example, described by Vasil et al. (1989, *Plant Physiol.*, 91:5175), the Adh intron I as, for example, described by Callis et al. (1987, *Genes Develop.*, II), or the TMV omega element as, for example, described by Gallie et al. (1989, *The Plant Cell*, 1:301) can also be included where desired. Other such regulatory elements useful in the practice of the invention are known to those of skill in the art.

Additionally, targeting sequences may be employed to target the enzyme encoded by the foreign or exogenous polynucleotide to an intracellular compartment within plant cells or to the extracellular environment. For example, a nucleic acid sequence encoding a transit or signal peptide sequence may be operably linked to a sequence that encodes a chosen enzyme of the subject invention such that, when translated, the transit or signal peptide can transport the enzyme to a particular intracellular or extracellular destination, and can then be optionally post-translationally removed. Transit or signal peptides act by facilitating the transport of proteins through intracellular membranes, e.g., endoplasmic reticulum, vacuole, vesicle, plastid, mitochondrial and plasmalemma membranes. For example, the targeting sequence can direct a desired protein to a particular organelle such as a vacuole or a plastid (e.g., a chloroplast), rather than to the cytosol. Thus, the nucleic acid construct of the invention can further comprise a plastid transit peptide-encoding nucleic acid sequence operably linked between a promoter region and the foreign or exogenous polynucleotide. For example, reference may be made to Heijne et al. (1989, *Eur. J. Biochem.*, 180:535) and Keegstra et al. (1989, *Ann. Rev. Plant Physiol. Plant Mol. Biol.*, 40:471).

In some embodiments, sucrose (i.e., an endogenous sugar) stored in sink tissue cells is converted to isomaltulose and/or trehalulose (i.e., an alien sugar) via introduction of a bacterial sucrose isomerase gene with a sink tissue specific promoter and cytosol localization regulatory sequences. In these embodiments, the inventors chose the cytosol for expression of the sucrose isomerase gene because it is a key cellular compartment involved in many elements of intermediary metabolism and in the flux of many metabolites. In other embodiments, they chose the vacuole as a location for sucrose isomerase activity because it is the primary storage compartment for sugars in plants such as sugarcane. In still other embodiments, they chose to distribute the sucrose isomerase activity between compartments to achieve optimal effect in the total accumulation of sugars. In other embodiments, it may be appropriate to direct the expression of the enzyme gene product to other cellular compartments such as the vacuoles, lysosomes, peroxisomes, plastids, mitochondria, endoplasmic reticulum, nucleus or the extracellular space as appropriate to the metabolic pathways of interest.

The nucleic acid construct of the invention can be introduced into a vector, such as a plasmid. Plasmid vectors include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

The vector preferably contains one or more elements that permits either stable integration of the vector into the host cell genome or autonomous replication of the vector in the cell independent of the genome of the cell. The vector may be integrated into the host cell genome when introduced into a host cell. For integration, the vector may rely on a foreign or exogenous polynucleotide sequence present therein or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector to be integrated into the host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

For cloning and subcloning purposes, the vector may further comprise an origin of replication enabling the vector to replicate autonomously in a host cell such as a bacterial cell. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. The origin of replication may be one having a mutation to make its function temperature-sensitive in a *Bacillus* cell (see, e.g., Ehrlich, 1978, *Proc. Natl. Acad. Sci. USA* 75:1433).

Marker Genes

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Included within the terms selectable or screenable marker genes are genes that encode a "secretable marker" whose secretion can be detected as a means of identifying or selecting for transformed cells. Examples include markers that encode a secretable antigen that can be identified by antibody interaction, or secretable enzymes that can be detected by their catalytic activity. Secretable proteins include, but are not restricted to, proteins that are inserted or trapped in the cell wall (e.g., proteins that include a leader sequence such as that found in the expression unit of extensin or tobacco PR-S); small, diffusible proteins detectable, e.g. by ELISA; and small active enzymes detectable in extracellular solution (e.g., α-amylase, β-lactamase, phosphinothricin acetyltransferase).

Selectable Markers

Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (neo) gene conferring resistance to kanamycin, paromomycin, G418 and the like as, for example, described by Potrykus et al. (1985, *Mol. Gen. Genet.* 199: 183); a glutathione-S-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described WO87/05327, an acetyl transferase gene from *Streptomyces viridochromogenes* conferring resistance to the selective agent phosphinothricin as, for example, described in EP-A 275 957, a gene encoding a 5-enolshikimate-3-phosphate synthase (EPSPS) conferring tolerance to N-phosphonomethylglycine as, for example, described by Hinchee et al. (1988, *Biotech.*, 6:915), a bar gene conferring resistance against bialaphos as, for example, described in WO91/02071; a nitrilase gene such as bxn from *Klebsiella ozaenae* which confers resistance to bromoxynil (Stalker et al., 1988, *Science*, 242:419); a dihydrofolate reductase (DHFR) gene conferring resistance to methotrexate (Thillet et al., 1988, *J. Biol. Chem.*, 263:12500); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers resistance to the herbicide.

Screenable Markers

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985, *Biochem. Biophys. Res. Comm.*, 126:1259), which may be employed in calcium-sensitive bioluminescence detection; a green fluorescent protein gene (Niedz et al., 1995 *Plant Cell Reports*, 14:403); a luciferase (luc) gene (Ow et al., 1986, *Science*, 234:856), which allows for bioluminescence detection; a β-lactamase gene (Sutcliffe, 1978, *Proc. Natl. Acad. Sci. USA* 75:3737), which encodes an enzyme for which various chromogenic substrates are known (e.g., PADAC, a chromogenic cephalosporin); an R-locus gene, encoding a product that regulates the production of anthocyanin pigments (red color) in plant tissues (Dellaporta et al., 1988, in *Chromosome Structure and Function*, pp. 263-282); an α-amylase gene (Ikuta et al., 1990, *Biotech.*, 8:241); a tyrosinase gene (Katz et al., 1983, *J. Gen. Microbiol.*, 129:2703) which encodes an enzyme capable of oxidizing tyrosine to dopa and dopaquinone which in turn condenses to form the easily detectable compound melanin; or a xylE gene (Zukowsky et al., 1983, *Proc. Natl. Acad. Sci. USA* 80:1101), which encodes a catechol dioxygenase that can convert chromogenic catechols.

Introduction of Nucleic Acid Construct into Plant Cells

A number of techniques are available for the introduction of nucleic acid molecules into a plant host cell. There are many plant transformation techniques well known to workers in the art, and new techniques are continually becoming known. The particular choice of a transformation technology will be determined by its efficiency to transform certain plant species as well as the experience and preference of the person practicing the invention with a particular methodology of choice. It will be apparent to the skilled person that the particular choice of a transformation system to introduce a nucleic acid construct into plant cells is not essential to or a limitation of the invention, provided it achieves an acceptable level of nucleic acid transfer. Guidance in the practical implementation of transformation systems for plant improvement is provided by Birch (1997, *Annu. Rev. Plant Physiol. Plant Molec. Biol.* 48: 297-326).

In principle, both dicotyledonous and monocotyledonous plants that are amenable to transformation, can be modified by introducing a nucleic acid construct according to the invention into a recipient cell and growing a new plant that harbors and expresses a polynucleotide according to the invention.

Introduction and expression of foreign or exogenous polynucleotides in dicotyledonous (broad-leaved) plants such as tobacco, potato and alfalfa has been shown to be possible using the T-DNA of the tumor-inducing (Ti) plasmid of *Agrobacterium tumefaciens* (See, for example, Umbeck, U.S. Pat. No. 5,004,863, and International application PCT/US93/02480). A construct of the invention may be introduced into a plant cell utilizing *A. tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is preferred that the *Agrobacterium* harbors a binary Ti plasmid system. Such a binary system comprises (1) a first Ti plasmid having a virulence region essential for the introduction of transfer DNA (T-DNA) into plants, and (2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells as, for example, described by De Framond (1983, *Biotechnology*, 1:262) and Hoekema et al. (1983, *Nature*, 303:179). Such a binary system is preferred inter alia because it does not require integration into the Ti plasmid in *Agrobacterium*.

Methods involving the use of *Agrobacterium* include, but are not limited to: (a) co-cultivation of *Agrobacterium* with cultured isolated protoplasts; (b) transformation of plant cells or tissues with *Agrobacterium*; or (c) transformation of seeds, apices or meristems with *Agrobacterium*.

Rice and corn, which are monocots, have been shown to be susceptible to transformation by *Agrobacterium* as well. However, many other important monocot crop plants, including oats, sorghum, millet, and rye, have not yet been successfully transformed using *Agrobacterium*-mediated transformation. The Ti plasmid, however, may be manipulated in the future to act as a vector for these other monocot plants. Additionally, using the Ti plasmid as a model system, it may be possible to artificially construct transformation vectors for these plants. Ti plasmids might also be introduced into monocot plants by artificial methods such as microinjection, or fusion between monocot protoplasts and bacterial spheroplasts containing the T-region, which can then be integrated into the plant nuclear DNA.

In addition, gene transfer can be accomplished by in situ transformation by *Agrobacterium*, as described by Bechtold et al. (1993, *C.R. Acad. Sci. Paris*, 316:1194). This approach is based on the vacuum infiltration of a suspension of *Agrobacterium* cells.

Alternatively, the chimeric construct may be introduced using root-inducing (Ri) plasmids of *Agrobacterium* as vectors.

Cauliflower mosaic virus (CaMV) may also be used as a vector for introducing of exogenous nucleic acids into plant cells (U.S. Pat. No. 4,407,956). CaMV DNA genome is inserted into a parent bacterial plasmid creating a recombinant DNA molecule that can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

The nucleic acid construct can also be introduced into plant cells by electroporation as, for example, described by Fromm et al. (1985, *Proc. Natl. Acad. Sci., U.S.A*, 82:5824) and Shimamoto et al. (1989, *Nature* 338:274-276). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus.

Another method for introducing the nucleic acid construct into a plant cell is high velocity ballistic penetration by small particles (also known as particle bombardment or microprojectile bombardment) with the nucleic acid to be introduced contained either within the matrix of small beads or particles, or on the surface thereof as, for example described by Klein et al. (1987, *Nature* 327:70). Although typically only a single introduction of a new nucleic acid sequence is required, this method particularly provides for multiple introductions.

Alternatively, the nucleic acid construct can be introduced into a plant cell by contacting the plant cell using mechanical or chemical means. For example, a nucleic acid can be mechanically transferred by microinjection directly into plant cells by use of micropipettes. Alternatively, a nucleic acid may be transferred into the plant cell by using polyethylene glycol which forms a precipitation complex with genetic material that is taken up by the cell.

There are a variety of methods known currently for transformation of monocotyledonous plants. Presently, methods for transformation of monocots are microprojectile bombardment of explants or suspension cells, *Agrobacterium*-mediated gene transfer, and direct DNA uptake or electroporation as, for example, described by Shimamoto et al. (1989, supra). Transgenic maize plants have been obtained by introducing the *Streptomyces hygroscopicus* bar gene into embryogenic cells of a maize suspension culture by microprojectile bombardment (Gordon-Kamm, 1990, *Plant Cell*, 2:603-618). The introduction of genetic material into aleurone protoplasts of other monocotyledonous crops such as wheat and barley has been reported (Lee, 1989, *Plant Mol. Biol.* 13:21-30). Wheat plants have been regenerated from embryogenic suspension culture by selecting only the aged compact and nodular embryogenic callus tissues for the establishment of the embryogenic suspension cultures (Vasil, 1990, *Bio/Technol.* 8:429-434). The combination with transformation systems for these crops enables the application of the present invention to monocots. These methods may also be applied for the transformation and regeneration of dicots. Transgenic sugarcane plants have been regenerated from embryogenic callus as, for example, described by Bower et al. (1996, *Molecular Breeding* 2:239-249).

Alternatively, a combination of different techniques may be employed to enhance the efficiency of the transformation process, e.g., bombardment with *Agrobacterium* coated microparticles (EP-A-486234) or microprojectile bombardment to induce wounding followed by co-cultivation with *Agrobacterium* (EP-A-486233).

Preferred plants for the present invention are species grown or harvested for their yield of valuable substances including soluble carbohydrates, which are used for example as foods, feeds, fermentation or industrial feedstocks among other uses. Examples of such species include sugar crops such as sugarcane, sugar beet, sweet sorghum, and chicory; fruits such as grapes, citrus, pome fruits, stone fruits and nuts; vegetables harvested for their leaves, stems, roots, tubers, fruits, pods or seeds; and pasture plants.

Promoter Sequences of the Invention

The present invention also provides a promoter sequence for stem-specific expression of chimeric or heterologous genes in plants, especially in monocotyledonous plants, and more especially in graminaceous monocotyledonous plants, which comprises the sequence set forth in SEQ ID NO:10. This promoter sequence is also referred to herein as the P67B promoter. The invention also contemplates biologically active portions of SEQ ID NO:10 as well as polynucleotide sequence variants thereof. Those of skill in the art will understand that a biologically active portion or fragment of a promoter sequence, when fused to a particular gene and introduced into a plant cell, causes expression of the gene at a level higher than is possible in the absence of such fragment. One or more biologically active portions may be included in a promoter according to the present invention, for instance one or more motifs may be coupled to a "minimal" promoter. Such motifs may confer P67B promoter function on a promoter, such as suitability for enhanced performance in the stems of monocotyledonous plants and especially of graminaceous monocotyledonous plants, illustrative examples of which include sugarcane, rice, wheat, sorghum, barley, rye, maize and the like.

The activity of a promoter can be determined by methods well known in the art. For example, the level of promoter activity is quantifiable by assessment of the amount of mRNA produced by transcription from the promoter or by assessment of the amount of protein product produced by translation of mRNA produced by transcription from the promoter.

The amount of a specific mRNA present in an expression system may be determined for example using specific oligonucleotides which are able to hybridize with the mRNA and which are labeled or may be used in a specific amplification reaction such as PCR. Use of a reporter gene facilitates determination of promoter activity by reference to protein production. Non-limiting methods for assessing promoter activity are disclosed by Medberry et al. (1992, *Plant Cell* 4:185; 1993, *The Plant J.* 3:619), Sambrook et al. (1989, supra) and McPherson et al. (U.S. Pat. No. 5,164,316).

The present invention also contemplates promoter variants that are substantially complementary to a reference promoter of the invention. In general, these promoter variants will comprise regions that show suitably at least 90, 91, 92, 93, 94, 95, 96, 97, 98 or 99% sequence identity over a reference polynucleotide sequence of identical size ("comparison window") or when compared to an aligned sequence in which the alignment is performed by a computer homology program known in the art. What constitutes suitable variants may be determined by conventional techniques. For example, a polynucleotides according to SEQ ID NO:10 can be mutated using random mutagenesis (e.g., transposon mutagenesis), oligonucleotide-mediated (or site-directed) mutagenesis, PCR mutagenesis and cassette mutagenesis of an earlier prepared variant or non-variant version of an isolated natural promoter according to the invention, according to standard protocols known to persons of skill in the art. Alternatively, promoter sequence variants may be prepared according to the following procedure:

(a) obtaining a nucleic acid extract from a suitable organism, which is suitably a monocot, and preferably a graminaceous monocot such as sugarcane;

(b) designing primers which flank at least a portion of a reference promoter sequence of the invention; and (c) using the primers to amplify, via nucleic acid amplification techniques, at least one amplification product from the nucleic acid extract, wherein the amplification product corresponds to a promoter variant of the invention.

Suitable nucleic acid amplification techniques are well known to the skilled addressee, and include polymerase chain reaction (PCR) as for example described in Ausubel et al. (supra); strand displacement amplification (SDA) as for example described in U.S. Pat. No. 5,422,252; rolling circle replication (RCR) as for example described in Liu et al., (1996, *J. Am. Chem. Soc.* 118:1587-1594 and International application WO 92/01813) and Lizardi et al., (International Application WO 97/19193) nucleic acid sequence-based amplification (NASBA) as for example described by Sooknanan et al., (1994, *Biotechniques* 17:1077-1080); and Q-β replicase amplification as for example described by Tyagi et al., (1996, *Proc. Natl. Acad. Sci. USA* 93:5395-5400).

Uses of the Promoter of the Invention

The isolated promoter sequence of the invention may be used, inter alia, to drive expression of a foreign or endogenous DNA sequence. The foreign or endogenous DNA sequence may comprise a region transcribed into an RNA molecule that modulates the expression of a corresponding target gene. Such modulation of expression may be achieved, for example, by antisense technology, ribozyme technology and co-suppression or homology-dependent gene silencing, as is known in the art. Accordingly, the transcript may comprise an antisense RNA molecule, or a ribozyme or other transcript (such as inverted repeats and dsRNA, as mentioned, for instance, below) aimed at downregulation of expression of the corresponding target gene.

Thus, in some embodiments, the transcript is an antisense RNA molecule that directly blocks the translation of mRNA transcribed from a target, gene by binding to the mRNA and preventing protein translation. When employed, antisense RNAs should be at least about 10-20 nucleotides or greater in length, and be at least about 75% complementary to their target genes or gene transcripts such that expression of the targeted homologous sequence is precluded.

In other embodiments, the transcript is a ribozyme that functions to inhibit the translation of a target gene mRNA. Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Within the scope of the invention are engineered hammerhead motif ribozyme molecules that specifically and efficiently catalyze endonucleolytic cleavage of target gene RNA sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. When employed, ribozymes may be selected from the group consisting of hammerhead ribozymes, axehead ribozymes, newt satellite ribozymes, Tetrahymena ribozymes and RNAse P, and are designed according to methods known in the art based on the sequence of the target gene (for instance, see U.S. Pat. No. 5,741,679). The suitability of candidate targets may also be evaluated by testing their accessibility to hybridization with complementary oligonucleotides, using ribonuclease protection assays.

In other embodiments, the transcript is an RNA molecule that mediates RNA interference (RNAi) of a target gene or gene transcript. RNAi refers to interference with or destruction of the product of a target gene by introducing a single stranded, and typically a double stranded RNA (dsRNA), which is homologous to the transcript of a target gene. Thus, in some embodiments, dsRNA per se and especially dsRNA-producing constructs corresponding to at least a portion of a target gene may be used to decrease its level and/or functional activity. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a target gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts which then anneal to form a dsRNA having homology to a target gene.

Absolute homology is not required for RNAi, with a lower threshold being described at about 85% homology for a dsRNA of about 200 base pairs (Plasterk and Ketting, 2000, *Current Opinion in Genetics and Dev.* 10: 562-67). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene.

RNA-encoding constructs that express a single RNA transcript designed to anneal to a separately expressed RNA, or single constructs expressing separate transcripts from convergent promoters, are preferably at least about 100 nucleotides in length. RNA-encoding constructs that express a single RNA designed to form a dsRNA via internal folding are preferably at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In another embodiment, RNA molecules of about 21 to about 23 nucleotides, which direct cleavage of specific mRNA to which they correspond, as for example described by Tuschl et al. in U.S. patent application No. 20020086356, can be utilized for mediating RNAi. Such 21-23 nt RNA molecules can comprise a 3' hydroxyl group, can be single-stranded or double stranded (as two 21-23 nt RNAs) wherein the dsRNA molecules can be blunt ended or comprise overhanging ends (e.g., 5', 3').

In other embodiments, the foreign or endogenous DNA sequence encodes: a detectable or measurable product, e.g. β-glucuronidase or luciferase; a selectable product, e.g., neomycin phosphotransferase (nptII) conferring resistance to aminoglycosidic antibiotics such as Geneticin® and paromomycin; a product conferring herbicide tolerance, e.g. glyphosate resistance or glufosinate resistance; a product affecting starch biosynthesis or modification e.g. starch branching enzyme, starch synthases, ADP-glucose pyrophosphorylase; a product involved in fatty acid biosynthesis, e.g. desaturase or hydroxylase; a product conferring insect resistance, e.g. crystal toxin protein of *Bacillus thuringiensis*; a product conferring viral resistance, e.g. viral coat protein; a product conferring fungal resistance, e.g. chitinase, β-1,3-glucanase or phytoalexins; a product altering sucrose metabolism, e.g. invertase or sucrose synthase; a gene encoding valuable pharmaceuticals, e.g. antibiotics, secondary metabolites, pharmaceutical peptides or vaccines.

The foreign or endogenous DNA sequence includes, but is not limited to, DNA from plant genes, and non-plant genes such as those from bacteria, yeasts, animals or viruses. Moreover, it is within the scope of the invention to isolate a foreign or endogenous DNA sequence from a given plant genotype, and to subsequently introduce multiple copies of that sequence into the same genotype, e.g., to enhance production of a given gene product. The introduced DNA can include modified genes, portions of genes, or chimeric genes, including genes from the same or different plant genotype.

Exemplary agronomic properties encoded by the foreign or endogenous DNA sequence include, but are not limited to: traits that are beneficial to the grower such as resistance to water deficit, pest resistance or tolerance, herbicide resistance or tolerance, disease resistance or tolerance (e.g., resistance to viruses or fungal pathogens), stress tolerance (increased salt tolerance) and improved food content or increased yields; traits that are beneficial to the consumer of the horticultural produce harvested from the plant such as improved nutritive content in human food or animal feed; or beneficial to the food processor such as improved processing traits. In such uses, the transgenic plants containing the promoter of the invention are generally grown for the use of their grain, fruit and other plant parts, including stalks, husks, vegetative parts, and the like in human or animal foods including use as part of animal silage or for ornamental purposes. Often, chemical constituents of crops are extracted for foods or industrial use and transgenic plants may be created which have enhanced or modified levels of such components.

The isolated promoter sequence of the invention may also find use in the commercial manufacture of proteins or other compounds, where the compound of interest is extracted or purified from plant parts, seeds, and the like. Such proteins or compounds include, but are not limited to, immunogenic molecules for use in vaccines, cytokines and hormones. Cells or tissue from the plants may also be cultured, grown in vitro, or fermented to manufacture such molecules.

The transgenic plants containing the isolated promoter sequence of the invention may also be used in commercial breeding programs, or may be crossed or bred to plants of related crop species. Improvements encoded by the foreign or endogenous DNA sequence may be transferred, e.g., from cells of one plant species to cells of another plant species, e.g., by protoplast fusion.

The transgenic plants containing the isolated promoter sequence of the invention may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation or the introduction of unique "signature sequences" or other marker sequences which can be used to identify proprietary lines or varieties.

Production and Characterization of Differentiated Transgenic Plants

Regeneration

The methods used to regenerate transformed cells into differentiated plants are not critical to this invention, and any method suitable for a target plant can be employed. Normally, a plant cell is regenerated to obtain a whole plant following a transformation process.

Regeneration from protoplasts varies from species to species of plants, but generally a suspension of protoplasts is made first. In certain species, embryo formation can then be induced from the protoplast suspension, to the stage of ripening and germination as natural embryos. The culture media will generally contain various amino acids and hormones, necessary for growth and regeneration. Examples of hormones utilized include auxins and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible. Regeneration also occurs from plant callus, explants, organs or parts. Transformation can be performed in the context of organ or plant part regeneration as, for example, described in *Methods in Enzymology*, Vol. 118 and Klee et al. (1987, *Annual Review of Plant Physiology*, 38:467), which are incorporated herein by reference. Utilizing the leaf disk-transformation-regeneration method of Horsch et al. (1985, *Science*, 227:1229, incorporated herein by reference), disks are cultured on selective media, followed by shoot formation in about 2-4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by the taking of cuttings or by tissue culture techniques to produce multiple identical plants. Selection of desirable transformants is made and new varieties are obtained and propagated vegetatively for commercial use.

In seed propagated crops, the mature transgenic plants can be self-crossed to produce a homozygous inbred plant. The inbred plant produces seed containing the newly introduced foreign gene(s). These seeds can be grown to produce plants that would produce the selected phenotype, e.g., early flowering.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

It will be appreciated that the literature describes numerous techniques for regenerating specific plant types and more are continually becoming known. Those of ordinary skill in the art can refer to the literature for details and select suitable techniques without undue experimentation.

Characterization

To confirm the presence of the foreign or exogenous polynucleotide in the regenerating plants, a variety of assays may be performed. Such assays include, for example, "molecular biological" assays well known to those of skill in the art, such as Southern and northern blotting and PCR; assays that determine sugar-metabolizing enzyme activity; as well as immunoassays that detect or quantify the expression of the enzyme. After expression of the desired enzyme is demonstrated in the plant, the plant is grown. Two or more generations may be grown to ensure that the subject phenotypic characteristic is stably maintained and inherited.

To identify the desired phenotypic characteristic, transgenic plants that contain and express a given sugar-metabolizing enzyme transgene are compared to control plants. Suitably, transgenic plants are selected by measurement of enzyme activity in a sink tissue selected, for example, from tuber, fruit and/or root. The sugar-metabolizing enzyme activity may be periodically measured from various stages of growth through senescence and compared to that of control plants. Plants or plant parts having increased or decreased enzyme activity compared to controls at one or more periods are selected. The activity can be compared to one or more other traits including enzyme type, transcription control element type, translation initiation type, termination region type, transgene copy number, transgene insertion and placement.

When evaluating a phenotypic characteristic associated with enzyme activity, the transgenic plants and control plants are preferably grown under growth chamber, greenhouse, open top chamber, and/or field conditions. Identification of a particular phenotypic trait and comparison to controls is based on routine statistical analysis and scoring. Statistical differences between plants lines can be assessed by comparing sugar-metabolizing enzyme activity between plant lines within each tissue type expressing the enzyme. Expression and activity are compared to growth, development and yield parameters which include plant part morphology, color, number, size, dimensions, dry and wet weight, ripening, above- and below-ground biomass ratios, and timing, rates and duration of various stages of growth through senescence, including vegetative growth, fruiting, flowering, and soluble carbohydrate content including sucrose, glucose, fructose and starch levels as well as other endogenous sugar levels and alien sugar levels. To identify transgenic plants having other traits, the plants can be tested for photosynthetic and metabolic activity, as well as end-product synthesis. For example, material isolated from transgenic plant cells and plant parts such as tuber, fruit and root are measured for end-products such as starch, sucrose, glucose, fructose, sugar alcohols as well as other endogenous sugars and alien sugars following standard protocols. Sweetness based on sugar content, particularly fructose and sucrose, can be tested as well. For some plants, it may be necessary to modify growth conditions to observe the phenotypic effect. As an example, oxygen, carbon dioxide and light can be controlled and measured in an open gas chamber system, and carbon partitioning measured by $C^{14}$ labeling of carbon dioxide or other metabolic substrates. Carbon partitioning also can be determined in extracts from fruit, leaf and/or root by chromatographic techniques or by Brix using a sugar refractometer. These characteristics also can be compared against or induced by growth conditions which vary gas exchange parameters, light quality and quantity, temperature, substrate and moisture content between lines within each type of growing condition.

Production of Fermentation Products

The soluble carbohydrates produced by the transgenic plants of the present invention will include fermentable carbohydrates, which can then be used as fermentation feedstocks for ethanol ethanol-containing beverages, and other fermentation products such as foods, nutraceuticals, enzymes and industrial materials. The methods for fermentation using plant-derived carbohydrate feedstocks are well known to those skilled in the art, with established processes for various fermentation products (see for example Vogel et al. 1996, *Fermentation and Biochemical Engineering Handbook: Principles, Process Design, and Equipment*, Noyes Publications, Park Ridge, N.J., USA and references cited therein). In one embodiment, the soluble carbohydrates may be extracted by crushing the plant, or by diffusion from the plant tissues into water or another suitable solvent. The resulting juice or extract containing the soluble carbohydrates may be used directly as a substrate for fermentation or bioconversion in a batch, continuous, or immobilized-cell process. Alternatively, part of the soluble carbohydrates may be recovered for other uses and the unrecovered components used as fermentation feedstocks, as in the case of molasses remaining after recovery of most of the sucrose by crystallization.

In order that the invention may be readily understood and put into practical effect, particular preferred embodiments will now be described by way of the following non-limiting examples.

EXAMPLES

Example 1

Expression of Three Sucrose Isomerase Genes in *E. coli*

Sequences of sucrose isomerase genes UQErw (*Erwinia rhapontici*) (SEQ ID NO:24), UQ14S (SEQ ID NO:26) and UQ68J (SEQ ID NO:25) are described in Birch and Wu (2002). Three pairs of primers were designed for subcloning the three sucrose isomerase (SI) genes into expression vector pET 24b (Novagen). By PCR, non-coding regions and leader sequences were deleted and an artificial start codon was incorporated.

Each forward primer: 1) includes a start codon, 2) creates a plant-like context for the translation start, 3) incorporates a BamHI restriction site for easily cloning and matching the open reading frame of the gene. Each reverse primer incorporates a KpnI restriction site and includes a stop codon.

The primer sequences are presented in Table 1 below.

TABLE 1

| | | |
|---|---|---|
| UQErw forward: | 5'-gga tcc aac aat ggc aac cgt tca gca atc aaa tg-3' | [SEQ ID NO:1] |
| UQ14S forward: | 5'-gga tcc aac aat ggc aac cgt tca caa gga aag tg-3' | [SEQ ID NO:2] |
| UQ68J forward: | 5'-gga tcc aac aat ggc aac gaa tat aca aaa gtc c-3' | [SEQ ID NO:3] |
| UQErw reverse: | 5'-ata ggt acc tta ctt aaa cgc gtg gat g-3' | [SEQ ID NO:4] |
| UQ14S reverse: | 5'-ata ggt acc tta ccg cag ctt ata cac acc-3' | [SEQ ID NO:5] |
| UQ68J reverse: | 5'-ata ggt acc tca gtt cag ctt ata gat ccc-3' | [SEQ ID NO:6] |

High fidelity DNA polymerase pfu (Stratagene) was used for PCR. The PCR products were directly cloned into vector pCR®2.1 using the TOPO™TA Cloning® Kit (Invitrogen). The three sucrose isomerase genes in the pCR®2.1 vector were excised and cloned into pGEM®-3Zf(+) then into pET 24b (Novagen) for expression in *E. coli* strain BL21(DE3).

Example 2

Conversion Efficiency from Sucrose into Isomaltulose by Sucrose Isomerases Expressed in *E. coli*

Fifteen cultures per SI construct (from Example 1) in BL21 (DE3) were set up in 5 mL LB medium with 50 μg/mL kanamycin. Cells were grown at 37° C. with shaking at 225 rpm. Six to ten cultures per construct, with $OD_{600}$ 1.000±0.005, were selected for further induction. After 0.5 mL was sampled from each culture, IPTG was added to the culture to a final concentration of 1.0 mM. Incubation of the cultures was continued for another 3 hours. The induced cultures only with $OD_{600}$ 1.750±0.005 were further selected for quantification of conversion efficiency from sucrose into isomaltulose, allowing analysis of three replicate cultures per construct.

A 1.0 mL aliquot of each culture was centrifuged, then the pellet was resuspended in 0.4 mL of 50% sucrose solution buffered with 35.8 mM Na citrate and 128.4 mM Na phosphate (pH 6.0). The suspension was incubated at 37° C. for 48 hours with shaking at 225 rpm. The reaction was assayed for isomaltulose conversion by CE analysis as described below (Examples 12 and 13). Conversion efficiency, expressed as isomaltulose/(isomaltulose+sucrose)×100, was calculated from sucrose peak area and isomaltulose peak area normalized against standards of known concentration, using the software of the Beckman P/ACE 5000 Series CE System.

Example 3

Construct DNA for Expression of the Cytosol-Targeted SI Genes, Driven by Promoter Ubi (pU3ZErw, pU3Z14S or pU3Z68J)

The Ubi promoter from the maize ubi-1 gene (Christensen and Quail, 1996, *Transgen. Res.* 5, 213-218) was employed. For cytoplasmic gene expression in sugarcane cells, the inserts of different SI genes from the pET 24b vectors (Example 1) were further cloned between the Ubi promoter and the *Agrobacterium nos* polyadenylation region (Bevan et al., 1983, *Nature* 304, 184-187) in plasmid vector pU3Z, to construct pU3ZErw, pU3Z14S or pU3Z68J plasmids.

Example 4

Construct DNA with an ER Leader Peptide, an N-Terminal Propeptide (NTPP) Vacuole Targeting Signal, and UQ68J SI with or without 6×His Tag, Driven by Promoter Ubi (pU3ZERsN68J or pU3ZERsN68J-His)

Vector Preparation

A vector with Ubi promoter, 21 amino acid sporamin ER leader peptide, 16 amino acid sporamin NTPP vacuole targeting signal peptide, MGUS reporter gene, and *Agrobacterium nos* polyadenylation region (Gnanasambandam & Birch, 2004) was partially digested with restriction enzymes of NcoI and SacI, and the resulting fragment comprising the vector backbone with Ubi promoter, ER leader peptide and NTPP was purified by gel electrophoresis.

Insert Preparation by PCR

Forward primer with a 5' BglII restriction site (gtagatctC GCA ACG AAT ATA CAA AAG TCC G) (SEQ ID NO: 11), reverse primer with a 5' SacI restriction site (aagagcTCA GTT CAG CTT ATA GAT CCC) (SEQ ID NO: 12) and reverse primer His-tagged with a 5' SacI restriction site (aa gagcTCA GTG GTG GTG GTG GTG GTG GTF CAG CTT ATA GAT CCC) (SEQ ID NO: 13) were designed for amplification of the UQ68J SI gene without the periplasmic leader sequence. The UQ68J SI gene in pET24b vector was used as DNA template. High fidelity Pfu DNA polymerase (Stratagene) was employed in a PCR reaction, with the forward primer and one of the reverse primers. The PCR products were directly cloned into vector pCR®2.1 using the TOPO™TA Cloning® Kit (Invitrogen). The insert was excised from the pCR®2.1 vector at the BglII site and SacI site and purified by gel electrophoresis.

Linker Preparation

Forward single chain of oligo (GAT Ggt cga aac tcc agt a) (SEQ ID NO: 21) and reverse single chain oligo (ca gct ttg agg tca tCA TG) (SEQ ID NO: 22) were designed to form a linker with NcoI and BglII overhangs. A mixture of 5 μL of each oligo at 500 μM was heated at 95° C. for 5 minutes then cooled to room temperature over 3 hours.

Ligation and Transformation

The vector, insert and linker were ligated and transferred into *E. coli* Top 10 competent cells (Invitrogen).

Example 5

Construct DNA with an ER Leader Peptide, UQ68J SI and a C-Terminal Propeptide (CTPP) Signal with or without 6×His Tag, Driven by Promoter Ubi (pU3ZERc68JC OR pU3ZERc68JC-His)

Insert Preparation of UQ68J SI Gene Tailed with CTPP

Forward primer with a BglII restriction site (gtagatctC GCA ACG AAT ATA CAA AAG TCC G) (SEQ ID NO: 11), reverse primer with 21 bp encoding 7 amino acid (GLLVDTM) (SEQ ID NO: 23) vacuole targeting signal with a SacI restriction site (gagcTCA CAT AGT ATC GAC TAA GAG ACC GTT CAG CTT ATA GAT CC) (SEQ ID NO: 14) and reverse primer encoding His-tagged GLLVDTM (SEQ ID NO: 23) with a SacI restriction site (gagcTCA GTG GTG GTG GTG GTG GTG CAT AGT ATC GAC TAA GAG ACC GTT CAG CTT ATA GAT CC) (SEQ ID NO: 15) were designed for amplification of the UQ68J SI gene without the periplasmic leader sequence. The UQ68J SI gene in pET24b vector was used as DNA template. High fidelity Pfu DNA polymerase (Stratagene) was employed in a PCR reaction, with the forward primer and one of the reverse primers. The PCR products were directly cloned into vector pCR®2.1 using the TOPO™TA Cloning® Kit (Invitrogen). The insert was excised from the pCR®2.1 vector at the BglII site and SacI site and purified by gel electrophoresis.

ER Leader Peptide Prepared by PCR and Inserted into pSE420 to Make an Intermediate Vector Based on the DNA sequence of the ER leader peptide from tobacco chitinase, a forward primer with a BamHI site (aa ggatccA ATG AGG CTT TGA AAA) (SEQ ID NO: 16) and a reverse primer with a BglII restriction site (aaa gat ctC GCC GAG GCA GAA AGC AG) (SEQ ID NO: 17) were designed. High fidelity Pfu DNA polymerase (Stratagene) and pER-RGUS-CTPP (Gnanasambandam & Birch, 2004) as template were used to amplify the DNA encoding 23 amino acid ER leader element. The PCR products was purified by ethanol precipitation, digested by BamHI and BglII, treated with calf intestinal alkaline phosphatase and purified by 1.5% agarose gel electrophoresis. The product was ligated into the BamHI and BglII site of vector pSE420 (Invitrogen), and the desired orientation of the insert was confirmed by DNA sequencing. The resulting plasmid was further digested with BglII and SacI, and the largest fragment was recovered as an intermediate for insertion of the UQ68J SI gene.

Ligation of the UQ68J SI with CTPP Into the pSE420-ER Intermediate Vector and Transformation The 68J SI tailed with CTPP was ligated into the intermediate vector, downstream from the ER leader peptide. The ligation products were transferred into Top 10 (Invitrogen) competent cells. The resulting plasmid was digested with restriction enzymes BamHI and SacI and the insert was recovered for ligation.

Preparation of pU3Z Vector with Promoter Ubi and the *Agrobacterium nos* Polyadenylation Region Vector pU3Z68J (Example 3) was digested with restriction enzymes BamHI and SacI. The vector backbone fragment with promoter Ubi and the *Agrobacterium nos* polyadenylation region was recovered for ligation.

Ligation of the Insert Including Fragments Encoding ER Leader, UQ68J SI and CTPP into pU3Z Vector and Transformation The ER-68J-CTPP fragment from the intermediate vector was ligated into pU3Z vector between the BamHI and SacI sites. The ligation products were transferred into Top 10 competent cells.

Example 6

Construct DNA with an ER Leader Peptide, an NTPP Vacuole Targeting Signal, UQ68J SI and a CTPP Signal, Driven by Promoter Ubi (pU3ZERsN68JC)

Vector Preparation

Plasmid construct pU3ZERsN68J prepared in Example 4 was digested by BglII and SacI. The fragment containing the vector backbone, ER leader, NTPP and *Agrobacterium nos* polyadenylation region was recovered for ligation.

Insert Preparation

Plasmid construct pU3ZERc68JC prepared in Example 5 was digested by BglII and SacI. The UQ68J SI gene fragment tailed with CTPP was recovered for ligation.

Ligation and Transformation

The above mentioned vector and insert fragments were ligated and transferred into Top 10 competent cells.

Example 7

Cloning of Sugarcane Stem-Specific Promoter 67B

Based on the DNA sequence of the sugarcane stem specific promoter P67 (Birch & Potier, 2000), a forward primer (tgg agc tcg atg gga ggt gct cg) (SEQ ID NO: 18) with a SacI restriction site and a reverse primer (atg gat cct gta cta gtt atg gca gct ac) (SEQ ID NO: 19) with a BamHI restriction site were designed to amplify potential promoter homologues using genomic DNA from sugarcane cultivar Q117 as template. Total genomic DNA was isolated from young Q117 leaves according to Wu et al. (2000, Plant Journal, 22: 495-502) with some modifications. Briefly, 2 g leaves were ground in liquid nitrogen. The frozen powder was suspended in 14 mL of extraction buffer (1.4 M NaCl, 20 mM EDTA, 0.1 M Tris-HCl, pH 8.0, 3% CTAB and 1% 2-mercaptoethanol) at 65° C. for 30 minutes. An equal volume of chloroform:isoamyl alcohol (24:1) was added, mixed, then centrifuged for 10 minutes at 10,000×g at 4° C. The aqueous layer was mixed with an equal volume of isopropanol, and the DNA was pelleted by centrifugation at 15,000×g for 15 minutes at 4° C. The pellet was washed with 70% ethanol, dried briefly to remove residual ethanol, and dissolved in TE buffer. The products from three independent amplifications using high fidelity DNA polymerase Pfu (Strategene) were directly cloned into vector pCR®2.1 using the TOPO™TA Cloning® Kit (Invitrogen). Plasmid DNAs were isolated and sequenced from 15 transformed bacterial colonies. Sequencing results showed that 5 out of the 15 colonies had an identical sequence that is different from the P67 sequence isolated by Birch & Potier (2000). The sequence isolated by Birch & Potier (2000) is therefore designated promoter 67A. The additional sequence presented here is designated promoter 67B.

Example 8

Construct DNA with Gus Reporter Gene Driven by Promoter 67B (p67BGUS)

The plasmid pCR®2.1 with a insert (prepared in Example 7) was digested by BamHI and SacI to release promoter 67B, which was used to replace promoter 67A in plasmid p67AGUS (Birch & Potier, 2000).

Example 9

Construct DNA with UQ68J SI Gene Driven by Promoter 67B (p67B68J)

Insert Preparation

The UQ68J SI gene was excised at the BamHI and KpnI sites from the pCR®2.1 intermediate described in Example 1, and recovered for ligation.

Preparation of a Vector with Promoter 67B, Multiple Cloning Site and *Agrobacterium nos* Polyadenylation Region (i) Promoter 67B from Example 7 was inserted at the BamHI and SacI sites in vector pSE420 (Invitrogen), then excised between BamHI and Hind III sites for ligation. (ii) The *Agrobacterium nos* polyadenylation region was released from vector pBI101(Clontech) at SacI and EcoRI sites, and inserted into the same sites in vector pGEM®3Zf(+). (iii) The P67B sequence from (i) was inserted into the BamHI and Hind III sites of the intermediate vector from (ii). The resulting vector—with pGEM®3Zf(+) backbone, promoter 67B, multiple cloning site and *Agrobacterium nos* polyadenylation region—was digested with BamHI and KpnI, and recovered for ligation.

Ligation and Transformation

The UQ68J SI gene was ligated between promoter 67B and the polyadenylation region in the intermediate vector to complete p67B68J, which was transferred into Top 10 competent cells.

Example 10

Construct DNA with UQ68J SI Gene Driven by Promoter 67A (p67A68J)

Promoter 67A Preparation by PCR

Forward primer and reverse primer were the same as those for cloning of promoter 67B in Example 7. The 67A promoter in p67AGUS (Birch & Potier, 2000) was used as DNA template. High fidelity Pfu DNA polymerase (Stratagene) was employed in PCR reaction. The PCR products were directly cloned into vector pCR®2.1 using the TOPO™TA Cloning® Kit (Invitrogen). Promoter 67A was excised from the pCR®2.1 vector at the BamHI site and SacI site and recovered for ligation.

Preparation of SI Gene with a Vector Backbone by Digestion

Plasmid p67B68J prepared in Example 9 was partially digested by BamHI and SacI. The fragment comprising the vector backbone with UQ68J Si gene and the *Agrobacterium nos* polyadenylation region was recovered for ligation.

Ligation and Transformation

Promoter 67A was ligated into the vector upstream of the UQ68J SI gene. The ligation products were transformed into Top 10 competent cells.

Example 11

Particle Bombardment

Plasmids with the SI genes (pU3ZErw, pU3Z14S, pU3Z68J, pUERsN68J, pUERsN68J-His, pUERc68JC, pUERc68JC-His, pUERsN68JC, p67A68J or p67B68J) and the aphA construct pEmuKN (as a selectable marker) were isolated by alkaline extraction, and dissolved in TE buffer. Plasmid intactness and absence of genomic DNA or RNA were checked by gel electrophoresis and concentration was measured by spectrophotometry.

The Ubi-sucrose isomerase (UbiSI) gene construct and selectable marker construct were co-precipitated onto tungsten microprojectiles and introduced into sugarcane callus, followed by selection for transformed callus, and regeneration of transgenic plants, essentially as described previously (Bower et al., 1996; Birch, 2000).

Precipitation reactions were conducted by adding the following at 4° C. in turn to a 1.5 mL microfuge tube: 5 µL pEmuKN plasmid DNA (1 mg/mL), 5 µL UbiSI plasmid DNA (1 µg/µL), 50 µL tungsten (Bio-Rad M10, 100 µg/µL), 50 µL $CaCl_2$ (2.5 M), 20 µL spermidine (100 mM free base). The preparation was mixed immediately after addition of each reagent, with minimal delay between addition of $CaCl_2$ and spermidine. The tungsten was then allowed to settle for 5 minutes on ice, before removal of 100 µL of supernatant and resuspension of the tungsten by running the tube base across a tube rack. Suspensions were used within 15 minutes, at a load of 4 µL/bombardment, with resuspension of the particles immediately before removal of each aliquot. Assuming the entire DNA is precipitated during the reaction, this is equivalent to 1.3 µg DNA/bombardment, on 667 µg tungsten/bombardment.

Embryogenic callus from sugarcane cultivar Q117 was used for bombardment. Particles were accelerated by direct entrainment in a helium gas pulse, through the constriction of a syringe filter holder into the target callus in a vacuum chamber. The tissue was osmotically conditioned for four hours before and after bombardment. After 48 hours recovery on solid medium without antibiotics, the bombarded callus was transferred to medium with 45 mg/L Geneticin® for selection, callus development and plant regeneration.

Example 12

Sugarcane Growth Conditions and Growth Rate Measurement

Sugarcane cultivar Q117 and its transgenic lines expressing the SI gene were grown in 20 cm diameter pots containing UC potting mix B (1 $m^{-1}$ sand, 0.5 $m^{-1}$ peat and 12.45 kg of fertilizer mix comprising by weight 12 parts 'blood and bone': 2 parts potassium nitrate: 1 part potassium sulfate: 12 parts superphosphate: 20 parts dolomite: 12 parts hydrated lime: 6 parts gypsum: 2.4 parts 'micromax'); in a containment glasshouse under natural light intensity, at 28° C. With watering twice a day. For plants regenerated from callus (first vegetative generation) or grown from subsequent stem cuttings (second and third vegetative generations), only one stalk was grown per pot. For ratoon plants, after cutting the previously grown stalks off at the pot surface, two stalks were allowed to grow from buds below the surface without repotting (also yielding second and third vegetative generations). Each pot was fertilized with Osmocote® at 5 g per month for the first and the second months, then 10 g per month. Height (from the pot surface to the top visible dewlap), stem diameter (first internode above ground), number of nodes (counting the node subtending the leaf with the top visible dewlap as number 1) and fresh weight were recorded monthly for the first three months, then fortnightly.

Example 13

Sample Preparation for Capillary Electrophoresis

To remove ionic materials, culture supernatants and plant tissue extracts were passed through strong cation and anion exchange columns (Varian Bond Elut-SCX and SAX). Samples and rinses were forced through the columns with the aid of a syringe.

The columns were preconditioned by rinsing with one volume of methanol, followed by one volume of water. Bacterial culture supernatant (from example 2) was diluted 150-fold using sterile Milli-Q (SMQ) water, then 1 mL of the diluted supernatant was passed through SAX and SCX columns and the unadsorbed eluate was collected in a 1.5 mL tube.

Example 14

Capillary Electrophoresis

Separation by high performance capillary electrophoresis (HPCE), was performed in a Beckman P/ACE 5000 Series CE System using absorbance at 254 nm for sample detection. Capillaries were bare, fused silica I.D. 50 µm, O.D. 363 µm (Supelco Cat. #70550-U). Total capillary length was 77 cm, and inlet to detector window was 69 cm. The capillary detector window was made by burning the coating off the capillary using a match, and wiping with methanol.

An alkaline copper sulfate electrolyte buffer (EB, composed of 6 mM copper (II) sulfate and 500 mM ammonia, pH 11.6) was employed to resolve sucrose and isomaltulose, in addition to other sugars including glucose and fructose that are expected in cell extracts. Separation and direct UV detection of neutral sugars is facilitated by the chelation reaction of the sugars with copper (II) under alkaline conditions. EB was made fresh at the beginning of each day and degassed under vacuum for 15 min before use.

To achieve maximum reproducibility of migration times, the capillary was conditioned daily before use, by the following rinsing procedure: 2 min with water, 10 min 0.1 M HCl, 2 min water, 10 min 0.1 M NaOH, 2 min water, 15 min 0.5 M ammonia and 2 min water. All solutions were dissolved/diluted in SMQ water and filtered through a 0.45 µm Micropore filter. The capillary was then rinsed with EB for 15 min before the first sample and 10 minutes between samples. Runs were for 30 min at 25 KV. Standards (consisting of sucrose and isomaltulose plus other sugars as appropriate to the experiment) were run before the first, and after the last sample in each batch, so that differences in migration times due to factors such as EB depletion or capillary heating could be measured and corrected. Each sugar concentration in the samples was calculated by comparison of peak area against to the standards of known molar concentration.

Example 15

Sample Preparation from Intracellular and Extracellular Spaces of Three Radial Zones in Sugarcane Stem Tissue for HPLC-ED A 1.5 cm long section was cut from the middle of an internode, and samples were collected from three radial zones (center, middle, and outer). The center zone was a cylinder with diameter of 6 mm, sampled using a sharp cork borer. The middle zone was the surrounding band of 4 mm width, obtained using a 10 mm diameter cork borer. The outer zone was collected by cuffing a band 4 mm thick immediately under the rind. The dissected zones were separately placed in GelSpin™ filters (Mo Bio Laboratories) without membranes for centrifugal collection of fluids. To remove fluids from cut surface cells, the samples were centrifuged at 150×g for 10 minutes at 4° C., and the filtrate was discarded. After another centrifugation of 600×g for 4 minutes at 4° C., the filtrate was collected as the fluid from extracellular spaces. To avoid contamination of the intracellular fluids, the samples were centrifuged at 1,500×g for 5 minutes at 4° C. and the filtrate was discarded. The samples were then frozen in liquid nitrogen and warmed to room temperature to disrupt cell membranes, and centrifuged at 10,000×g for 10 minutes at 4° C. This filtrate was collected as intracellular fluid. Both intra- and extra-cellular fluids were heated at 100° C. for 5 minutes after collection and centrifuged at 15,000×g for 10 minutes to remove insoluble material. The supernatant was diluted 1,000-fold using sterile Milli-Q water, and analyzed by HPLC-E.

Example 16

Measurement of Sugar Concentrations by HPLC-ED

Resolution and quantification of sucrose, isomaltulose, trehalulose, glucose and fructose was achieved by isocratic HPLC at high pH (100 mmol l$^{-1}$ KOH), using a Dionex BioLC system with PA20 analytical anion exchange column and quad waveform pulsed electrochemical detection, with calibration against a dilution series of sugar standards for every sample batch (Wu & Birch, 2004). This method was used for all experiments with the SI gene coupled to NTPP and/or CTPP signals, and for all experiments with the SI gene driven by the P67 promoter, and sugar concentrations were corrected for dilutions in the procedure to give results equivalent to concentrations in juice.

Example 17

Measurement of Sugar Concentrations in Sugarcane Tissues by Capillary Electrophoresis Sugarcane tissue samples were collected, weighed, snap frozen with liquid nitrogen, then 3 µL of SMQ water per milligram FW was added and the tube was boiled for 20 minutes (with a small hole pierced in the top of the microcentrifuge tube to prevent the lid from "popping"). After a brief spin to bring all liquid to the base of the tube, the solution was transferred to a fresh tube and centrifuged at 16,000×g for 10 min at 4° C. to remove denatured proteins. The supernatant was passed through BondElut™ SCX and SAX, and CE analysis was performed as described in Example 14. This method was used for experiments with the Ubi-promoter/cytosolic SI transformants, and sugar concentrations were corrected for dilutions in the procedure to give results equivalent to concentrations in juice.

Example 18

Leaf Chlorophyll, Fresh Weight, Dry Weight and Water Content Measurements

Sugarcane leaves and attached nodes were numbered from top to bottom, assigning the leaf with the top visible dewlap number 1. Measurements were made on at least three replicate plants per line. For each replication of chlorophyll or weight measurement, four discs were taken using a 5 mm diameter hole punch, from the leaf blade at 1/10 leaf length from the dewlap. The four discs were put into a preweighed 1.5 mL microcentrifuge tube, which was immediately weighed and placed into liquid nitrogen.

For dry weight and water content measurements, the leaf discs were oven-dried at 70° C. to a constant dry weight. Water content was calculated as:

(fresh weight−dry weight)/fresh weight*100

For chlorophyll estimation, the frozen leaf discs were ground into powder, extracted with 80% acetone in the dark and then centrifuged at 12,000×g for 10 minutes at 4° C. Absorbance was measured at 664 nm and 647 nm. Chlorophyll a, chlorophyll b and total chlorophyll concentrations (Graan and Ort, 1984) were calculated as:

Chlorophyll $a$(mM)=13.19$A_{664}$−2.57$A_{647}$

Chlorophyll $b$(mM)=22.10$A_{647}$−5.26$A_{664}$

Total chlorophyll(mM)=7.93$A_{664}$+19.53$A_{647}$

Example 19

Electron Transport Rate of Photosystem II in Sugarcane Leaves

Photosynthetic electron transport rate was estimated from the fluorescence light curve generated using a fiberoptic MINI-PAM/F (Heinz Walz GmbH, Germany) and leaf-clip holder 2030-B positioned at the 1/10 of the leaf length from the dewlap. Parameters on the MINI-PAM of light intensity, saturation pulse intensity, saturation pulse width, leaf absorption factor and illumination time were set at 8, 8, 0.8, 0.84 and 10 s respectively. Internal temperature of the MINI-PAM was controlled between 25-30° C. during measurement. Fluorescence was measured on equivalent leaves from at least three replicate plants of each line.

Example 20

$CO_2$ Fixation Rate of Sugarcane Leaves

An LI-6200 portable photosynthesis system (LI-COR, USA) with a 250 cm$^3$ leaf chamber was employed to measure $CO_2$ fixation rates in the same leaves used for fluorescence measurements.

Example 21

Total RNA Extraction from Sugarcane Tissues and RNA Gel Blot Analysis

Total RNA was isolated from number 1-2 leaves or number 3-4 stem of 6-month-old sugarcane plants, using the method of Bugos et al. (1995). Briefly, 10 g of frozen tissue was ground with liquid nitrogen to fine powder. Extraction buffer (20 ml of 100 mM Tris-HCl pH 9.0, 200 mM NaCl, 15 mM EDTA, 0.5% Sarkosyl, 100 mM 2-mercaptoethanol) was added followed by homogenization for 5 min. Buffer-equilibrated phenol (20 ml) and 4 ml of chloroform:isoamyl alcohol (24:1) was added, followed by homogenization for 2 min. Sodium acetate (1.4 ml of 3 M, pH 5.2) was added and homogenized for 30 seconds. The extract was cooled on ice for 15 minutes and centrifuged at 10,000×g for 10 minutes at 4° C. The aqueous part was transferred to a fresh tube and an equal volume of isopropanol was added. After centrifugation at 10,000×g for 10 minutes at 4° C., the pellet was washed with 70% ethanol and vacuum dried.

The pellet was dissolved in water and 8M LiCl was added to a final concentration of 2M. After incubation on ice for 3 hours, the RNA was precipitated by centrifugation at 14,000×g for 10 minutes at 4° C. The RNA pellet was washed with 70% ethanol, vacuum dried, dissolved in water and the concentration was measured with a spectrophotometer.

Thirty µg total RNA per lane was fractionated by electrophoresis in a 2.2 M formaldehyde and 1.0% agarose gel, and blotted onto a Hybond N+ nylon membrane (Amersham Pharmacia BioTech). The blot was prehybridized with modified Church and Gilbert hybridization solution (7% SDS, 10 mM EDTA and 0.5M phosphate buffer, pH7.2) for 2 hours, then hybridized with randomly primed $^{32}$P-labeled probes from full length UQ68J SI cDNA at 65° C. overnight. After hybridization, the membrane was rinsed with 2×SSC, 0.1% SDS at 23° C., washed at 65° C. with 2×SSC, 0.1% SDS for 15 minutes, 1×SSC, 0.1% SDS for 15 minutes and 0.1×SSC, 0.1% SDS for 15 minutes, wrapped with plastic film, and exposed to a phosphorimager plate (Molecular Dynamics) overnight for latent image accumulation.

Example 22

Genes Other than Sucrose Isomerases that May be Useful to Practice the Invention Various genes may be introduced to achieve the partial conversion of a substrate compound that is normally sensed by the organism into a product compound that is not perceived in an equivalent manner within the organism, with the effect that metabolic flows are altered, resulting in the accumulation of higher yields of desired compounds.

Where the desired compounds are carbohydrates, useful genes may include those encoding carbohydrate-active enzymes for example isomerases (EC 5.4) or transglycosidases (EC 3.2) or glycosyltransferases (EC 2.4) including glucosyltransferases and fructosyltransferases, such as amylosucrase (EC 2.4.1.4), dextransucrase (EC 2.4.1.5), levansucrase (EC 2.4.1.10), or cyclodextrin glucosyltransferase (EC 2.4.1.19), and variants of these enzymes that preferentially synthesize oligosaccharides alien to the modified organism (Demuth et al. 2002; Martin et al. 2004; Park et al. 2003; Plou et al. 2002; van der Veen et al. 2004).

Alternatively, genes encoding enzymes that result in the partial conversion of sugars or endogenous sugar derivatives into alien sugar derivatives such as sugar alcohols (Saha 2004; Zhifang and Loescher 2003) may prove useful. The choice of gene should be informed by consideration of the availability and metabolic role in the target organism of the corresponding substrates and cofactors, and on the capacity of the organism to sense and metabolize the product. The invention may be practiced in organisms with substantially different physiologies and it will be recognized by persons of skill in the art that the optimal expression patterns of alternative genes, which may be introduced to achieve the effect of the invention in different species, can be determined by routine experimentation.

Example 23

Plants Other than Sugarcane that May be Useful to Practice the Invention

The invention may also be practiced in other plants grown for the harvest of soluble sugars, for example sweet sorghum or sugarbeet, or in plants where sweetness conferred by soluble sugars is an important trait, for example cereals such as sweet corn, legumes such as peas, and fruits such as grapes, tomatoes and bananas. Processes for the introduction of genes for expression in these plants are thoroughly documented in the public domain, for example the methods of (Cortina 2004; Ganapathi et al. 2001; Grant et al. 2003; Hermann et al. 2001; Jeoung et al. 2002; Joersbo et al. 2000; Polowick et al. 2002; Tadesse et al. 2003; Vidal et al. 2003; Zhang et al. 2001; Zhang et al. 2002), and well known to those skilled in the art.

Sweet sorghum may be transformed with the expression constructs described herein, in the examples given using sugarcane as the model plant species. In other species, the constructs may be adjusted by the substitution of appropriate promoters, and signal sequences. For example the CaMV 35S promoter may be used for constitutive expression in dicotyledonous species. Suitably, a promoter may be used that is preferentially expressed in the desired sink tissue; for example the patatin B33 promoter for expression in the storage root of sugar beet, or a fruit-specific or ripening-associated promoter promoter for other species (Lessard et al. 2002). Other signal sequences may be used to partition the gene product to varying degrees between the sucrose storage compartment and metabolic compartment within the cell, for example the NTPP from the patatin B33 gene or other known vacuolar signals (Vitale and Raikhel 1999).

Results and Discussion Relating to the Examples

Cytosol-Targeted SI Expression Driven by Promoter Ubi

Figure 1:
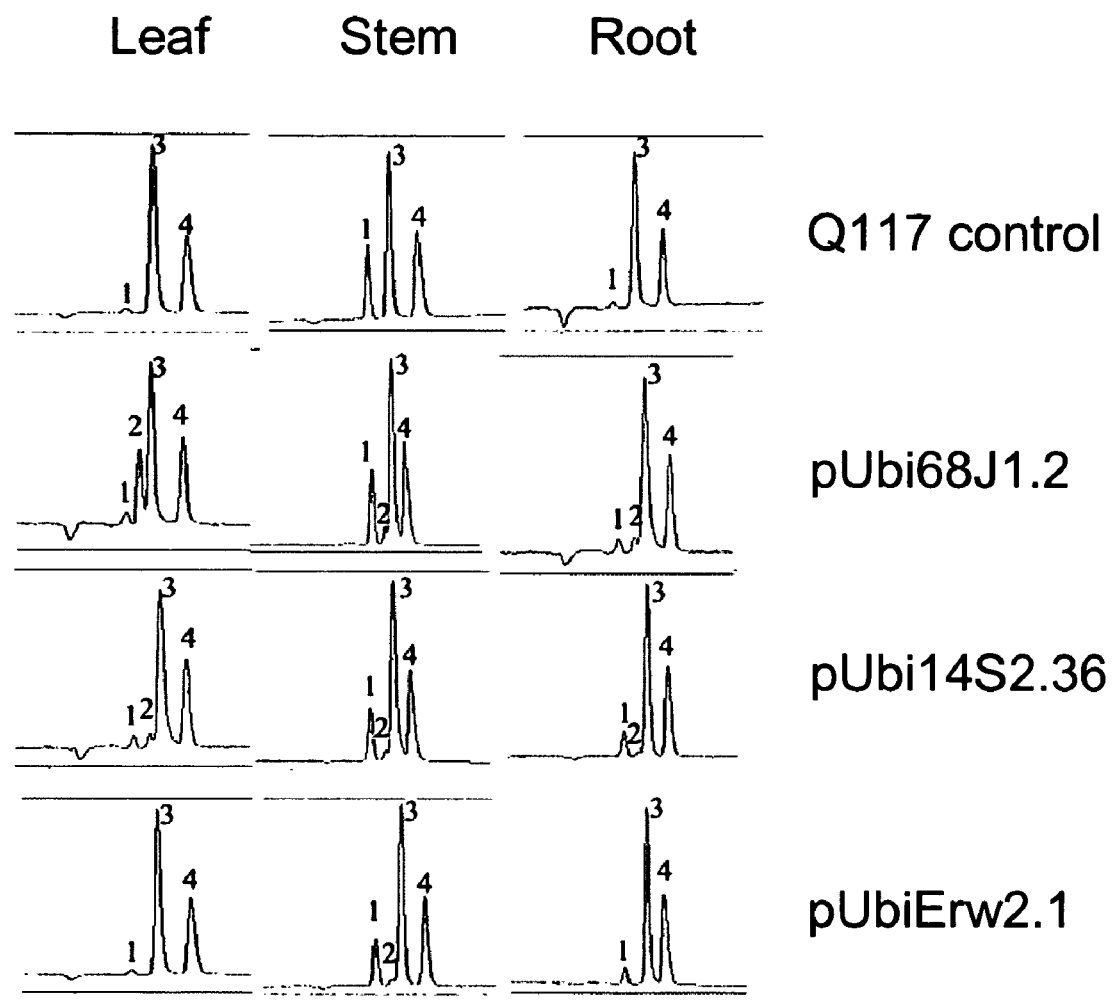
FIG. 1 is a graphical representation showing capillary electrophoresis of the soluble sugars of leaf (#3), stem (internode #12) and young root tissues from a Q117 control plant or plants from transgenic lines pUbi68J1.2, pUbi14S2.36 and pUbiErw2.1. The sampled plants were 6 months old with 12 to 13 nodes. The transgenic lines were first vegetative generation from callus. Peaks are: 1 sucrose, 2 isomaltulose, 3 fructose and 4 glucose.
Figure 2:
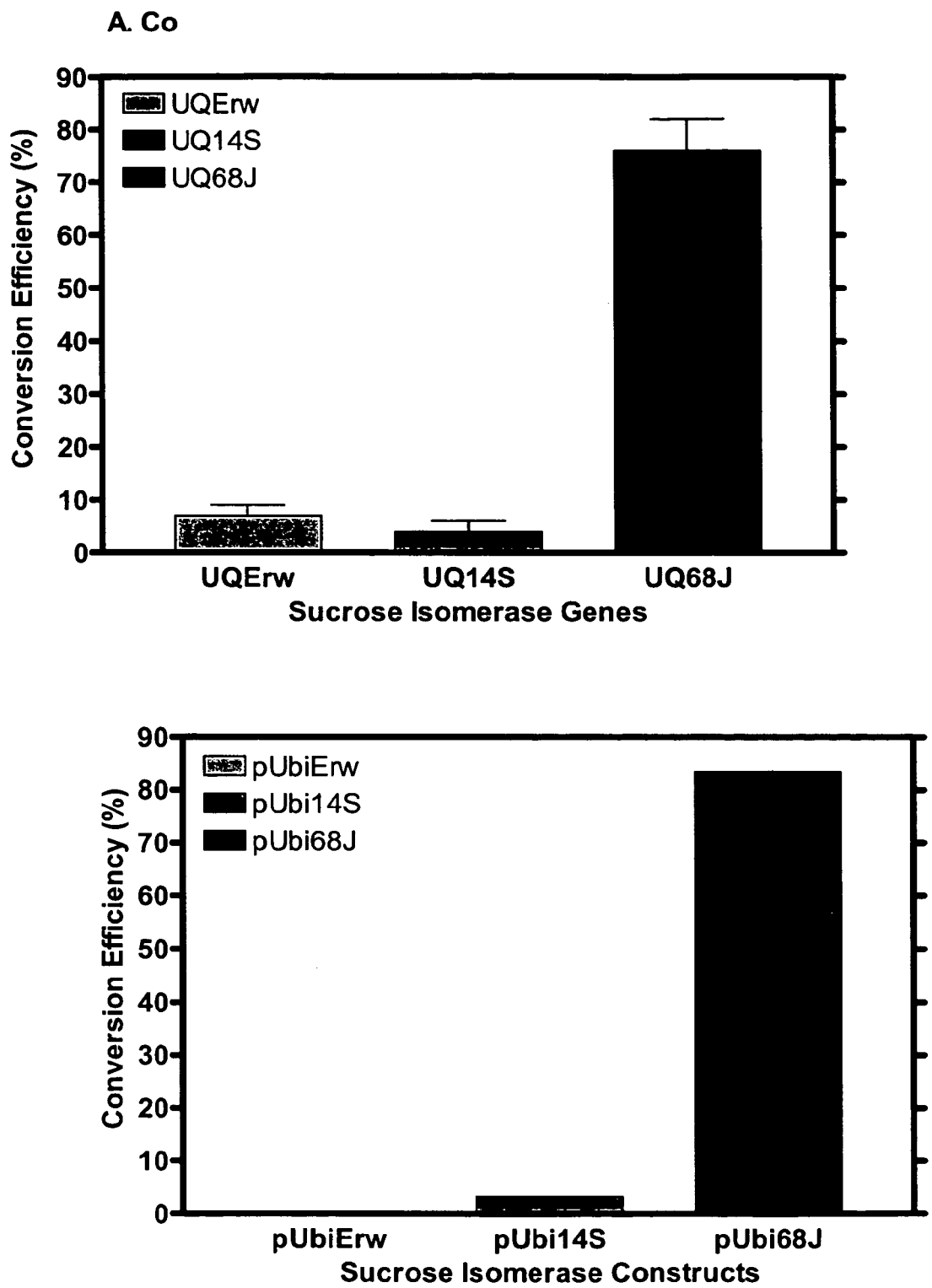
FIG. 2 is a graphical representation showing the conversion efficiency of different sucrose isomerase genes in E. coli (A) and stems of transgenic sugarcanes (B). Conversion efficiency is defined as isomaltulose/(sucrose+isomaltulose)*100. Results in A are means with standard errors from three replicate cultures. Results in B are maximum stem conversion efficiencies from 11 lines of pUbiErw, 11 lines of pUbi14S and 9 lines of pUbi68J. The sampled sugarcanes were 6 months old with 12 to 15 nodes, in their first vegetative generation from callus.

Isomaltulose was detected from all tissues of Ubi-SI transgenic sugarcane lines expressing genes UQ14S and UQ68J, but only from stem tissue of transgenic lines expressing UQErw Transgenic lines of sugarcane cultivar Q117 were selected that expressed SI genes UQErw (11 lines), UQ14S (11 lines) or UQ68J (9 lines) introduced downstream of the Ubi promoter. This promoter is known to drive sustained 'constitutive' expression in most sugarcane tissues, with higher expression levels induced by heat shock and some other environmental stresses (Hansom et al., 1999). In glasshouse-grown 6-month-old plants with 12 to 15 nodes, isomaltulose was detected from leaf, root and stem tissues in pUbi14S and pUbi68J lines, but only from stem tissue of pUbiErw lines (FIG. 1). The results confirm that the introduced SI genes are functional in sugarcane, and show that UQ68J confers the most efficient conversion efficiency from sucrose to isomaltulose in mature sugarcane plants (FIG. 2), as previously demonstrated in E. coli and in transgenic sugarcane callus (Birch and Wu, 2002).

Figure 3:
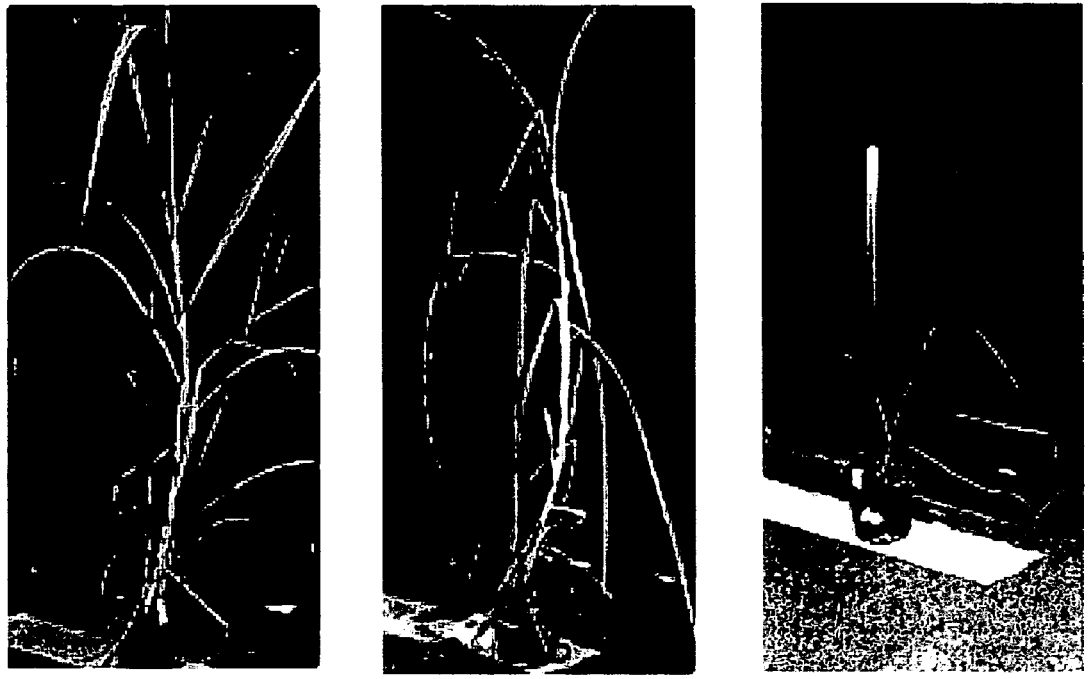
FIG. 3 is photographic representation of six-month-old representative plants of three phenotypic classes in sugarcane lines transformed using pUbi68J. Left: Normal (pUbi68J2.36). Middle: Weak Midrib (pUbi68J1.2). Right: Stunted (pUbi68J2.22). The plants were first vegetative generation from callus.

Constitutive overexpression of cytosol-targeted UQ68J SI retarded growth, changed morphology and inhibited sucrose accumulation of the transgenic sugarcanes All pUbiErw and pUbi14S transgenic sugarcane lines were phenotypically indistinguishable from control Q117 plants grown under the same conditions (Table 2). Nine pUbi68J transgenic sugarcane lines could be classified (FIG. 3) as:

1) 'Normal'. Five lines (like pUbi68J2.36) were phenotypically indistinguishable from control Q117.

2) 'Weak Midrib'. One line (pUbi68J1.2) had similar growth and size to Q117 except that midribs creased in fully expanded leaves.

3) 'Stunted'. Three lines showed retarded growth with short, thin internodes and small leaves. Of these, only line pUbi68J2.22 survived.

TABLE 2

Phenotypic features of Q117 control and representative transgenic sugarcane lines grown for 6 months in glasshouse conditions.

| Plant Line | Stem diameter (mm) | Height (cm) | Total nodes | Appearance |
|---|---|---|---|---|
| Q117 (Control) | 18 | 184 | 15 | Normal |
| pUbi14S2.36 | 20 | 185 | 15 | Normal |
| pUbiErw3.7 | 17 | 180 | 15 | Normal |
| pUbi68J2.36 | 17 | 172 | 15 | Normal |
| pUbi68J1.2 | 15 | 155 | 16 | Weak midribs |
| pUbi68J2.22 | 7 | 20 | 12 | Stunted |

Figure 4:
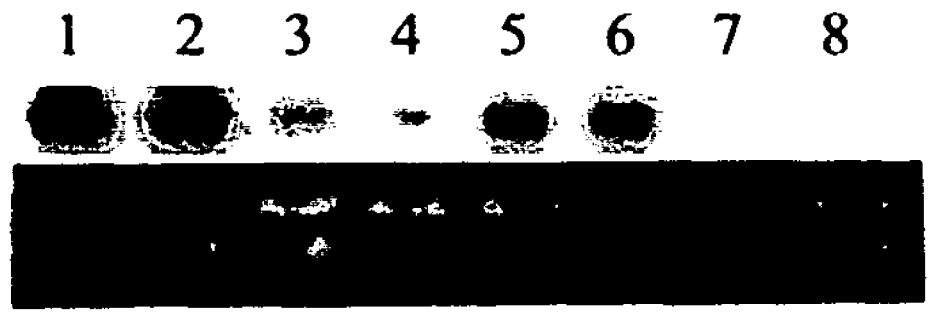
FIG. 4 is a photographic representation showing northern blot analysis of total RNA from sugarcane leaves and stems. The sampled plants were 6 months old with 12 to 15 nodes, in their first vegetative generation from callus. Top shows the hybridized band probed with UQ68J sucrose isomerase cDNA, the molecular size is about 1700 bp. Bottom shows the total RNA loading by the ethidium bromide staining of large and small rRNA subunits. Lane 1. pUbi68J2.22 internodes 3-4. Lane 2. pUbi68J2.22 leaf number 1-2. Lane 3. pUbi68J2.36 internodes 3-4. Lane 4. pUbi68J2.36 leaf number 1-2. Lane 5. pUbi68J1.2 internodes 3-4. Lane 6. pUbi68J1.2 leaf number 1-2. Lane 7. Q117 control internodes 3-4. Lane 8. Q117 control leaf number 1-2.
Figure 5:
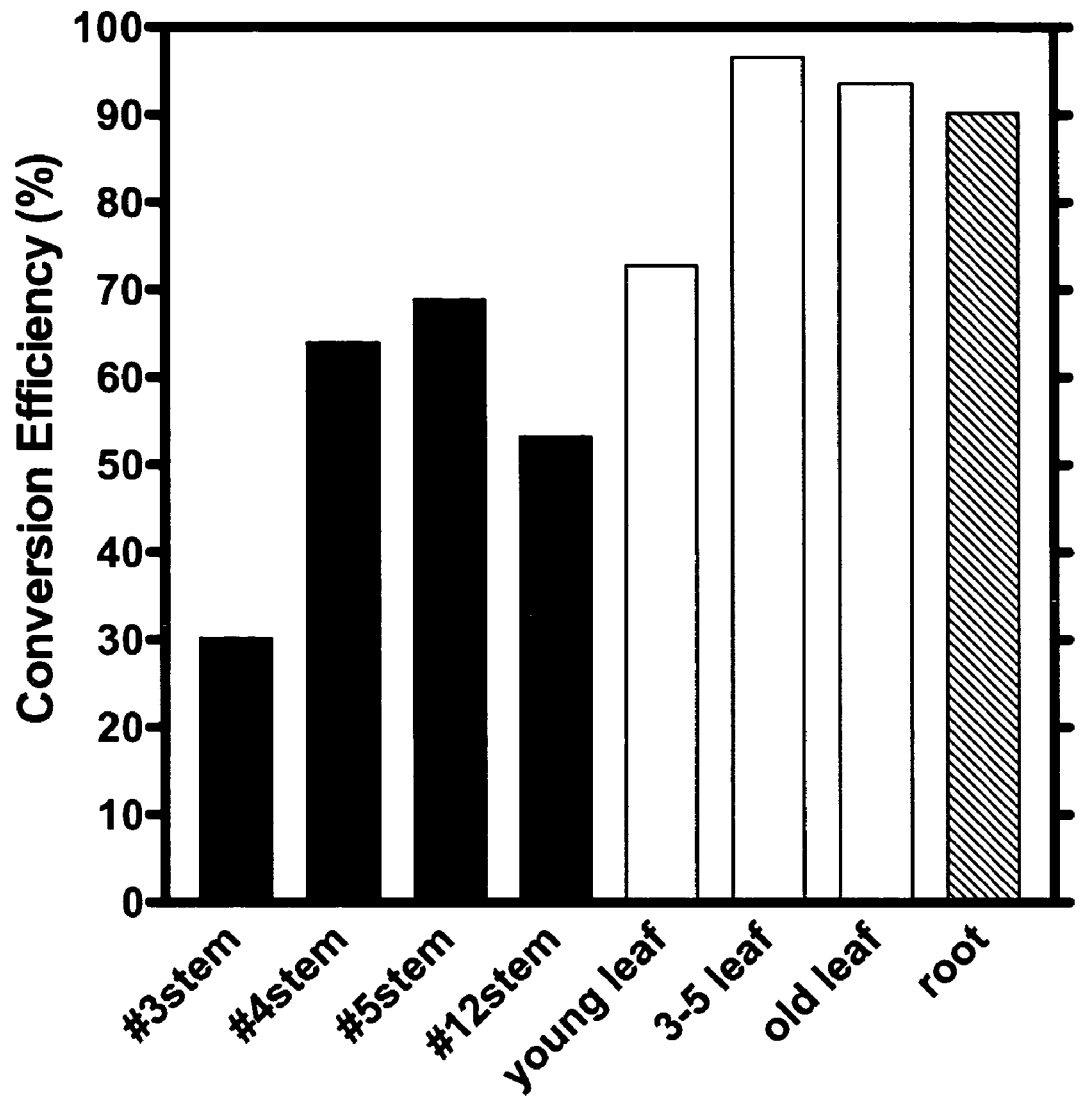
FIG. 5 is a graphical representation showing high efficiency of conversion from sucrose into isomaltulose in the stem, leaves and roots of transgenic line pUbi68J2.22. The sampled plants were 6 months old with 12 nodes, in their first vegetative generation from callus.

Northern analysis of representative lines pUbi68J2.36 (normal), pUbi68J1.2 (weak midrib) and pUbi68J2.22 (stunted) showed the highest level of UQ68J transcripts in the stunted plants, whereas the other two categories had a lower level of SI gene expression (FIG. 4). The high level of UQ68J transcripts corresponded with a high conversion efficiency of sucrose to isomaltulose (up to 96%, 90% and 69% in the leaf, root and stem, FIG. 5), and seriously depleted sucrose concentrations in stems (Table 3).

TABLE 3

Efficiency of conversion of endogenous sucrose to isomaltulose, and sugar concentrations in Q117 control and transgenic plants grown for 6 months in glasshouse conditions.[1]

| Transgenic line | Stem conversion efficiency (%) | [Sucrose] (mM) | [IM] (mM) | [Total sugar] (mM sucrose equivalent) |
|---|---|---|---|---|
| pUbi68J2.36 | 2.5 | 479.6 | 12.2 | 716.3 |
| pUbi68J1.2 | 20.6 | 68.4 | 16.7 | 135.7 |
| pUbi68J2.22 | 56.9 | 13.3 | 17.5 | 18.9 |
| Q117 (control) | 0.0 | 362.0 | 0.0 | 368.8 |

[1]Sugars were quantified by CE analysis after passage through ion exchange filters (SCX and SAX), with correction for known dilution and differential losses of sugars in the procedure to present results equivalent to concentrations in juice. Conversion efficiency is defined as isomaltulose/(sucrose + isomaltulose).

Figure 6:
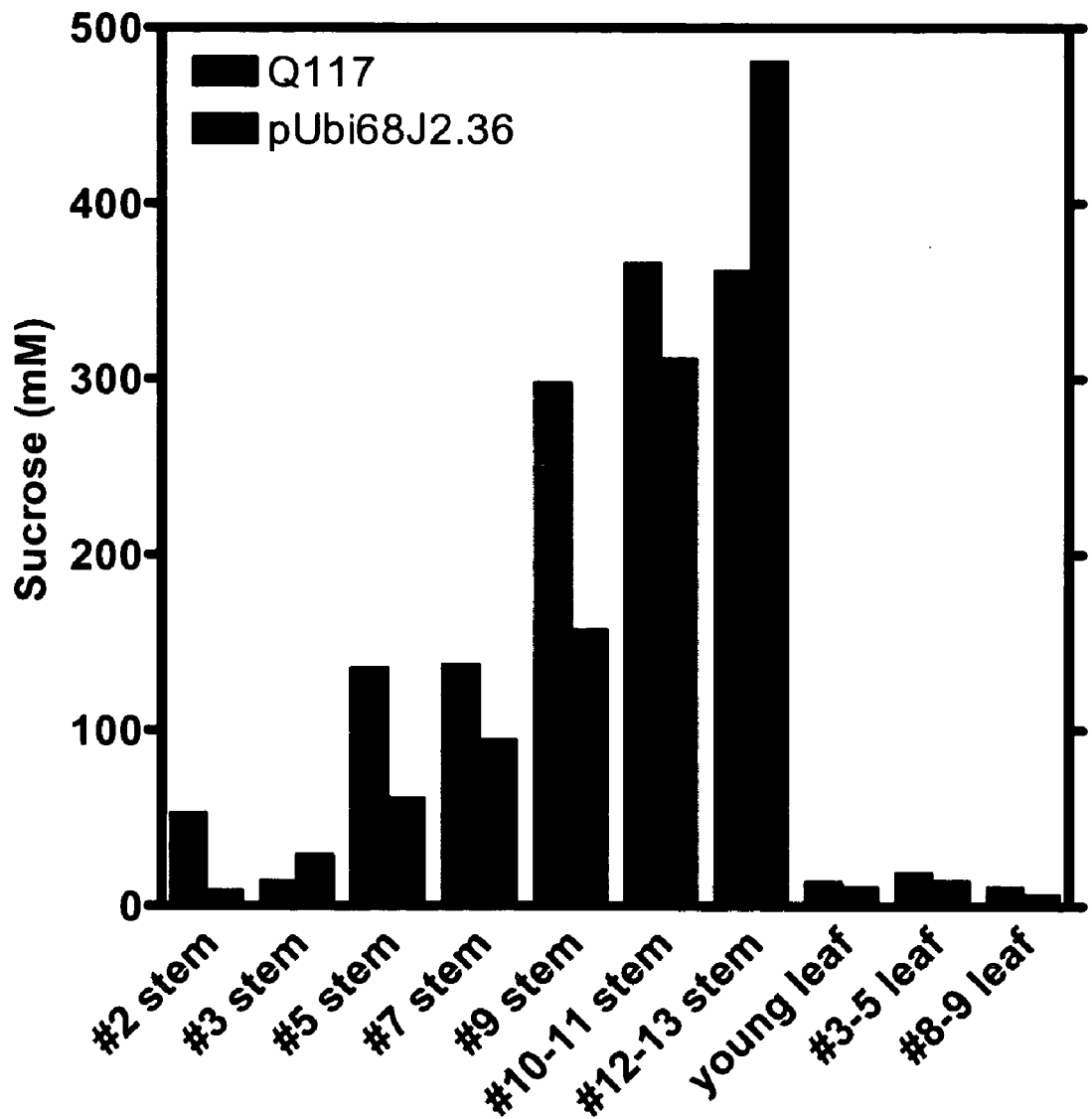
FIG. 6 is a graphical representation showing sucrose accumulation in transgenic pUbi68J2.36 and Q117 control sugarcane plants. The sampled plants were 6 months old with 15 nodes, in their first vegetative generation from callus.
Figure 7:
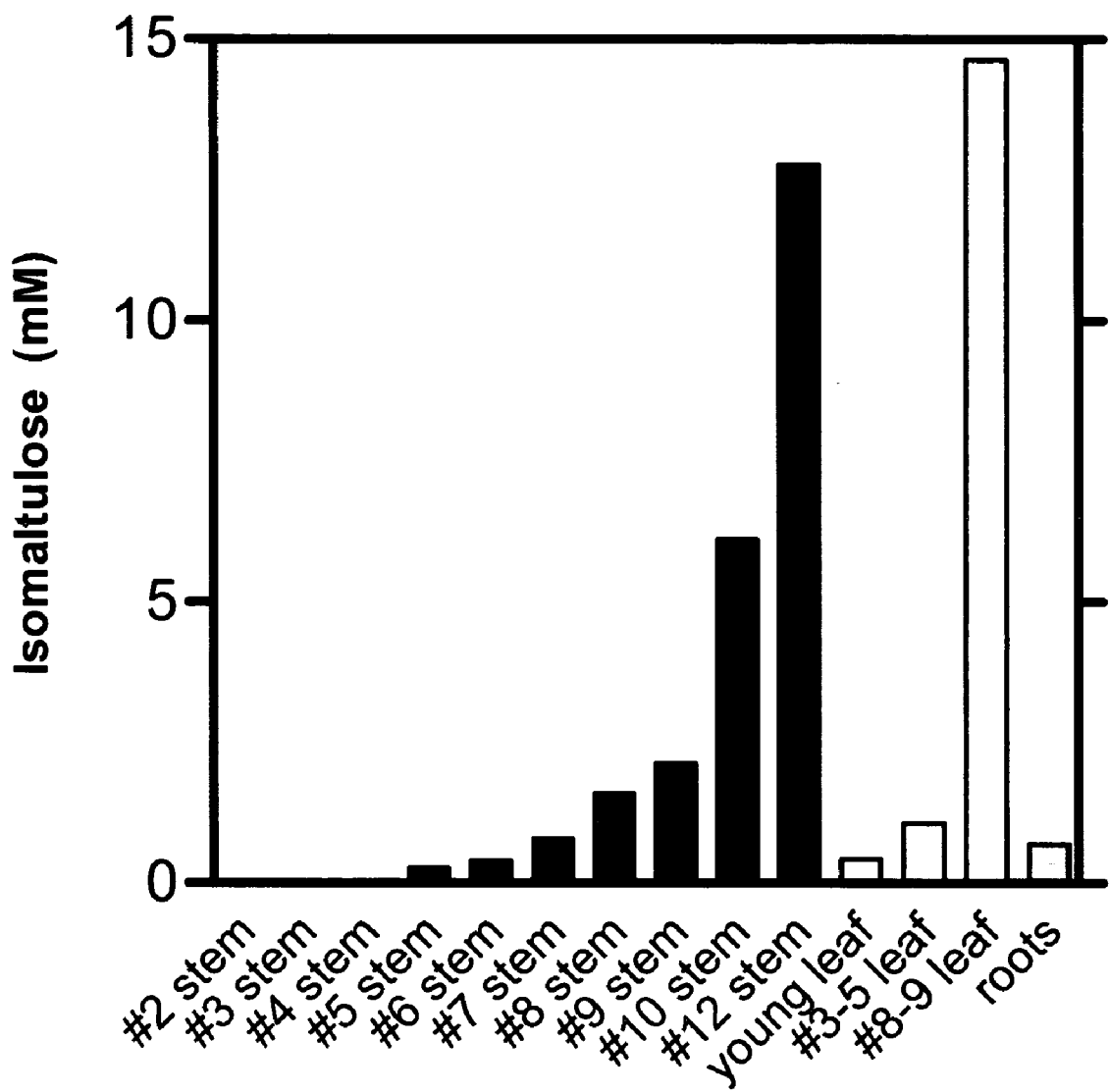
FIG. 7 is a graphical representation showing isomaltulose accumulation in stem and leaf tissues of transgenic line pUbi68J2.36 The sampled plants were 6 months old with 15 nodes, in their first vegetative generation from callus.

Sucrose Accumulation Pattern was not Adversely Affected by Isomaltulose Production in the Transgenic Lines with Low Expression of Cytosol-Targeted SI Genes Sugar profiles along developmental stages of the transgenic line with a low level of UQ68J transcripts showed a sucrose accumulation pattern similar to the Q117 control (FIG. 6). Isomaltulose concentration also increased with stem maturity (FIG. 7). These results indicate that conversion of sucrose to isomaltulose under a certain threshold, even within the cytoplasm, did not interfere with sucrose transport and accumulation. In addition, isomaltulose proved stable and able to be accumulated in sugarcane.

These results indicate that:

(i) The UQ68J gene has advantages over other tested SI genes for expression in plants directed towards the efficient conversion of sucrose into isomaltulose. This is highly desirable for industrial applications such as use of plants as biofactories for the manufacture of isomaltulose.

(ii) Because isomaltulose is not metabolized by plants, it can be a stored sugar isolated from the 'futile cycle' of sucrose cleavage and synthesis that may limit ultimate sugar yields in plants, and from the remobilization of stored sucrose under certain environmental conditions that may diminish harvestable sugar yield. Therefore an appropriate pattern of SI activity has the potential to enable increased yields of total sugars in plants by diverting part of the sugar pool into a non-metabolized sink. This effectively makes sugar accumulation a 'one-way valve' into an isomaltulose pool for subsequent harvest. Furthermore, it is possible that accumulation of the isomaltulose pool may be achieved without commensurable depletion of the remaining pool of soluble sugars. Practical achievement of these linked potentials is highly desirable for industrial applications such as use of plants as biofactories for the accumulation of the highest possible yield of stored soluble sugars.

(iii) The high-level constitutive expression of a gene for an efficient cytosol-targeted SI severely inhibits plant growth, by sequestering sucrose required for growth into isomaltulose which is unavailable for plant metabolism. This is highly undesirable for industrial applications, because growth of the plants is required to provide the reservoir for storage of substantial quantities of the desired products: isomaltulose and other soluble sugars. Below, the present inventors provide a solution to this key limitation, by demonstrating that for optimal industrial production of isomaltulose, expression of the introduced SI gene is advantageously regulated to restrict the SI activity substantially within the sub-cellular compartment used for sugar storage such as the vacuolar compartment of sugarcane storage parenchyma cells in the mature sugarcane stem.

Figure 8:
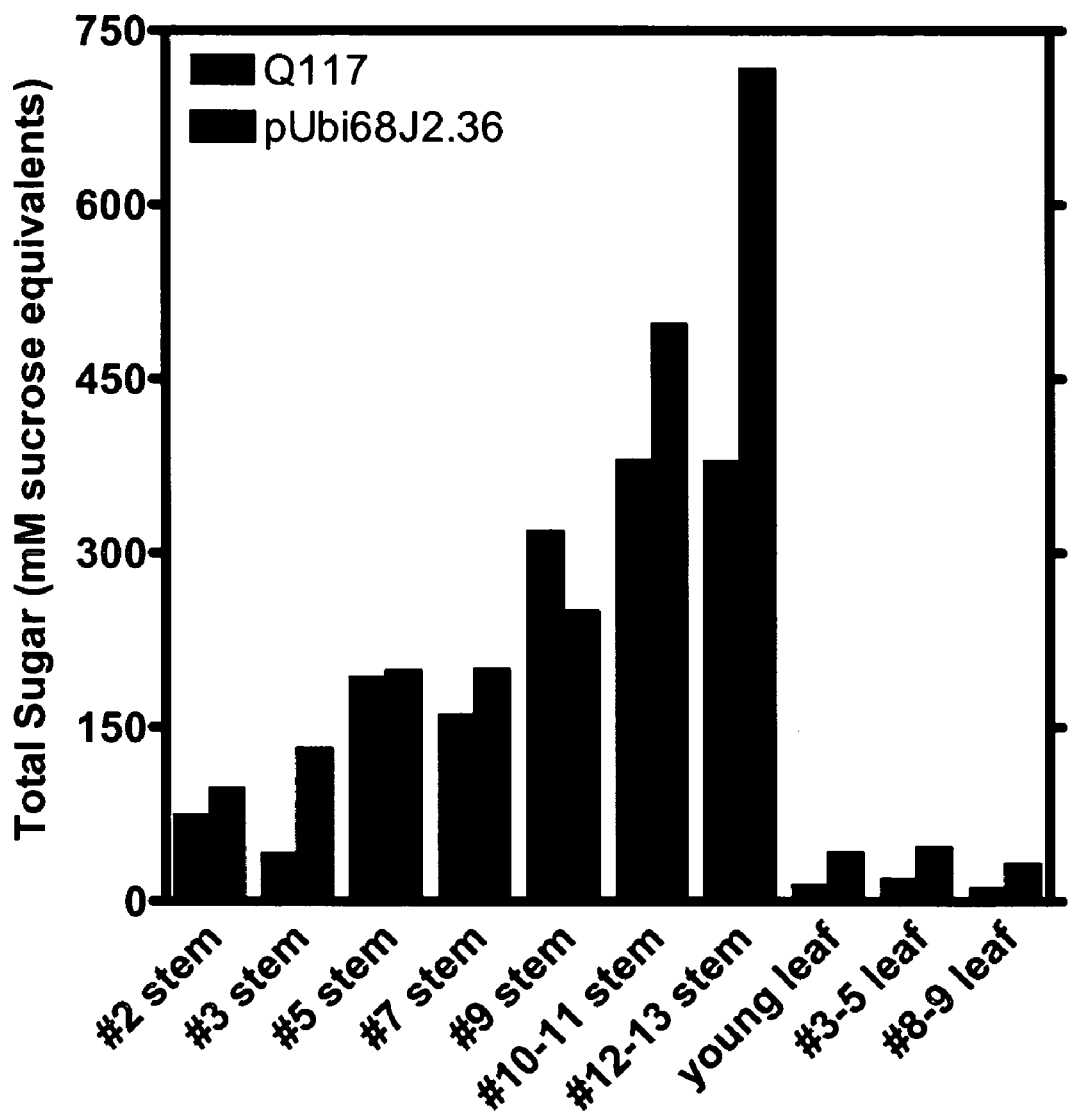
FIG. 8 is a graphical representation showing total soluble sugar concentration (glucose equivalents) in transgenic pUbi68J2.36 and Q117 control sugarcane plants. The sampled plants were 6 months old with 15 nodes, in their first vegetative generation from callus.

Total Soluble Sugar Content Increased in Stems of Some Transgenic Lines with Low Expression of Cytosol-Targeted SI Genes In transgenic line pUbi68J2.36, total soluble sugar concentration (expressed as glucose equivalents) increased 1.9-fold in the mature stems (internodes #12 to 13) and 2.4- to 3.0-fold in the leaves of 6-month-old plants, relative to the Q117 controls (FIG. 8). In another transgenic line pUbi68J2.28, total glucose equivalent sugar concentration increased 1.6-fold in the mature stems (internode #18) of 9-month-old plants, relative to Q117 controls. In a single stalk analysis of lines pUbi14S2.27, pUbiErw2.1 and pUbiErw3.7 at 9 months of age, glucose equivalent sugar concentrations in internodes #20 were 1.5- to 1.6-fold higher than in Q117 controls. Morphologically, all of these lines showed no difference from Q117 control sugarcane plants. Isomaltulose concentrations in these lines were typically low relative to sucrose concentrations, ranging from less than 1% up to 5% of total sugars present as isomaltulose in mature stems.

The higher total soluble sugar content came mainly from increased sucrose, glucose and fructose rather than from isomaltulose. For example, in transgenic line pUbi68J2.36 the percentage contributions to glucose equivalents in mature stem were sucrose (80%), isomaltulose (3%), fructose (6%) and glucose (11%). In contrast, in Q117 controls, the percentage contributions were sucrose (98%), fructose (1%), and glucose (1%). It should be noted that even though sucrose only accounted for 80% in line pUbi68J2.36 versus 98% in Q117, absolute sucrose concentration in the transgenic line was 1.3-fold that of the Q117 control (Table 2). The commercial potential, especially for industrial utilization as a fermentation feedstock such as for ethanol production from these lines is tremendous.

Figure 9:
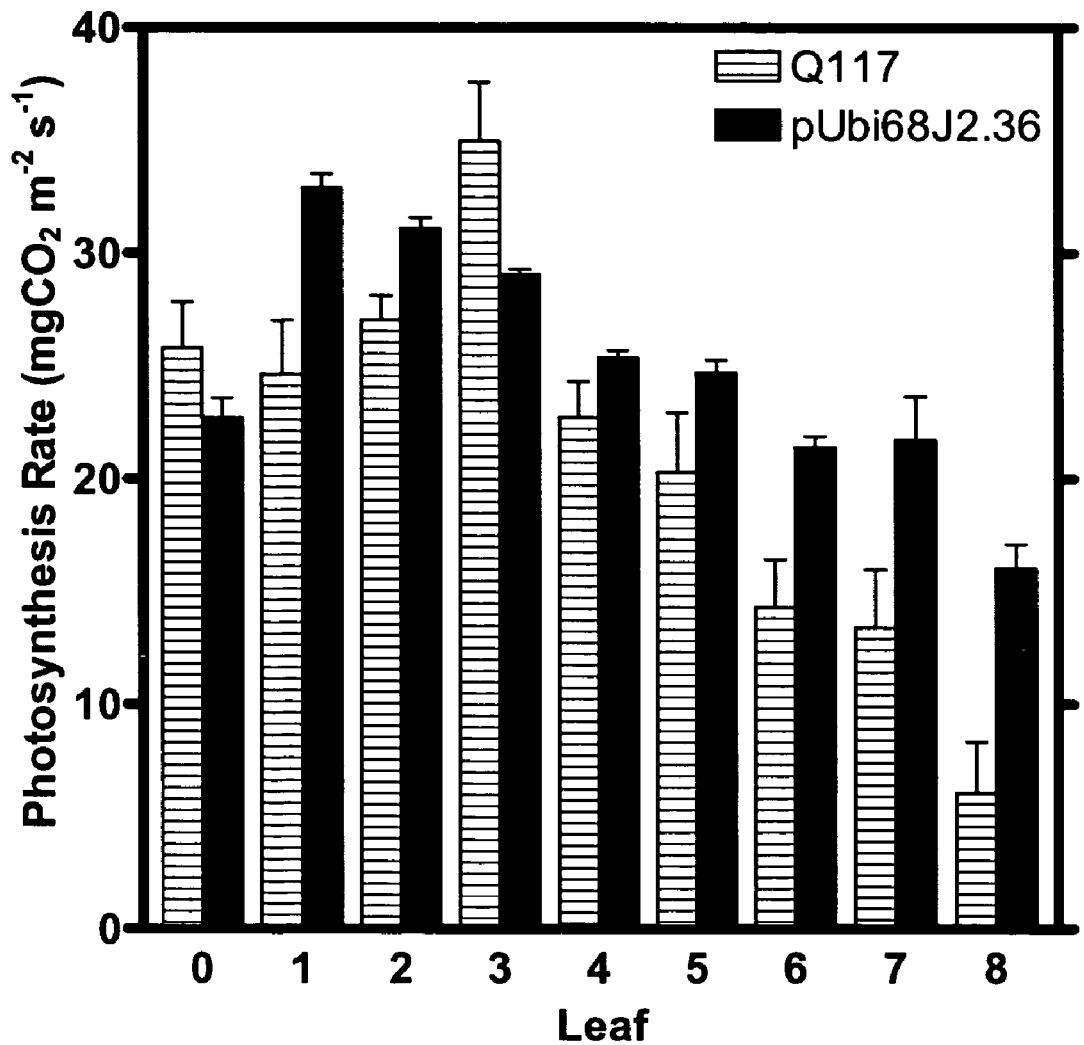
FIG. 9 is a graphical representation showing photosynthetic $CO_2$ fixation rates in leaves of transgenic line pUbi68J2.36 and Q117 control sugarcane plants. The plants were 4 months old and were morphologically indistinguishable. The plants of transgenic pUbi68J2.I36 line were the third vegetative generation (from stem cuttings) after regeneration. Results are means with standard errors from 3 replicate plants.

Characters Related to Photosynthesis Improved in Parallel to the Increase of Fermentable Sugar Concentration in the Transgenic Lines with Low Expression of Cytosol-Targeted SI Genes To further elucidate the mechanism of the improvement in total sugar concentration in the transgenic lines with low SI expression, photosynthesis rates and related indices were measured. Relative to Q117 controls, most leaves of pUbi68J2.36 showed higher $CO_2$ fixation rates, particularly in the older leaves (FIG. 9).

Figure 10:
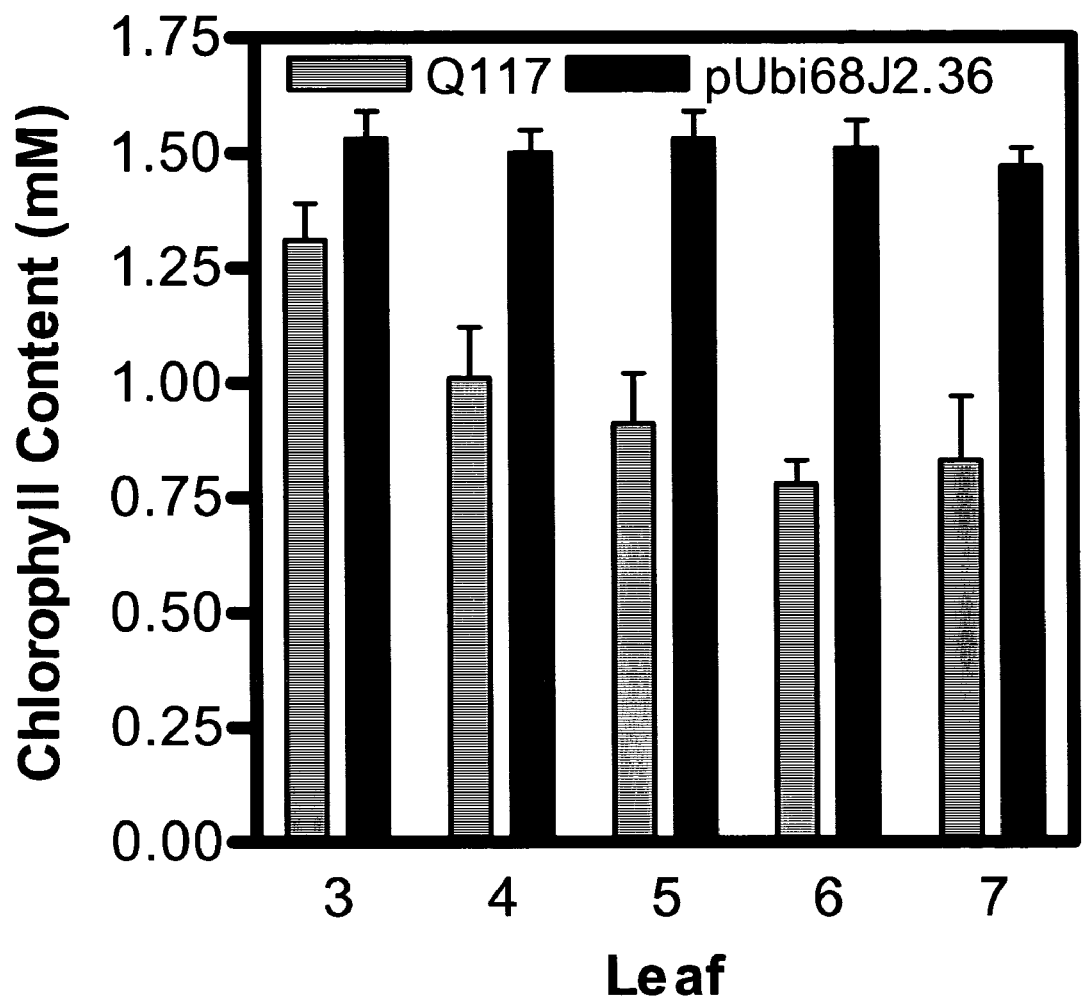
FIG. 10 is a graphical representation showing chlorophyll concentration in leaves of transgenic line pUbi68J2.36 and Q117 control sugarcane plants. The plants were 4 months old and were morphologically indistinguishable. The plants of transgenic pUbi68J2.I36 line were the third vegetative generation (from stem cuttings) after regeneration. Results are means with standard errors from 3 replicate plants.
Figure 11:
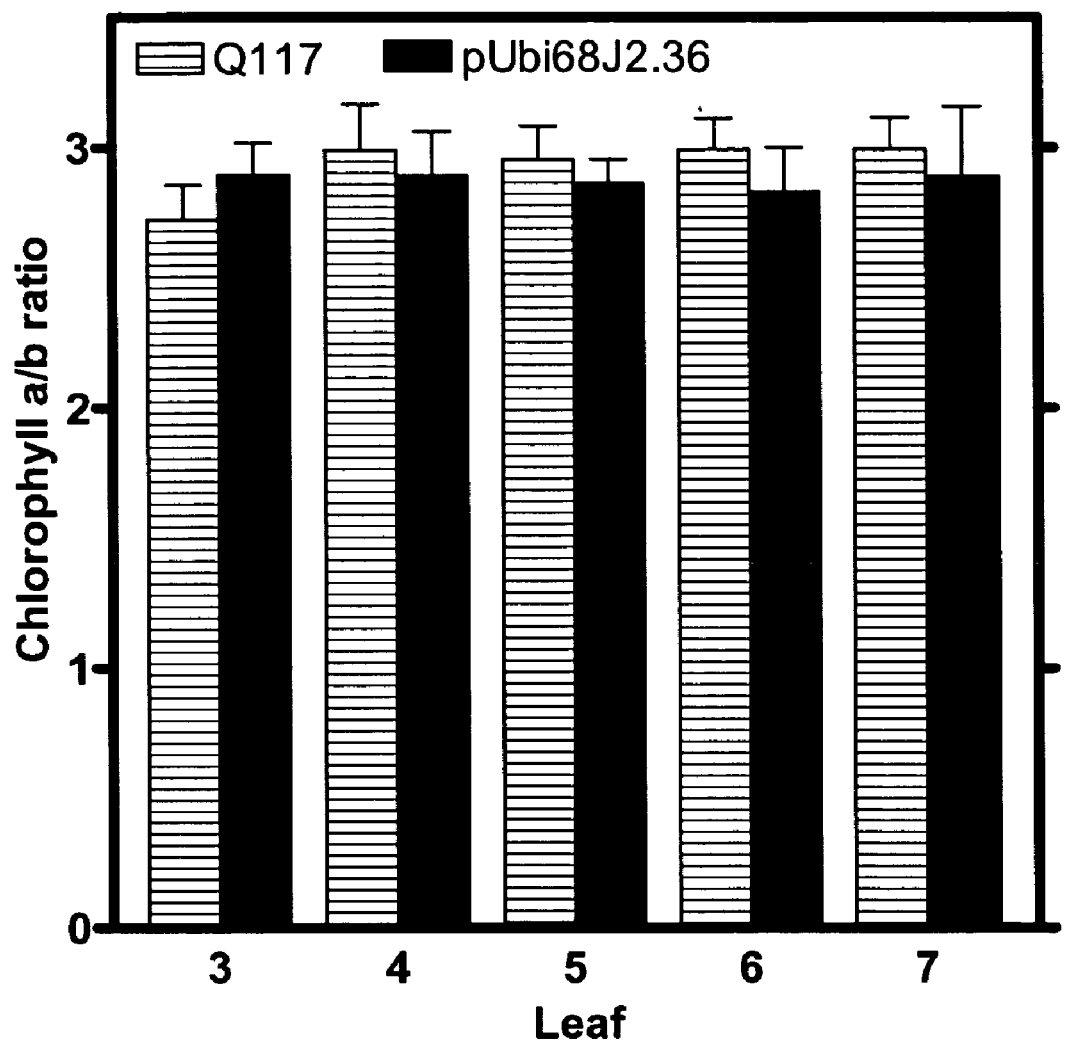
FIG. 11 is a graphical representation showing chlorophyll a/b ratios in leaves of transgenic line pUbi68J2.36 and Q117 control sugarcane plants. The plants were 4 months old and were morphologically indistinguishable. The plants of transgenic pUbi68J2.I36 line were the third vegetative generation (from stem cuttings) after regeneration. Results are means with standard errors from 3 replicate plants.
Figure 12:
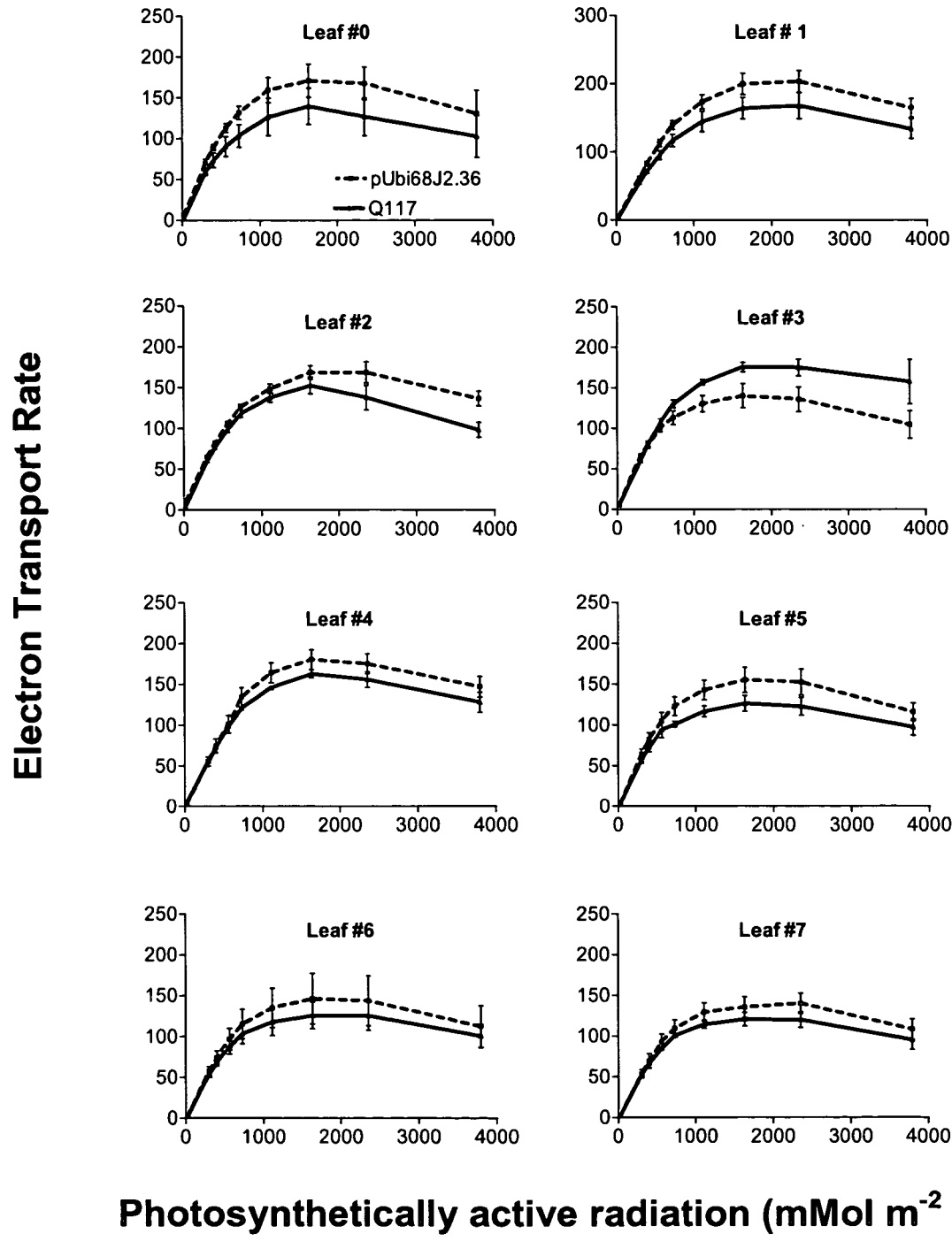
FIG. 12 is a graphical representation showing photosynthetic electron transport rates measured from chlorophyll fluorescence at various light intensities in leaves of transgenic line pUbi68J2.36 and Q117 control sugarcane plants. The plants were 4 months old and were morphologically indistinguishable. The plants of transgenic pUbi68J2.I36 line were the third vegetative generation (from stem cuttings) after regeneration. Results are means with standard errors from 3 replicate plants.

Chlorophyll content and electron transport rates were also higher in the transgenic line, and again the difference was greater in the older leaves (FIG. 10). Chlorophyll a/b ratio in Q117 control leaves was similar or higher than in the transgenic line in most leaves (FIG. 11). Electron transport rates of photosystem II measured by chlorophyll fluorescence partially reflected the difference in photosynthetic efficiency between the transgenic and control plants, with a higher light response curve for most leaves of the line pUbi68J2.36 as compared to the Q117 control (FIG. 12).

These results indicate that:

(i) Expression in plants of a gene for a sucrose isomerase, such that a part of the sucrose pool in the plant is converted to an isomer not recognized as equivalent to sucrose by the relevant plant control mechanisms, can result in the accumulation of higher total sugar levels in plant tissues;

(ii) Specific alterations to metabolism, involving the conversion of an endogenous sugar normally sensed by the organism into a novel sugar that is not perceived in an equivalent manner, can shift metabolism to accumulate a higher concentration of soluble carbohydrate through a combination of effects on synthesis in source tissues, transport between source and sink tissues, and turnover or storage within the sink tissues.

Vacuole-Targeted SI Expressed from Promoter Ubi

Healthy Plants with High Isomaltulose Yields were Produced by Targeting the SI Gene Products into Vacuoles Transgenic sugarcane lines were selected that targeted UQ68J Si gene product into vacuoles of sugarcane cultivar Q117 by means of a fusion to NTPP from sweet potato sporamin (22 lines with NTPP only; 9 lines with NTPP and His tag), to CTPP from tobacco chitinase (7 lines with CTPP only; 11 lines with CTPP and His tag) or to both NTPP and CTPP signal peptides without His tags (9 lines). In glasshouse-grown 8-month-old plants with about 20 nodes (plants grown from single-eye setts) to 30 nodes (from ratoon plants), isomaltulose could be detected from stem tissues in about 80% of the tested pU3ZERsN68J, pU3ZERc68JC, pU3ZERsN68]-His, pU3ZERc68JC-His and pU3ZERsN68JC lines (detailed in the following sections).

Figure 15:
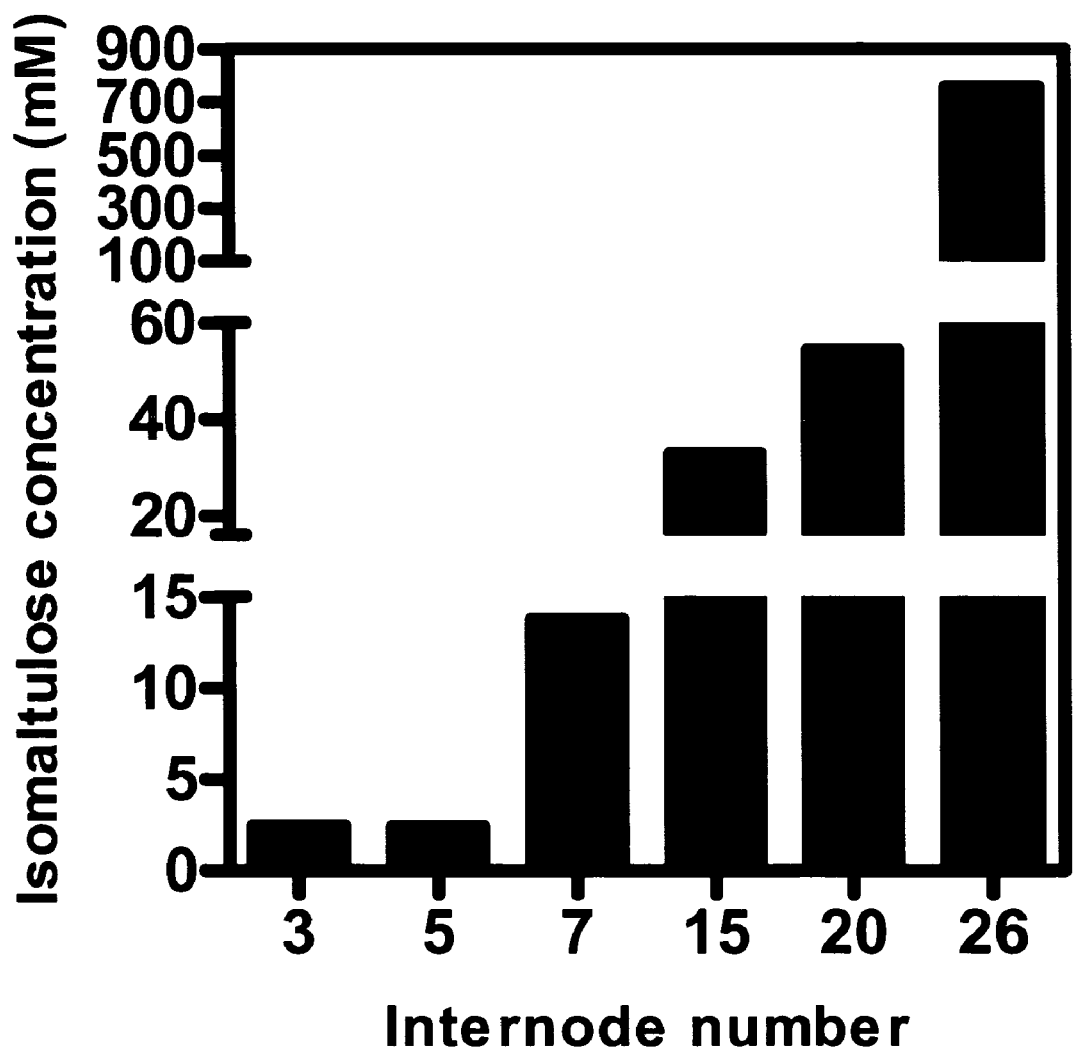
FIG. 15 is a graphical representation showing isomaltulose concentrations in stem tissues of transgenic line pU3ZERsN68J3.2His (with vacuole-targeted sucrose isomerase). The plants were 8 months old with 35 internodes and were morphologically indistinguishable from the Q117 control. The transgenic plant was the second vegetative generation (ratoon cane within the original pot) after callus regeneration.

The highest isomaltulose concentration was 756 mM in mature stem tissues of line pU3ZRsN68JHis3.2. The level of isomaltulose accumulation varied between transgenic lines, consistent with the well-known variability in expression between independent transgene insertion events (Matzke & Matzke, 1998; Peach & Velten, 1991), and potentially influenced by micro-environmental effects on the inducible Ubi promoter (Hansom et al., 1999). Isomaltulose concentration increased with stem maturity in general agreement with the native pattern of increased sugar accumulation by sugarcane, and the ratio of isomaltulose to other sugars varied between transgenic lines (FIG. 15).

Figure 13:
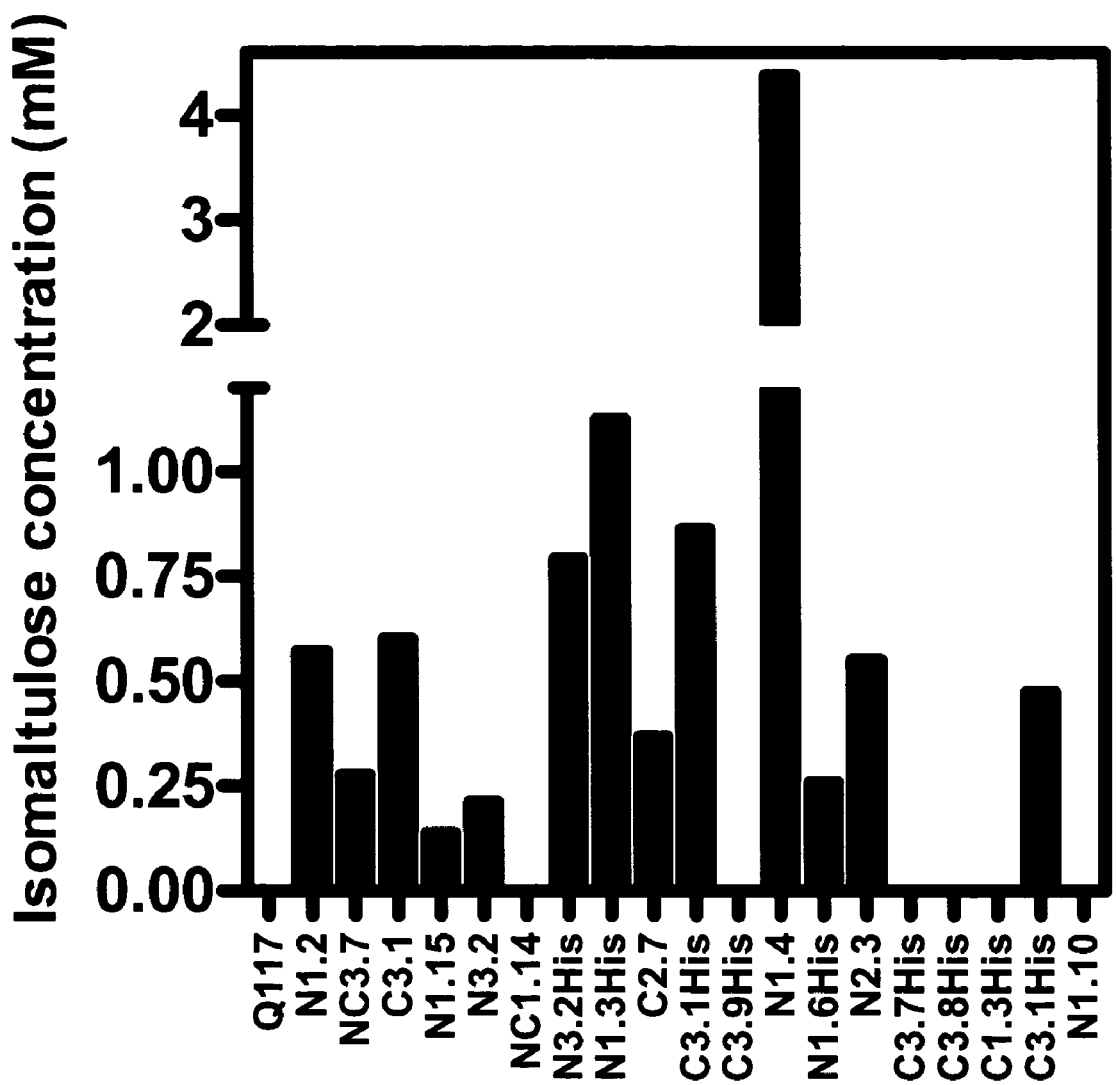
FIG. 13 is a graphical representation showing isomaltulose concentrations in roots of different transgenic lines with vacuole-targeted sucrose isomerase, and the Q117 control. Roots were harvested from two-eye sets of sugarcane that had been wrapped with damp tissue and placed at 28° C. for 7 days.
Figure 14:
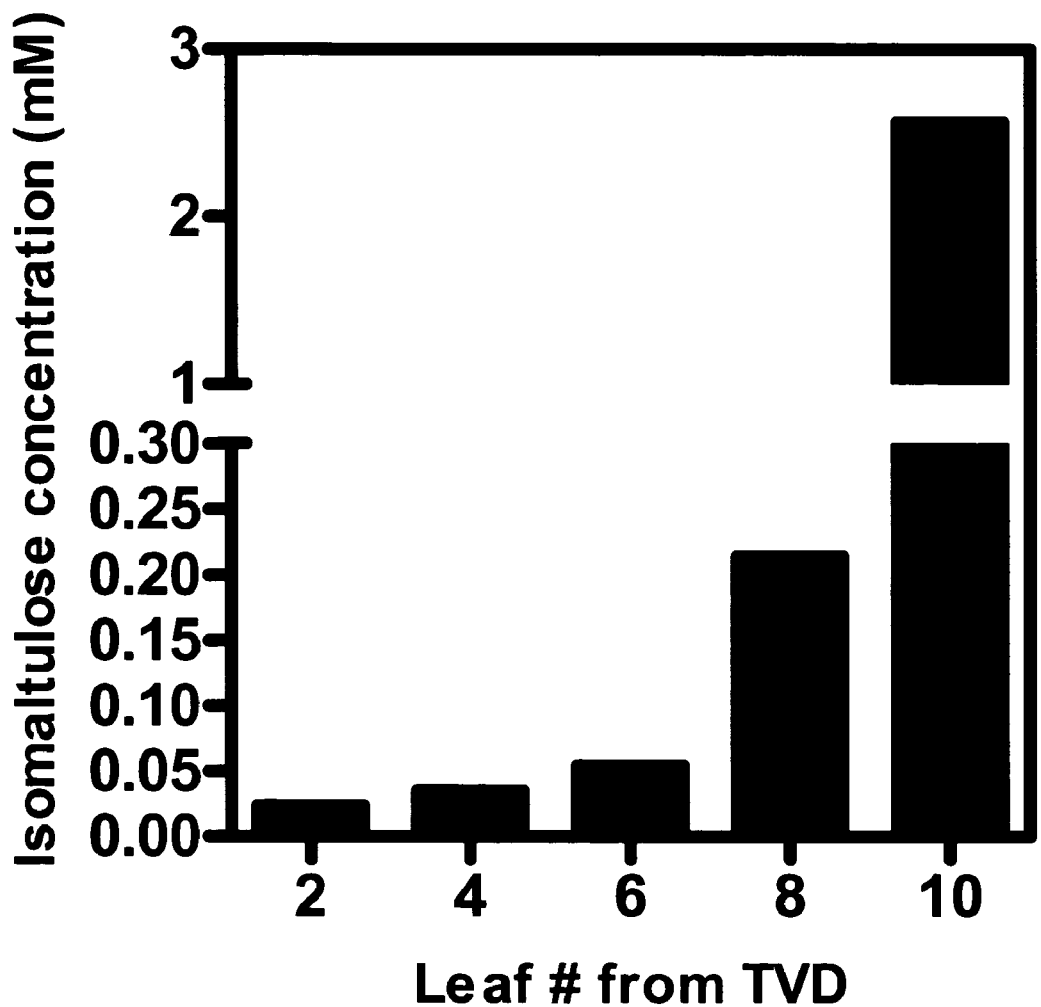
FIG. 14 is a graphical representation showing isomaltulose concentrations in leaves of transgenic line pU3ZERsN68J3.2 (with vacuole-targeted sucrose isomerase). The plants were 8 months old with 21 internodes and were morphologically indistinguishable from the Q117 control. The transgenic plant was the second vegetative generation (from stem cuttings) after regeneration.

Thirteen out of 20 tested transgenic lines (65%) were isomaltulose-positive in roots, but the isomaltulose concentrations were below 1 mM except in lines pU3ZERsN68J1.4 and pU3ZERsN68JHis1.3 (FIG. 13). Isomaltulose was detectable in leaf tissues only in the transgenic lines that accumulated a high level of isomaltulose in mature stem tissues. In these lines, isomaltulose accumulated gradually with leaf age, remaining below 1 mM up to leaf eight (FIG. 14). Other tested lines (for example, lines with high sucrose content, described below), were isomaltulose-negative in leaf tissues.

All generated transgenic lines appeared healthy and had no apparent morphologic difference from the Q117 control (Table 4).

TABLE 4

Phenotypic features of Q117 control and representative transgenic sugarcane lines with vacuole-targeted SI, grown for 8 months in glasshouse conditions.

| Plant Line | Stem diameter (mm) | Height (cm) | Total nodes | Appearance |
|---|---|---|---|---|
| Q117 (Control)[a] | 18 | 160 | 21 | Normal |
| Q117 (Control)[a] | 18 | 164 | 21 | Normal |
| Q117 (Control)[b] | 20 | 205 | 28 | Normal |
| pU3ZERsN68J3.2[a] | 19 | 185 | 22 | Normal |
| pU3ZERsN68J3.2His[a] | 17 | 165 | 22 | Normal |
| pU3ZERsN68J1.17[a] | 18 | 150 | 20 | Normal |
| pU3ZERsN68J1.2[b] | 17 | 205 | 31 | Normal |
| pU3ZERsN68J1.10[a] | 19 | 186 | 27 | Normal |
| pU3ZERc68JC1.3His[b] | 21 | 176 | 31 | Normal |
| pU3ZERc68JC3.7His[b] | 17 | 248 | 38 | Normal |
| pU3ZERc68JC3.8His[b] | 17 | 186 | 30 | Normal |
| pU3ZERsN68JC1.4[b] | 17 | 200 | 30 | Normal |
| pU3ZERsN68JC3.7[a] | 20 | 160 | 30 | Normal |

[a]Shoot generated from single-eye sett;
[b]Ratoon shoot.

These results indicate that:

(i) Even with 'constitutive' expression from promoter Ubi, targeting the SI transgene product to the vacuole allows substantial isomaltulose accumulation in sugarcane stem storage tissues without apparent adverse effects on plant growth and development.

(ii) The sugarcane vacuole is known to be hostile to most introduced proteins (Gnanasambandam & Birch, 2004), so SI is unlikely to accumulate in the compartment. However, with continuous supply of a highly efficient SI such as UQ68J into the sucrose storage vacuoles there can be a gradual developmental accumulation of isomaltulose to a high final yield.

(iii) Efficient targeting to the vacuolar pathway avoids SI activity in the metabolically active cytosolic compartment that predominates in the cells of actively growing tissues, thereby avoiding adverse effects on growth. This is highly desirable for industrial applications involving the conversion of sucrose into compounds that can not efficiently be metabolized by the plant.

Figure 16:
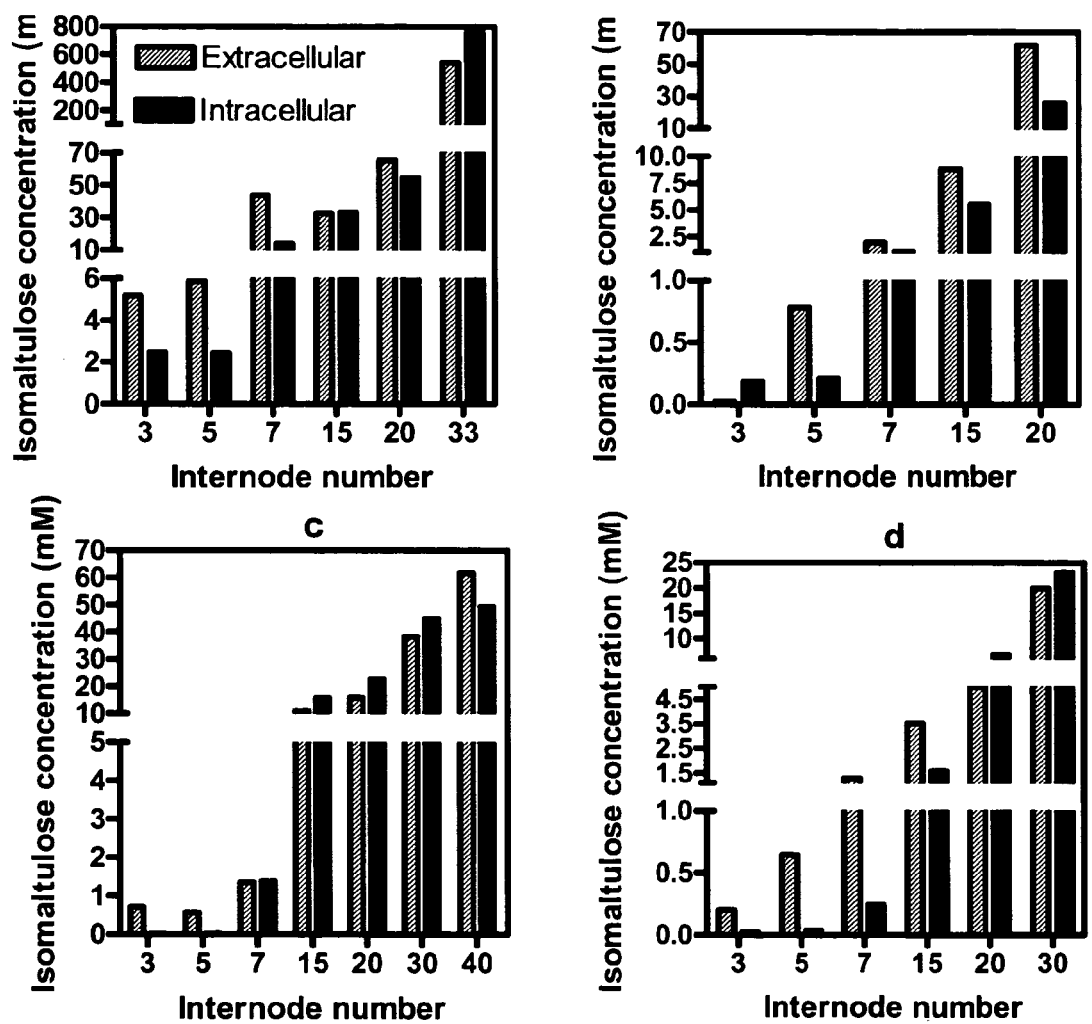

Isomaltulose was Detected in Both Intracellular and Extracellular Spaces in the Vacuole Targeted Transgenic Lines Isomaltulose was detectable in both the extracellular fluid fraction and the intracellular fluid fraction, at approximately the same concentrations. This phenomenon was common in all vacuole targeting constructs of NTPP, CTPP or both (FIG. 16). Sucrose concentrations are also similar in these fractions, but most sugar is present in the intracellular (vacuole) compartment because of the much greater volume of this compartment. It is known that a small proportion of vacuole-targeted protein can continue through the secretory pathway to the extracellular space where it may be more stable than in the vacuole (Gnanasambandam & Birch, 2004). Plants are believed to be unable to transport isomaltulose between compartments, so secreted SI is likely to be responsible for the observed accumulation of extracellular isomaltulose.

Provided there is no adverse effect on the plants, as in the lines observed in the present study, this effect is advantageous for industrial applications where the highest total conversion of sucrose is desired for maximum yield of the conversion products.

Total Sugar Content was Increased in Different Ways

Based on the different constructs and profiles of accumulated isomaltulose and sucrose in sugarcane stem, those transgenic sugarcane lines with high total sugar concentration relative to the control Q117 could be classified into four groups:

1. With NTPP-SI, in lines with high isomaltulose concentration (>70 mM), isomaltulose contributed substantially to total sugar content higher than that of the control Q117.

2. With NTPP-SI, in lines with moderate isomaltulose concentration (20-70 mM), higher total sugar content was mainly from higher sucrose concentration than that of the control Q117.

3. With NTPP-SI, in lines with isomaltulose below the detection threshold, sucrose concentration increased in mature stem to levels higher than that of the control Q117.

4. With SI-CTPP plus 6×His, in lines with low isomaltulose concentration (<10 mM), higher total sugar content was mainly from higher sucrose concentration than that of the control Q117.

High Isomaltulose Concentration Contributed Substantially to the Increased Total Soluble Sugar Content in Mature Stems of Some Transgenic Lines with NTPP-SI In transgenic line pU3ZERsN68J3.2 (abbreviated as N3.2 in the following sections), an 8-month old plant grown from a single-eye sett accumulated 108 mM isomaltulose in intracellular spaces of zone 2 in the 26$^{th}$ internode, equivalent to 14% of the total sugar content. A ratoon stalk accumulated 286 mM isomaltulose in the 22$^{nd}$ internode, equivalent to 47% of the total sugar content. A ratoon stalk of line pU3ZERsN68J3.2His (abbreviated as N3.2His) with 35 nodes accumulated 756 mM isomaltulose, equivalent to 67% of the total sugar content in the 33rd internode.

Figure 17:
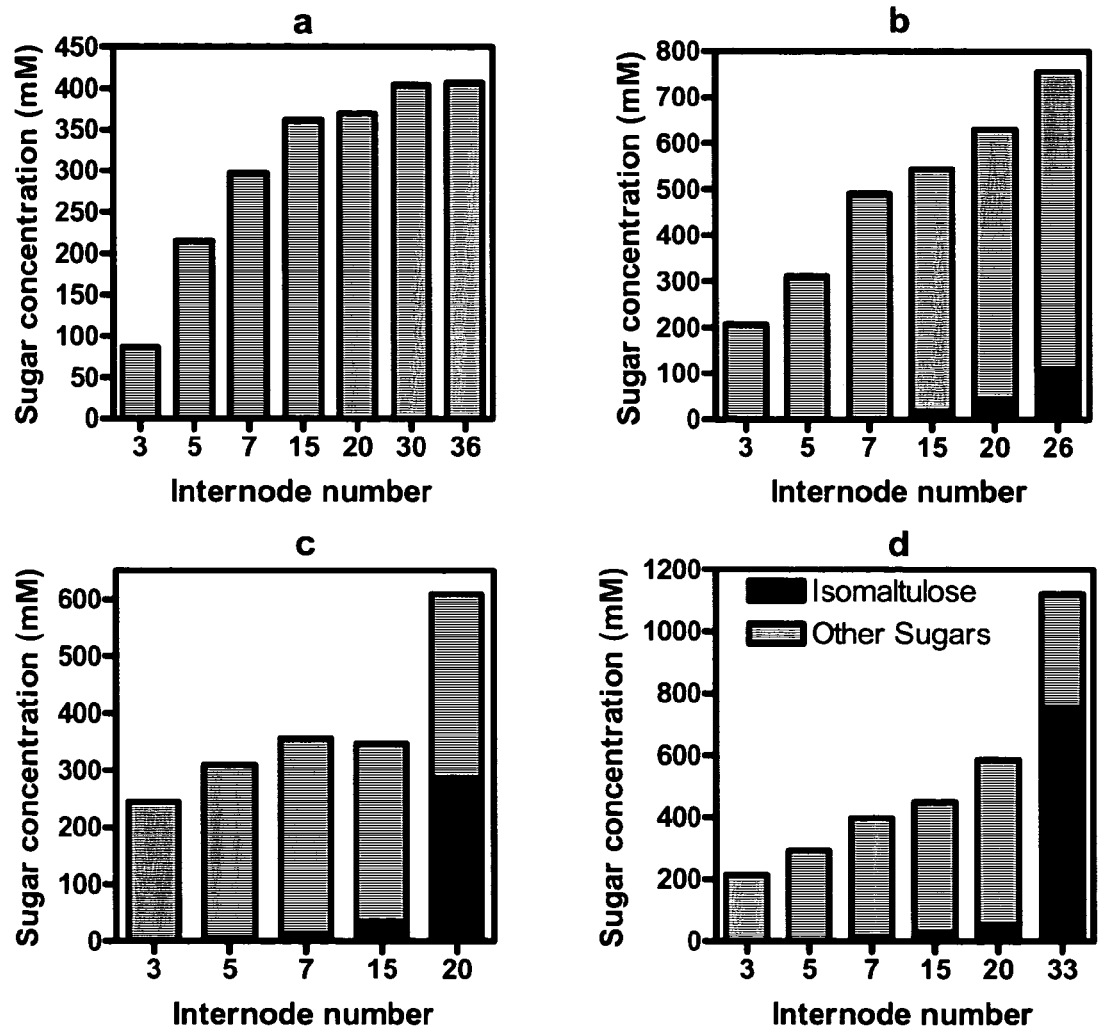

In the Q117 control, total sugar concentration ranged from 369 mM to 490 mM (sucrose equivalent) in the 20$^{th}$ internodes of different stalks. Compared to the highest total sugar content observed in the Q117 controls (490 mM), the total sugar concentrations in 20$^{th}$ internodes increased by 29% in N3.2, 24% in N3.2 ratoon, and 20% in N3.2His ratoon. By the 33$^{rd}$ internode, the total sugar concentration in the N3.2His ratoon was 2.7 times the level in the Q117 control (FIG. 17).

High isomaltulose concentrations were not observed in the transgenic lines with CTPP signal, or with dual NTPP+CTPP targeting signals. The NTPP signal may direct a higher efficiency of active SI gene product targeting into sugarcane sucrose storage compartments.

Figure 18:
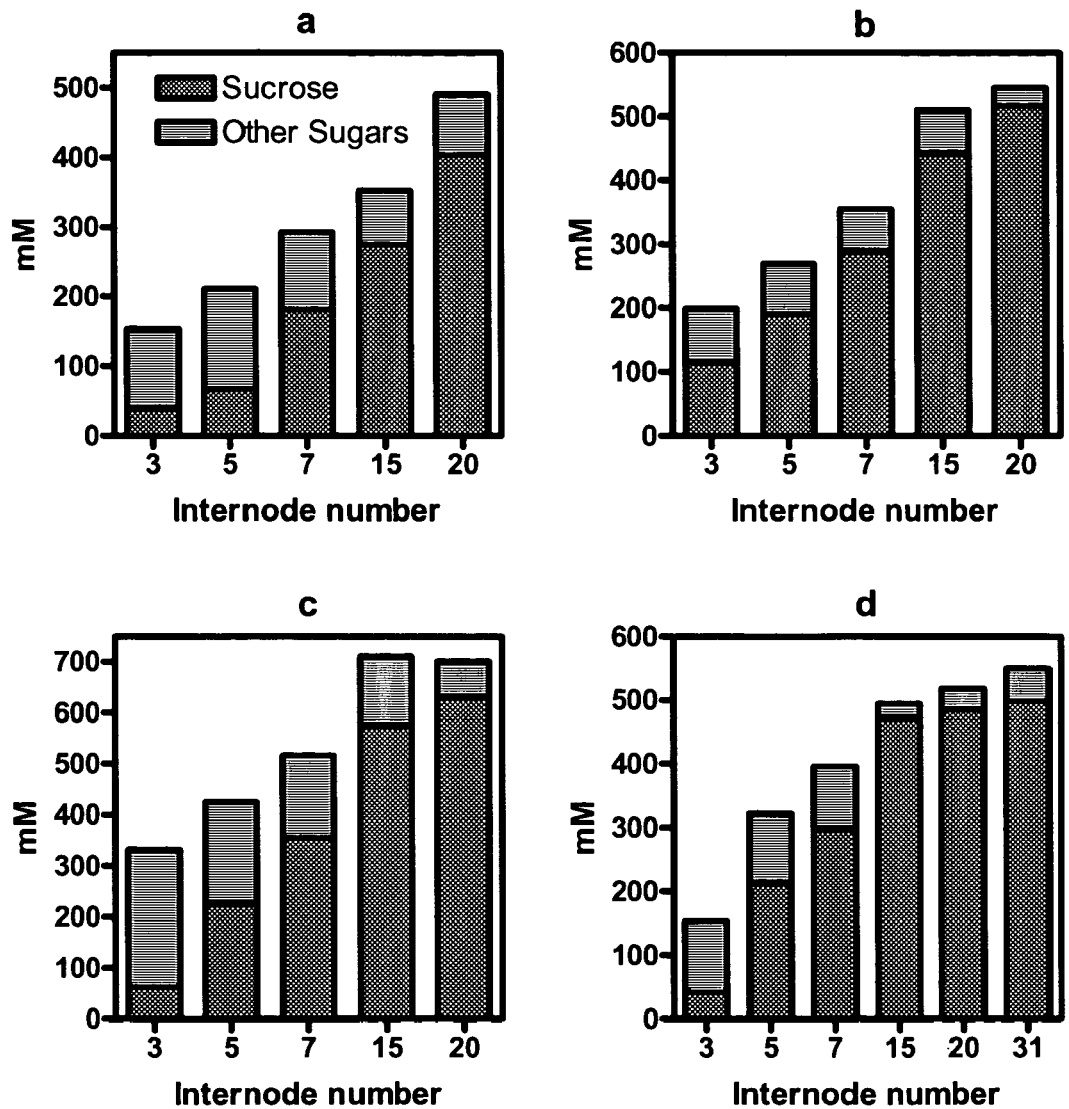

High Sucrose Concentration Contributed Substantially to the Increased Total Soluble Sugar Content in Mature Stems of the Transgenic Lines with NTPP-SI, with Moderate Isomaltulose Concentrations Transgenic lines such as pU3ZERsN68J1.17 (abbreviated as N11.17) and pU3ZERsN68J1.2 (abbreviated as N1.2) accumulated 1.1 to 1.6 times the sucrose content of the Q117 control. The sucrose concentration in the 20$^{th}$ internode of N1.17 was increased by 28% in plant cane and 56% in ratoon cane relative to the Q117 control. In N1.2 ratoon cane, sucrose content increased by 20% relative to the Q117 control. The proportions of sucrose to total sugar concentration in the mature internodes from the above three transgenic stalks were 95%, 90% and 91%, respectively. Isomaltulose concentrations in these lines were 25, 8 and 48 mM, which only accounted for 5%, 1% and 9% of the total soluble sugars (FIG. 18).

High Sucrose Concentration in Mature Stems of Transgenic Lines with NTPP-SI, with No Detectable Isomaltulose Transgenic lines such as pU3ZERsN68J1.10 (abbreviated as N1.10) had another pattern of sugar profiles. No isomaltulose was detected by HPLC-ED from stem, leaf or root tissues, though the SI gene was detected by PCR. Sucrose in the mature stem of N1.10 accumulated to 1.5 times the level in the Q117 control (Table 5).

TABLE 5

Comparison of sugar profiles in 20$^{th}$ internodes of transgenic line N1.10 and Q117 control ratoon canes.

| Transgenic line | Glucose (mM) | Fructose (mM) | Sucrose (mM) | Isomaltulose (mM) | Total sugar (mM, sucrose-equivalent) |
|---|---|---|---|---|---|
| Q117 | 5.7 | 4.4 | 448.9 | 0 | 453.9 |
| N1.10 | 6.1 | 6.1 | 662.6 | 0 | 668.7 |

[1]For this and subsequent tables, sugars were quantified by HPAE-PAD analysis, with correction for known dilution and losses of sugars in the procedure to present results equivalent to concentrations in juice.

Figure 19:
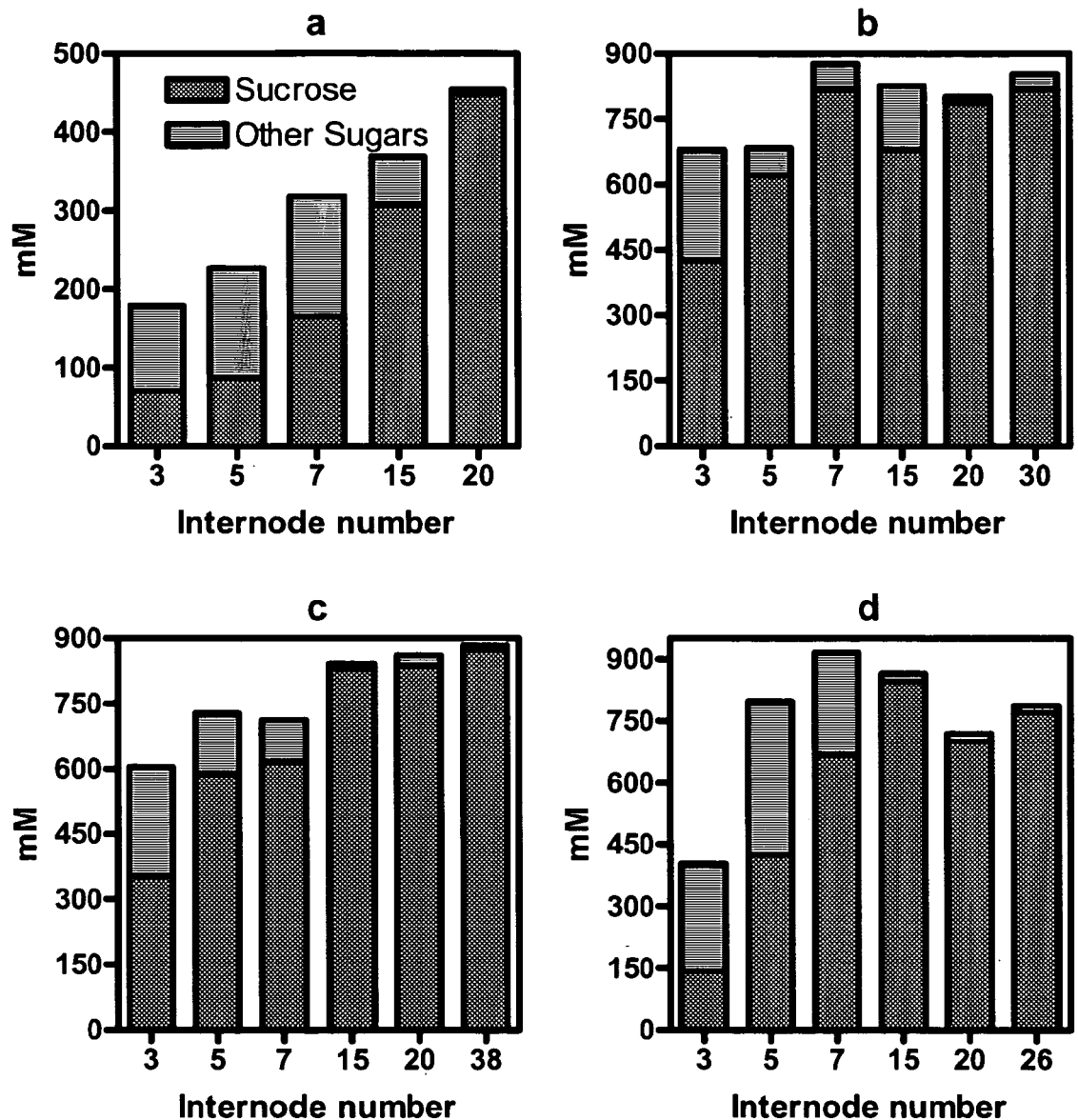

High Sucrose Concentration in Mature Stems of the Transgenic Lines with SI-CTPPHis, with Low Isomaltulose Concentration Three of 11 tested transgenic lines with SI-CTPPHis produced less than 2 mM isomaltulose in mature stems, and accumulated more total soluble sugars than the Q117 control. Transgenic lines pU3ZERc68JC1.3His (abbreviated as C1.3His), pU3ZERc68JC3.7His (abbreviated as C3.7His) and pU3ZERc68JC3.8His (abbreviated as C3.8His) accumulated sucrose to 1.8, 1.9, and 1.6 times the level in the Q117 control, as well as higher glucose and fructose contents (Table 6). For transgenic line C3.7His, isomaltulose was undetectable. In these lines, not only did the mature stems accumulate more total soluble sugars than the Q117 control, but the developmental profile of sugar accumulation was altered, with much sugar concentrations in the younger expanding internodes approaching the high concentrations observed in the mature internodes (FIG. 19).

In contrast, none of seven tested lines with SI-CTPP and no 6×His tag showed increased sucrose accumulation.

TABLE 6

High sugar contents in 20$^{th}$ internodes of ratoon lines with SI-CTPP plus 6 × His.

| Transgenic line | Glucose (mM) | Fructose (mM) | Sucrose (mM) | Isomaltulose (mM) | Total sugar (mM, sucrose-equivalent) |
|---|---|---|---|---|---|
| Q117 | 5.7 | 4.4 | 448.9 | 0 | 453.9 |
| C1.3 His | 12.8 | 13.2 | 786.9 | 1.1 | 801.0 |
| C3.7 His | 26.7 | 18.3 | 838.1 | 0 | 860.3 |
| C3.8 His | 14.5 | 19.4 | 701.7 | 0.2 | 718.9 |

Design and Selection of SI Constructs and Transgenic Lines for High Total Sugar Phenotypes Based on studies with reporter constructs, CTPP appears less efficient than NTPP for vacuolar targeting in sugarcane cells, leaving substantial detectable cytosolic activity (Gnanasambandam & Birch, 2004). Even with NTPP, a proportion of the linked protein may remain in the cytosol or be mis-targeted to other cellular compartments under particular developmental or physiological conditions (Gnanasambandam & Birch, 2004). These effects may be more prominent in some transformants than in others due to the influence of the different surrounding sequences and the different arrangement of inserted sequences in different transformation events. The 6×His tag is likely to influence transport, stability and/or activity of the SI protein in various compartments, though the details of such effects have not been elucidated at the protein level.

Through a combination of such effects, various SI expression constructs can result in a proportion of transformants with a pattern of SI activity conferring a high total sugars phenotype. The present inventors have shown that it is possible through design and selection of SI constructs to increase the proportion of transformants with different desired sugar compositions within the high sugars phenotype. For example, NTPP-SI constructs are preferred to select lines with a high isomaltulose content, and SI-CTPPHis constructs are promising for selection of lines with high sucrose content across the stem developmental profile.

It is routine to screen transformants for individuals in the desired category of the high sugar phenotype. The results shown here are from plant and ratoon canes selected under containment greenhouse conditions in the early vegetative generations after regeneration of transgenic sugarcane lines from callus to shoots. Similar screens are possible for diverse plant species, and initial selection rounds would typically be followed by testing replicated plants grown in containment greenhouses and/or approved field trials.

The present inventors envisage other variations on SI constructs to enhance the frequency and extent of desired high sugar phenotypes among transformants. In particular, they envisage preferential expression of the SI gene in particular tissues such as sink tissues and/or particular cell types such as storage parenchyma; combined with targeting of the SI protein to particular cellular compartments, such as storage compartments for high isomaltulose yield or metabolic compartments for high sucrose yields. Optimal SI activity levels will vary depending on the desired category of the high sugar phenotype. For example, relatively high activity in the mature stem vacuoles might be achieved through corresponding expression strength and modification of the SI for protease resistance to enhance isomaltulose yields. Alternatively, low activity in the cytosol might be achieved through a weak promoter and/or modified gene sequence for low mRNA and/or protein stability. Provided below as an example is a construct designed for relatively weak expression that is modulated with stem maturity.

Cloning and Characterization of a Stem-Specific Promoter P67B

Sequence and GUS Reporter Activity in Sugarcane Driven by a Second Promoter Homolog of Sugarcane Mature-Stem Specific Gene 67

Gene 67 described previously (Birch & Potier, 2000) is specifically expressed in mature sugarcane stems as indicated by northern analysis, but a corresponding promoter sequence isolated from the sugarcane genome drove GUS reporter gene expression predominantly in immature stems. Using genomic DNA as template for high fidelity PCR with primers designed from the known promoter (designated P67A) yielded a different putative promoter designated P67B, which at 987 bp is 60 bp shorter than P67A. Alignment of the two versions showed 92.98% identity, with four deletions (49 bp+4 bp+1 bp+1 bp), 2 insertions (1 bp+1 bp) and 18 point mutations in P67B relative to P67A.

In 11 transgenic sugarcane lines with P67B-GUS reporter constructs, no activity was observed in the leaf or the root tissues by GUS histochemical or fluorometric assays. GUS activity was barely detectable by histochemical assay in the stem tissues, indicating low-level expression. The fluorometric assay with extended incubation to enhance sensitivity indicated increased activity with stem maturity in at least one P67B-GUS line, in contrast with the greater expression in younger internodes of a P67A-GUS line (FIG. 20). The contrasting pattern between these lines was maintained over two tested vegetative generations.

Cytoplasmic Expression of the UQ68J SI Gene Driven by Promoter 67A or 67B

High Sucrose Concentration was Detected in Some Transgenic Lines with Recombinant UQ68J SI Gene Driven by Promoter 67B Isomaltulose was not detected in leaves or roots of transgenic lines positive in PCR tests for the introduced SI gene driven by P67A or P67B. It was detected at low concentrations (<3 mM) in mature stem tissues of 3/9 tested P67A-SI lines and 8/18 P67B-SI lines, all of which showed normal growth and development.

All isomaltulose-negative lines and eight of the eleven isomaltulose-positive lines had similar total sugar contents in mature internodes to the Q117 control. Three lines with SI driven by the 67B promoter (P67B68J1.5, P67B68J2.5 and P67B68J2.6) accumulated sugar levels about 1.8 times the level in the Q117 control. The increase was primarily in sucrose content, with variable contributions from increased glucose and fructose (Table 7).

TABLE 7

Sugar content in $20^{th}$ internodes of isomaltulose-positive transgenic lines with SI driven by promoter 67A or 67B, and in the Q117 control.

| Transgenic line | Glucose (mM) | Fructose (mM) | Sucrose (mM) | Isomaltulose (mM) | Total sugar (mM, Sucrose-equivalent) |
|---|---|---|---|---|---|
| P67B68J1.5 | 43.6 | 31.2 | 723.3 | 2.2 | 762.9 |
| P67B68J2.5 | 12.3 | 8.7 | 716.5 | 0.8 | 727.8 |
| P67B68J2.6 | 10.0 | 6.2 | 716.9 | 1.2 | 726.2 |
| P67B68J2.1 | 6.9 | 7.1 | 465.3 | 0.3 | 472.6 |
| P67B68J2.2 | 1.3 | 0.9 | 470.8 | 0.5 | 472.4 |
| P67B68J1.4 | 6.1 | 8.0 | 400.4 | 1.0 | 403.5 |
| P67B68J1.6 | 1.6 | 0.9 | 397.3 | 0.2 | 398.8 |
| P67B68J3.2 | 0.5 | 0.4 | 288.9 | 1.0 | 290.3 |
| P67A68J1.6 | 2.0 | 2.3 | 414.2 | 0.7 | 417.1 |
| P67A68J2.8 | 2.1 | 1.6 | 405.0 | 0.3 | 407.2 |
| P67A68J1.5 | 5.1 | 3.3 | 394.1 | 0.7 | 399.0 |
| Q117 | 1.6 | 1.2 | 403.1 | 0.0 | 404.5 |

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

Ausubel F M, Brent R, Kingston R E, Moore D D, Seidman J G, Smith J A, Struhl K, eds (1990) *Current Protocols in Molecular Biology*. New York: John Wiley and Sons.

Bevan M W, Flavell R B, Chilton M-D (1983) A chimaeric antibiotic resistance gene as a selectable marker for plant cell transformation. *Nature* 304, 184-187.

Birch R G (1997) Plant transformation: problems and strategies for practical application. *Annu. Rev. Plant Physiol. Plant Molec. Biol.* 48, 297-326.

Birch R G (2000) Sugarcane transformation: microprojectile bombardment of embryogenic callus & geneticin selection. www.botany.uq.edu.au/people/rbirch/scshooting.pdf (accessed 5 May 2004)

Birch R G, Potier B A M (2000) Sugarcane plant promoters to express heterologous nucleic acids. International Patent Specification PCT/AU99/01033; WO 01/18211 A1. Assigned to: The University of Queensland.

Birch R G, Wu L (2002) Sucrose isomerases. International Patent Specification WO 02/18603 A1 publ. 7 Mar. 2002. [US2004005589 A1 8 Jan. 2004; AU 8160901 13 Mar. 2002; PCT/AU01/01084 filed 29 Aug. 2001; AU PQ 9768 filed 29 AUG2000] (Assigned to: University of Queensland).

Börnke F, Sonnewald U (2001a) Production of non-cariogenic sugars in transgenic plants. International Patent Specification PCT/EP01/01603 AU200135474 lapsed 18 Dec. 2003; WO 01/59136 A1 publ. 16 Aug. 2001 (De); PCT/EP01/01603 filed 14 Feb. 2001 (De); DE 100 06 462.0 filed 14 Feb. 2000 (De)].

Börnke F, Sonnewald U (2001b) Method for influencing the pollen development by modifying the sucrose metabolism. Application: DE 100 06 413.2, 100 45 113.6, 14 Feb. 2000, 13 Sep. 2000. International Patent Application PCT/EPO/01412, WO 01/59135 A1, issued 16 Aug. 2001.

Börnke F, Hajirezaei M, Heineke D, Melzer M, Herbers K, Sonnewald U (2002a) High-level production of the non-cariogenic sucrose isomer palatinose in transgenic tobacco plants strongly impairs development. *Planta* 214, 356-364.

Börnke F, Hajirezaei M, Sonnewald U (2002b) Potato tubers as bioreactors for palatinose production. *J. Biotechnol.* 96, 119-124.

Botha F C, Sawyer B J B, Birch R G (2001) Sucrose metabolism in the culm of transgenic sugarcane with reduced soluble acid invertase activity. In *Proceedings of the International Society of Sugarcane Technologists XXIV Congress*, Brisbane, September 2001, Volume II (Hogarth D M, ed) Mackay: ASSCT, pp. 588-591.

Bower R, Elliott A R, Potier B A M, Birch R G (1996) High-efficiency, microprojectile-mediated cotransformation of sugarcane, using visible or selectable markers. *Molec. Breed.* 2, 239-249.

Bradford M (1976) A rapid and sensitive method for the quantification of microgram quantities of protein using the principle of protein-dye binding. *Anal. Biochem.* 72, 248-254.

Bugos R C, Chiang V L, Zhang X H, Campbell E R, Podila G K, Campbell W H (1995) RNA isolation from plant tissues recalcitrant to extraction in guanidine. *BioTechniques* 19, 734-737.

Christensen A H, Quail P H (1996) Ubiquitin promoter-based vectors for high-level expression of selectable and/or screenable marker genes in monocotyledonous plants. *Transgen. Res.* 5, 213-218.

Cortina C, Culianez-Macia F A (2004) Tomato transformation and transgenic plant production. *Plant Cell Tissue and Organ Culture* 76, 269-275.

Demuth K, Jordening H J, Buchholz K (2002) Oligosaccharide synthesis by dextransucrase: new unconventional acceptors. *Carbohydrate Research* 337, 1811-1820.

Fernie, A R, Roessner, U, Geigenberger, P (2001) The sucrose analog palatinose leads to a stimulation of sucrose degradation and starch synthesis when supplied to discs of growing potato tubers. *Plant Physiol.* 125, 1967-1977.

Fernie A R, Willmitzer L, Trethewey R N (2002) Sucrose to starch: a transition in molecular plant physiology. *Trends in Plant Science* 7, 35-41.

Ganapathi T R, Higgs N S, Balint-Kurti P J, Arntzen C J, May G D, Van Eck J M (2001) *Agrobacterium*-mediated transformation of embryogenic cell suspensions of the banana cultivar Rasthali (AAB). *Plant Cell Reports* 20, 157-162.

Gnanasambandam A, Birch R G (2004) Efficient developmental mis-targeting by the sporamin NTPP vacuolar signal to plastids in young leaves of sugarcane and *Arabidopsis*. *Plant Cell Reports* Submitted.

Graan T, Ort D R (1984) Quantitation of the rapid electron donors to P700, the functional plastoquinone pool, and the ratio of the photosystems in spinach chloroplasts. *J. Biol. Chem.* 259, 14003-14010.

Grant J E, Thomson L M J, Pither-Joyce M D, Dale T M, Cooper P A (2003) Influence of *Agrobacterium tumefaciens* strain on the production of transgenic peas (*Pisum sativum* L.). *Plant Cell Reports* 21, 1207-1210.

Hansom S, Bower R, Zhang L, Potier B, Elliott A, Basnayake S, Cordeiro G, Hogarth D M, Cox M, Berding N, Birch R G (1999) Regulation of transgene expression in sugarcane. In *Proceedings of the International Society of Sugarcane Technologists XXIII Congress*, New Delhi, February 1999, pp. 278-290. Edited by V. Singh. New Dehli: STAI.

Hermann S R, Harding R M, Dale J L (2001) The banana actin 1 promoter drives near-constitutive transgene expression in vegetative tissues of banana (*Musa* spp.). *Plant Cell Reports* 20, 525-530.

Jeoung J M, Krishnaveni S, Muthukrishnan S, Trick H N, Liang G H (2002) Optimization of sorghum transformation parameters using genes for green fluorescent protein and beta-glucuronidase as visual markers. *Hereditas* 137, 20-28.

Joersbo M, Mikkelsen J D, Brunstedt J (2000) Relationship between promoter strength and transformation frequencies using mannose selection for the production of transgenic sugar beet. *Molecular Breeding* 6, 207-213.

Kunz M, Mattes R, Munir M, Vogel M (2002) Transgenic plants which produce isomalt. International Patent Specification WO 02/27003 A1 publ. 4 Apr. 2002 (De). [USA 2004/0064851 A1 publ. 1 Apr. 2004 (En); AU200176398 examination direction 18 Mar. 2004; PCT/EP01/08055 filed 12 Jul. 2001 (De); DE 100 47 286.9 filed 20 Sep. 2000 (De)].

Laemmli U K (1970) Cleavage of structural proteins during the assembly of the head of bacteriophage T4. *Nature* 227, 680-685.

Lessard P A, Kulaveerasingam H, York G M, Strong A, Sinskey A J (2002) Manipulating gene expression for the metabolic engineering of plants. *Metabolic Engineering* 4, 67-79.

Loreti E, Alpi A, Perata P (2000) Glucose and disaccharide-sensing mechanisms modulate the expression of alpha-amylase in barley embryos. *Plant Physiol.* 123, 939-948.

Martin M T Cruces M A, Alcalde M, Plou F J, Bernabe M, Ballesteros A (2004) Synthesis of maltooligosyl fructofuranosides catalyzed by immobilized cyclodextrin glucosyltransferase using starch as donor. *Tetrahedron* 60, 529-534.

Mattes R, Klein K, Schiweck H, Kunz M, Munir M (1995) Preparation of acariogenic sugar substitutes. International Patent Specification WO 95/20047 A3 publ. 27 Jul. 1995. [USA 2003207437 6 Nov. 2003; USA 2003203468 30 Oct. 2003; USA 2003087416 8 May 2003; USA 5985622 16 Nov. 1999; USA 5786140 27 Jul. 1998; AU 688848 19 Mar. 1998; PCT/EP95/00165 filed 18 Jan. 1995; DE 44 14 185 filed 22 Apr. 1994; DE 44 01 451 filed 19 Jan. 1994] (Assigned to: Südzucker Aktiengellschaft).

Matzke A J M, Matzke M A (1998) Position effects and epigenetic silencing of plant transgenes. *Current Opinion in Plant Biology* 1, 142-148.

Moore P H (1995) Temporal and spatial regulation of sucrose accumulation in the sugarcane stem. *Australian Journal of Plant Physiology* 22, 661-679.

Nguyen-Quoc B, Foyer C H (2001) A role for 'futile cycles' involving invertase and sucrose synthase in sucrose metabolism of tomato fruit. *Journal of Experimental Botany* 52, 881-889.

Park H E, Park N H, Kim M J, Lee T H, Lee H G, Yang J Y, Cha J (2003) Enzymatic synthesis of fructosyl oligosaccharides by levansucrase from *Microbacterium laevaniformans* ATCC 15953. *Enzyme and Microbial Technology* 32, 820-827.

Peach C, Velten J (1991) Transgene expression variability (position effect) of CAT and GUS reporter genes driven by linked divergent T-DNA promoters. *Plant Molecular Biology* 17, 49-60.

Plou F J, Martin M T, de Segura A G, Alcalde M, Ballesteros A (2002) Glucosyltransferases acting on starch or sucrose for the synthesis of oligosaccharides. *Canadian Journal of Chemistry-Revue Canadienne De Chimie* 80, 743-752.

Polowick P L, Vandenberg A, Mahon J D (2002) Field assessment of outcrossing from transgenic pea (*Pisum sativum* L.) plants. *Transgenic Research* 11, 515-519.

Saha B C (2004) Purification and characterization of a novel mannitol dehydrogenase from *Lactobacillus intermedius*. *Biotechnology Progress* 20, 537-542.

Sambrook J, Russell D W (2001) *Molecular Cloning: A Laboratory Manual*, 3rd edn. New York: Cold Spring Harbor Laboratory Press.

Sinha A K, Hofmann M G, Romer U, Kockenberger W, Elling L, Roitsch T (2002) Metabolizable and non-metabolizable sugars activate different signal transduction pathways in tomato. *Plant Physiol.* 128, 1480-1489.

Small I, Wintz H, Akashi K, Mireau H (1998) Two birds with one stone: genes that encode products targeted to two or more compartments. *Plant Molecular Biology* 38, 265-277.

Tadesse Y, Sagi L, Swennen R, Jacobs M (2003) Optimisation of transformation conditions and production of transgenic sorghum (*Sorghum bicolor*) via microparticle bombardment. *Plant Cell Tissue and Organ Culture* 75, 1-18.

van der Veen B A, Potocki-Veronese G, Albenne C, Joucla G, Monsan P, Remaud-Simeon M (2004) Combinatorial engineering to enhance amylosucrase performance: construction, selection, and screening of variant libraries for increased activity. *FEBS Letters* 560, 91-97.

Veronese T, Perlot P (1999) Mechanism of sucrose conversion by the sucrose isomerase of *Serratia plymuthica* ATCC 15928. *Enzyme. Microb. Technol.* 24, 263-269.

Vidal J R, Kikkert J R, Wallace P G, Reisch B I (2003) High-efficiency biolistic co-transformation and regeneration of 'Chardonnay' (*Vitis vinifera* L.) containing npt-II and antimicrobial peptide genes. *Plant Cell Reports* 22, 252-260.

Vitale A, Raikhel N V (1999) What do proteins need to reach different vacuoles? *Trends in Plant Science* 4, 149-155.

Wu L, Birch R G (2004) Characterisation of *Pantoea dispersa* UQ68J: producer of a highly efficient sucrose isomerase for isomaltulose biosynthesis. *Journal of Applied Microbiology*. In press Wu L, Joshi C P, Chiang V L (2000) A xylem-specific cellulose synthase gene from aspen (*Populus tremuloides*) is responsive to mechanical stress. *Plant Journal* 22, 495-502.

Zhang C L, Chen D F, McCormac A C, Scott N W, Elliott M C, Slater A (2001) Use of the GFP reporter as a vital marker for *Agrobacterium*-mediated transformation of sugar beet (*Beta vulgaris* L.). *Molecular Biotechnology* 17, 109-117.

Zhang S, Williams-Carrier R, Lemaux P G (2002) Transformation of recalcitrant maize elite inbreds using in vitro shoot meristematic cultures induced from germinated seedlings. *Plant Cell Reports* 21, 263-270.

Zhifang G, Loescher W H (2003) Expression of a celery mannose 6-phosphate reductase in *Arabidopsis thaliana* enhances salt tolerance and induces biosynthesis of both mannitol and a glucosyl-mannitol dimer. *Plant Cell and Environment* 26, 275-283.

What is claimed is:

1. A method of producing a plant having sink tissue which has increased sweetness or an increased total or soluble carbohydrate content or an increased content of an endogenous carbohydrate as compared to a corresponding sink tissue of a control plant, the method comprising selecting from a plurality of transgenic plants which comprise in their nucleome a polynucleotide that is operably connected to a transcriptional control element and that encodes a sucrose isomerase that catalyzes the conversion of sucrose to an alien sugar, a plant that produces the sucrose isomerase at a level or functional activity so that 1) the total or soluble carbohydrate content or sweetness or 2) the content of the endogenous carbohydrate of the sink tissue of the transgenic plant is increased as compared to that of the corresponding sink tissue of the control plant, wherein the sucrose is an endogenous sugar of the plant, wherein the alien sugar is selected from the group consisting of isomaltulose and trehalulose, and wherein the plant is sugarcane, which is a plant capable of accumulating sucrose as a storage product.

2. A method according to claim 1, wherein the sucrose isomerase is produced in the cells of the plant at a level or functional activity that results in less than about 20% conversion of the sucrose to the alien sugar.

3. A method according to claim 1, wherein the sucrose isomerase comprises a targeting signal that targets the sucrose isomerase to a plant sub-cellular compartment that is used for sugar storage.

4. A method according to claim 3, wherein the sucrose isomerase is distributed between cytosolic and storage compartments.

5. A method according to claim 3, wherein the sucrose isomerase is substantially confined to the storage compartment.

6. A method according to claim 3, wherein the storage compartment is selected from the group consisting of the vacuole and the apoplasmic space.

7. A method according to claim 1, wherein the sucrose isomerase is produced in the cells of the plant at a level or functional activity that results in at least about 20% conversion of the sucrose to the alien sugar.

8. A method according to claim 7, wherein the conversion occurs within tissues that have substantially ceased cell division or cell expansion and that are functional for carbohydrate storage.

9. A method according to claim 8, wherein the conversion occurs within tissues that have substantially ceased cell division or cell expansion and that are functional for carbohydrate storage and wherein the sugar-metabolizing enzyme is produced at a level or functional activity that results in less than about 20% conversion of the sucrose to the alien sugar within tissues undergoing cell division or cell expansion contributing to plant growth.

10. A method according to claim 1, wherein the alien sugar is accumulated without commensurable reduction in the content of endogenous sugars or carbohydrates.

11. A method according to claim 10, wherein the polynucleotide is constitutively expressed.

12. A method according to claim 10, wherein the polynucleotide is selectively expressed.

13. A method according to claim 10, wherein the polynucleotide is selectively expressed in the sink tissue of the plant.

14. A method according to claim 1, wherein the sink tissue is selected from the group consisting of roots, tubers, stems, culms, fruits and seeds.

15. A method according to claim 14, wherein the sucrose isomerase is UQ68J.

16. A method according to claim 1, wherein the soluble carbohydrates are selected from the group consisting of sucrose, glucose and fructose.

17. A method according to claim 1, wherein the endogenous carbohydrate is selected from the group consisting of sucrose, glucose and fructose.

18. A transgenic sugarcane plant sink cell which has 1) an increased total carbohydrate content or 2) an increased soluble carbohydrate content with an increased content of an endogenous carbohydrate as compared to a control sugarcane plant cell, the transgenic sugarcane plant cell comprising in its nucleome a transcriptional control element operably connected to a polynucleotide that encodes a sucrose isomerase that catalyzes the conversion of sucrose to an alien sugar, wherein the sucrose isomerase is produced at a level or functional activity so that the total carbohydrate content of the transgenic sugarcane plant cell is increased, or the soluble carbohydrate content of the transgenic sugarcane plant cell is increased with an increase in the content of the endogenous carbohydrate, as compared to that of the control sugarcane plant cell, wherein the sucrose is an endogenous sugar of the plant, wherein the alien sugar is selected from the group consisting of isomaltulose and trehalulose, wherein the sugarcane plant is a plant capable of accumulating sucrose as a storage product, and wherein the total sugar content of the transgenic plant cell is increased by at least 10% above the sugar content of the control sugarcane plant cell.

19. A transgenic sugarcane plant sink cell according to claim 18, wherein the sucrose isomerase is produced in the transgenic sugarcane plant cell at a level or functional activity that results in less than about 20% conversion of the sucrose to the alien sugar.

20. A transgenic sugarcane plant sink cell which has 1) an increased total carbohydrate content or 2) an increased soluble carbohydrate content with an increased content of an endogenous carbohydrate as compared to a control sugarcane plant cell, the transgenic sugarcane plant cell comprising in its nucleome a transcriptional control element operably connected to a polynucleotide that encodes a sucrose isomerase that catalyzes the conversion of sucrose to an alien sugar, wherein the sucrose isomerase is produced at a level or functional activity so that the total carbohydrate content of the transgenic sugarcane plant cell is increased, or the soluble carbohydrate content of the transgenic sugarcane plant cell is increased with an increase in the content of the endogenous carbohydrate, as compared to that of the control sugarcane plant cell, wherein the sucrose is an endogenous sugar of the plant, wherein the alien sugar is selected from the group consisting of isomaltulose and trehalulose, wherein the sugarcane plant is a plant capable of accumulating sucrose as a storage product, wherein the sucrose isomerase is produced at a level or functional activity that results in less than about 20% conversion of the sucrose to the alien sugar, and wherein the transgenic sugarcane plant cell is undergoing cell division or expansion.

21. A transgenic sugarcane plant cell according to claim 18 or claim 20, wherein the sucrose isomerase comprises a targeting signal that targets the sucrose isomerase to a sugarcane plant sub-cellular compartment that is used for sugar storage.

22. A transgenic sugarcane plant cell according to claim 21, wherein the sucrose isomerase is distributed between cytosolic and storage compartments.

23. A transgenic sugarcane plant cell according to claim 21, wherein the sucrose isomerase is substantially confined to the storage compartment.

24. A transgenic sugarcane plant cell according to claim 21, wherein the storage compartment is selected from the group consisting of the vacuole and the apoplasmic space.

25. A transgenic sugarcane plant cell according to claim 18, wherein the sucrose isomerase is produced at a level or functional activity that results in at least about 20% conversion of the endogenous sugar to the alien sugar.

26. A transgenic sugarcane plant cell according to claim 25, wherein the conversion occurs when the transgenic sugarcane plant cell has substantially ceased cell division or expansion and is functional for carbohydrate storage.

27. A transgenic sugarcane plant cell according to claim 18 or claim 20, wherein the alien sugar is accumulated without commensurable reduction in the content of endogenous sugars or carbohydrates.

28. A transgenic sugarcane plant cell according to claim 18 or claim 20, wherein the sugarcane plant cell is a plant stem cell.

29. A transgenic sugarcane plant cell according to claim 18 or claim 20, wherein the soluble carbohydrates are selected from simple sugars.

30. A transgenic sugarcane plant cell according to claim 29, wherein the simple sugars are selected from the group consisting of sucrose, glucose and fructose.

31. A transgenic sugarcane plant cell according to claim 18 or claim 20, wherein the endogenous carbohydrate is selected from simple sugars.

32. A transgenic sugarcane plant cell according to claim 31, wherein the simple sugars are selected from the group consisting of sucrose, glucose and fructose.

33. A transgenic sugarcane plant having sink tissue which has 1) increased total carbohydrate content or 2) an increased soluble carbohydrate content or sweetness with an increased content of an endogenous carbohydrate as compared to a corresponding sink tissue of a control plant, the transgenic sugarcane plant comprising cells which comprise in their nucleome a transcriptional control element that is operably connected to a polynucleotide that encodes a sucrose isomerase that catalyzes the conversion of sucrose to an alien sugar, wherein the sucrose isomerase is produced at a level or functional activity so that the total carbohydrate content of the sink tissue of the transgenic sugarcane plant is increased, or the soluble carbohydrate content or sweetness of the sink tissue of the transgenic sugarcane plant is increased with an increase in the content of the endogenous carbohydrate as compared to that of the corresponding sink tissue of the control plant, wherein the sucrose is an endogenous sugar of the sugarcane plant, wherein the alien sugar is selected from the group consisting of isomaltulose and trehalulose, wherein the sugarcane plant is a plant capable of accumulating sucrose as a storage product, and wherein the total sugar content of the transgenic plant is increased by at least 10% above the sugar content of the control plant.

34. A transgenic sugarcane plant having sink tissue which has 1) increased total carbohydrate content or 2) an increased soluble carbohydrate content or sweetness with an increased content of an endogenous carbohydrate as compared to a corresponding sink tissue of a control plant, the transgenic sugarcane plant comprising cells which comprise in their nucleome a transcriptional control element that is operably connected to a polynucleotide that encodes a sucrose isomerase that catalyzes the conversion of sucrose to an alien sugar, wherein the sucrose isomerase is produced at a level or functional activity so that the total carbohydrate content of the sink tissue of the transgenic sugarcane plant is increased, or the soluble carbohydrate content or sweetness of the sink tissue of the transgenic sugarcane plant is increased with an increase in the content of the endogenous carbohydrate as compared to that of the corresponding sink tissue of the control plant, wherein the sucrose is an endogenous sugar of the sugarcane plant, wherein the alien sugar is selected from the group consisting of isomaltulose and trehalulose, wherein the sugarcane plant is a plant capable of accumulating sucrose as a storage product, wherein the sucrose isomerase is produced in the sugarcane plant cells at a level or functional activity that results in less than about 20% conversion of the sucrose to the alien sugar.

35. A transgenic sugarcane plant according to claim 33 or claim 34, wherein the sucrose isomerase comprises a targeting signal that targets the sucrose isomerase to a sugarcane plant sub-cellular compartment that is used for sugar storage.

36. A transgenic sugarcane plant according to claim 35, wherein the sucrose isomerase is distributed between cytosolic and storage compartments.

37. A transgenic sugarcane plant according to claim 35, wherein the sucrose isomerase is substantially confined to the storage compartment.

38. A transgenic sugarcane plant according to claim 35, wherein the storage compartment is selected from the group consisting of the vacuole and the apoplasmic space.

39. A transgenic sugarcane plant according to claim 33, wherein the sucrose isomerase is produced at a level or functional activity that results in at least about 20% conversion of the sucrose to the alien sugar.

40. A transgenic sugarcane plant according to claim 39, wherein the conversion occurs within tissues that have substantially ceased cell division or cell expansion and that are functional for carbohydrate storage.

41. A transgenic sugarcane plant according to claim 33, wherein the conversion occurs within tissues that have substantially ceased cell division or cell expansion and that are functional for carbohydrate storage and wherein the sucrose isomerase is produced at a level or functional activity that results in less than about 20% conversion of the sucrose to the alien sugar within tissues undergoing cell division or cell expansion contributing to sugarcane plant growth.

42. A transgenic sugarcane plant having sink tissue which has 1) increased total carbohydrate content or 2) an increased soluble carbohydrate content or sweetness as compared to a corresponding sink tissue of a control plant, the transgenic sugarcane plant comprising cells which comprise in their nucleome a transcriptional control element that is operably connected to a polynucleotide that encodes a sucrose isomerase that catalyzes the conversion of sucrose to an alien sugar, wherein the sucrose isomerase is produced at a level or functional activity so that the total carbohydrate content of the sink tissue of the transgenic sugarcane plant is increased, or the soluble carbohydrate content or sweetness of the sink tissue of the transgenic sugarcane plant is increased as compared to that of the corresponding sink tissue of the control plant, wherein the sucrose is an endogenous sugar of the sugarcane plant, wherein the alien sugar is selected from the group consisting of isomaltulose and trehalulose, wherein the sugarcane plant is a plant capable of accumulating sucrose as a storage product, wherein the alien sugar is accumulated without commensurable reduction in the content of endogenous sugars or carbohydrates.

43. A transgenic sugarcane plant according to any one of claims 33, 34, or 42, wherein the sugarcane plant cells are plant stem cells.

44. A transgenic sugarcane plant according to any one of claims 33, 34, or 42, wherein the soluble carbohydrates are selected from simple sugars.

45. A transgenic sugarcane plant according to claim 44, wherein the simple sugars are selected from the group consisting of sucrose, glucose and fructose.

46. A transgenic sugarcane plant according to any one of claims 33, 34, or 42, wherein the endogenous carbohydrate is selected from simple sugars.

47. A transgenic sugarcane plant according to claim 46, wherein the simple sugars are selected from the group consisting of sucrose, glucose and fructose.

48. A transgenic sugarcane plant sink tissue of a plant according to any one of claims 33, 34, or 42.

49. A process for producing soluble carbohydrates, the process comprising harvesting soluble carbohydrates from a plant according to claim 33.

50. A process for producing a product by fermentation, the process comprising fermenting carbohydrates, which are substrates for fermentation and which are produced by harvesting soluble carbohydrates from a plant according to claim 33.

51. A process for producing a product by fermentation, the process comprising fermenting carbohydrates, which are substrates for fermentation and which are produced by harvesting soluble carbohydrates from a plant according to claim 33, wherein the fermentation product produced by the process comprises at least one substance selected from the group consisting of ethanol, methanol, 1,3-propanediol, acetic acid, citric acid, succinic acid, lactic acid, sorbitol, lysine, polyhydroxyalkanoate, carbon dioxide, an industrial enzyme, and a polymer comprising any of these.

52. A transgenic sugarcane plant having sink tissue which has 1) increased total carbohydrate content or 2) an increased soluble carbohydrate content or sweetness with an increased content of an endogenous carbohydrate or 3) an accumulation of an alien sugar without commensurate reduction in the content of endogenous sugars or carbohydrates as compared to a corresponding sink tissue of a control sugarcane plant, the transgenic sugarcane plant comprising cells which comprise in their nucleome a transcriptional control element that is operably connected to a polynucleotide that encodes a sucrose isomerase that catalyzes the conversion of sucrose to an alien sugar, wherein the sucrose isomerase is produced at a level or functional activity so that the total carbohydrate content of the sink tissue of the transgenic sugarcane plant is increased, or the soluble carbohydrate content or sweetness of the sink tissue of the transgenic sugarcane plant is increased with an increase in the content of the endogenous carbohydrate or the alien sugar is accumulated without commensurable reduction in the content of endogenous sugars or carbohydrates as compared to that of the corresponding sink tissue of the control sugarcane plant, wherein the sucrose isomerase is produced in the plant cells at a level or functional activity that results in less than about 20% conversion of the endogenous sugar to the alien sugar, wherein the sucrose is an endogenous sugar of the sugarcane plant, wherein the alien sugar is selected from the group consisting of isomaltulose and trehalulose, and wherein the sugarcane plant is a plant capable of accumulating sucrose as a storage product.

53. A transgenic sugarcane plant having sink tissue which has 1) increased total carbohydrate content or 2) an increased soluble carbohydrate content or sweetness with an increased content of an endogenous carbohydrate or 3) an accumulation of an alien sugar without commensurate reduction in the content of endogenous sugars or carbohydrates as compared to a corresponding sink tissue of a control sugarcane plant, the transgenic sugarcane plant comprising cells which comprise in their nucleome a transcriptional control element that is operably connected to a polynucleotide that encodes a sucrose isomerase that catalyzes the conversion of sucrose to an alien sugar, wherein the sucrose isomerase is produced at a level or functional activity so that the total carbohydrate content of the sink tissue of the transgenic sugarcane plant is increased, or the soluble carbohydrate content or sweetness of the sink tissue of the transgenic sugarcane plant is increased with an increase in the content of the endogenous carbohydrate or the alien sugar is accumulated without commensurable reduction in the content of endogenous sugars or carbohydrates as compared to that of the corresponding sink tissue of the control sugarcane plant, wherein the sucrose isomerase is distributed between cytosolic and storage compartments or is confined to the storage compartment, wherein the sucrose isomerase is produced in the plant cells at a level or functional activity that results in at least 20% conversion of the endogenous sugar to the alien sugar, wherein the sucrose is an endogenous sugar of the sugarcane plant, wherein the alien sugar is selected from the group consisting of isomaltulose and trehalulose, and wherein the sugarcane plant is a plant capable of accumulating sucrose as a storage product.

54. A transgenic sugarcane plant according to any one of claims 42, 52, or 53, wherein the sucrose isomerase comprises a targeting signal that targets the sucrose isomerase to a sugarcane plant sub-cellular compartment that is used for sugar storage.

55. A transgenic sugarcane plant according to claim 54, wherein the sucrose isomerase is distributed between cytosolic and storage compartments.

56. A transgenic sugarcane plant according to claim 54, wherein the sucrose isomerase is substantially confined to the storage compartment.

57. A transgenic sugarcane plant according to claim 54, wherein the storage compartment is selected from the group consisting of the vacuole and the apoplasmic space.

58. A high carbohydrate yielding transgenic sugarcane plant which is obtained by a process comprising introducing a construct into the nucleome of a plurality of sugarcane plants to produce a plurality of transgenic sugarcane plants, wherein the construct comprises a transcriptional control element operably connected to a polynucleotide that encodes a sucrose isomerase that catalyzes the conversion of sucrose to an alien sugar, selecting the high carbohydrate yielding transgenic sugarcane plant from the plurality of transgenic sugarcane plants, wherein the sucrose isomerase is produced at a level or functional activity so that 1) the total carbohydrate content of the sink tissue of the transgenic sugarcane plant is increased, or 2) the soluble carbohydrate content or sweetness of the sink tissue of the transgenic sugarcane plant is increased with an increase in the content of the endogenous carbohydrate, or 3) the alien sugar is accumulated without commensurable reduction in the content of endogenous sugars or carbohydrates, as compared to that of the corresponding sink tissue of a control sugarcane plant, wherein the sucrose is an endogenous sugar of the sugarcane plant, wherein the alien sugar is selected from the group consisting of isomaltulose and trehalulose, and wherein the sugarcane plant is a plant capable of accumulating sucrose as a storage product.

59. The high carbohydrate yielding transgenic sugarcane plant according to claim 58, wherein the total sugar content of the transgenic sugarcane plant is increased by at least 10% above the endogenous sugar content of the control sugarcane plant.

60. The high carbohydrate yielding transgenic sugarcane plant according to claim 58, wherein the total sugar content of the transgenic sugarcane plant is increased by at least 50% above the endogenous sugar content of the control sugarcane plant.

61. The high carbohydrate yielding transgenic sugarcane plant according to claim 58, wherein the total sugar content of the transgenic sugarcane plant is increased by at least 100% above the endogenous sugar content of the control sugarcane plant.

62. The high carbohydrate yielding transgenic sugarcane plant according to claim 58, comprising an increased ratio of soluble carbohydrates per unit weight of sink tissue, as compared to that measured in the control sugarcane plant.

63. A transgenic sugarcane plant sink cell which has an increased total carbohydrate content, or an increased soluble carbohydrate content with an increased content of an endogenous carbohydrate or an accumulation of an alien sugar without commensurate reduction in the content of endogenous sugars or carbohydrates, as compared to a control sugarcane plant cell, wherein the transgenic sugarcane plant sink cell is derived from the high carbohydrate yielding sugarcane plant according to claim 58.

64. The transgenic sugarcane plant sink cell according to claim 63, wherein the total sugar content of the transgenic sugarcane plant sink cell is increased by at least 10% above the sugar content of the control sugarcane plant sink cell.

65. The transgenic sugarcane plant sink cell according to claim 63, wherein the total sugar content of the transgenic sugarcane plant sink cell is increased by at least 50% above the sugar content of the control sugarcane plant sink cell.

66. The transgenic sugarcane plant sink cell according to claim 63, wherein the total sugar content of the transgenic sugarcane plant sink cell is increased by at least 100% above the sugar content of the control sugarcane plant sink cell.

67. A transgenic sugarcane plant sink cell which has 1) an increased total carbohydrate content or 2) an increased soluble carbohydrate content with an increased content of an endogenous carbohydrate as compared to a control sugarcane plant cell, the transgenic sugarcane plant cell comprising in its nucleome a transcriptional control element operably connected to a polynucleotide that encodes a sucrose isomerase that catalyzes the conversion of sucrose to an alien sugar, wherein the sucrose isomerase is produced at a level or functional activity so that the total carbohydrate content of the transgenic sugarcane plant cell is increased, or the soluble carbohydrate content of the transgenic sugarcane plant cell is increased with an increase in the content of the endogenous carbohydrate, as compared to that of the control sugarcane plant cell, wherein the sucrose is an endogenous sugar of the plant, wherein the alien sugar is selected from the group consisting of isomaltulose and trehalulose, wherein the sugarcane plant is a plant capable of accumulating sucrose as a storage product, and wherein the sucrose isomerase is produced at a level or functional activity that results in less than about 20% conversion of the sucrose to the alien sugar.

68. The method according to claim 15, wherein the polynucleotide comprises SEQ ID NO:25.

69. The transgenic sugarcane sink cell of any one of claims 18, 20 or 67, wherein the sucrose isomerase is UQ68J.

70. The transgenic sugarcane sink cell of claim 69, wherein the polynucleotide comprises SEQ ID NO:25.

71. The transgenic sugarcane plant of any one of claims 33, 34, 42, 52, 53 or 58, wherein the sucrose isomerase is UQ68J.

72. The transgenic sugarcane plant of claim 71, wherein the polynucleotide comprises SEQ ID NO:25.

73. The transgenic sugarcane sink tissue of claim 48, wherein the sucrose isomerase is UQ68J.

74. The transgenic sugarcane sink tissue of claim 73, wherein the polynucleotide comprises SEQ ID NO:25.

75. A process for producing soluble carbohydrates, the process comprising harvesting soluble carbohydrates from a sink tissue according to claim 48.

76. A process for producing a product by fermentation, the process comprising fermenting carbohydrates, which are substrates for fermentation and which are produced by harvesting soluble carbohydrates from a sink tissue according to claim 48.

77. A process for producing a product by fermentation, the process comprising fermenting carbohydrates, which are substrates for fermentation and which are produced by harvesting soluble carbohydrates from a sink tissue according to claim 48, wherein the fermentation product produced by the process comprises at least one substance selected from the group consisting of ethanol, methanol, 1,3-propanediol, acetic acid, citric acid, succinic acid, lactic acid, sorbitol, lysine, polyhydroxyalkanoate, carbon dioxide, an industrial enzyme, and a polymer comprising any of these.

* * * * *

UNITED STATES PATENT AND TRADEMARK OFFICE
CERTIFICATE OF CORRECTION

| | | |
|---|---|---|
| PATENT NO. | : 7,655,836 B2 | Page 1 of 1 |
| APPLICATION NO. | : 10/845059 | |
| DATED | : February 2, 2010 | |
| INVENTOR(S) | : Birch et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 846 days.

Signed and Sealed this

Thirtieth Day of November, 2010

David J. Kappos
*Director of the United States Patent and Trademark Office*